United States Patent
Upshaw

(10) Patent No.: US 8,765,984 B2
(45) Date of Patent: Jul. 1, 2014

(54) METHODS AND SYSTEMS FOR MAKING THIOL COMPOUNDS FROM TERMINAL OLEFINIC COMPOUNDS

(75) Inventor: Thomas A. Upshaw, Bartlesville, OK (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 13/465,054

(22) Filed: May 7, 2012

(65) Prior Publication Data

US 2012/0232297 A1  Sep. 13, 2012

Related U.S. Application Data

(62) Division of application No. 12/427,467, filed on Apr. 21, 2009, now abandoned.

(60) Provisional application No. 61/046,701, filed on Apr. 21, 2008.

(51) Int. Cl.
*C07C 321/02* (2006.01)
*C07C 319/04* (2006.01)

(52) U.S. Cl.
CPC .............. *C07C 321/02* (2013.01); *C07C 319/04* (2013.01)
USPC .......................................................... 554/102

(58) Field of Classification Search
CPC ............................. C07C 321/02; C07C 319/04
USPC .......................................................... 554/102
See application file for complete search history.

(56) References Cited

U.S. PATENT DOCUMENTS

| | | | |
|---|---|---|---|
| 2,411,954 A | 12/1946 | Burke | |
| 3,629,194 A | 12/1971 | Akiyoshi et al. | |
| 3,706,527 A | 12/1972 | Dobinson et al. | |
| 4,584,390 A | 4/1986 | Dieckelmann et al. | |
| 4,594,193 A * | 6/1986 | Regen | 554/81 |
| 4,906,775 A | 3/1990 | Kupper et al. | |
| 5,089,536 A | 2/1992 | Palazzotto | |
| 5,597,846 A * | 1/1997 | Sugimura et al. | 514/450 |
| 7,989,655 B2 | 8/2011 | Refvik et al. | |
| 2005/0080301 A1 | 4/2005 | Maughon et al. | |
| 2006/0000252 A1 | 1/2006 | Carstens et al. | |
| 2006/0041156 A1 | 2/2006 | Casper et al. | |
| 2009/0264669 A1 | 10/2009 | Upshaw | |

FOREIGN PATENT DOCUMENTS

WO    WO 2005-080325 A2    9/2005

OTHER PUBLICATIONS

CAS Registry No. 16410-16-5 (1984).*
International Search Report and Written Opinion, PCT/US09/041262, dated Aug. 25, 2009, 11 pages.

* cited by examiner

*Primary Examiner* — Joseph Kosack
(74) *Attorney, Agent, or Firm* — Merchant & Gould P.C.

(57) ABSTRACT

The application discloses thiol ester molecules and α-hydroxy thiol ester molecules having a thiol group located on one of the final two carbon atoms in a carbon chain or a terminal or α-hydroxyl groups, respectively. The disclosed thiol ester molecules and or α-hydroxyl thiol ester molecules may be made from unsaturated ester molecules having one or more terminal alkene groups. The disclosed techniques also provide methods for making unsaturated ester molecules having one or more terminal alkene groups by the metathesis of unsaturated esters having one or more internal carbon-carbon double bonds (e.g. natural source oils). The thiol ester molecules or α-hydroxy thiol ester molecule may be used in reactions with isocyanate monomers, epoxide monomer, or material having multiple alkene groups to make sealants, coatings, adhesives, and other products.

22 Claims, No Drawings

METHODS AND SYSTEMS FOR MAKING THIOL COMPOUNDS FROM TERMINAL OLEFINIC COMPOUNDS

CROSS REFERENCE TO RELATED APPLICATIONS

This application is a divisional application of co-pending U.S. patent application Ser. No. 12/427,467, filed on Apr. 21, 2009, which claims the benefit of the U.S. Provisional Patent Application Ser. No. 61/046,701, filed on Apr. 21, 2008, both of which are incorporated herein by reference in their entirety.

BACKGROUND

This section is intended to introduce the reader to aspects of art that may be related to aspects of the present techniques, which are described herein. This discussion is believed to be helpful in providing the reader with background information to facilitate a better understanding of the various aspects of the present techniques. Accordingly, it should be understood that these statements are to be read in this light, and not as admissions of prior art.

As chemical and petrochemical technologies have advanced, the products of these technologies have become increasingly prevalent in society. In particular, as techniques for bonding simple molecular building blocks into longer chains, termed polymers, have advanced, the polymer products, typically in the form of various plastics, have been increasingly incorporated into various everyday items. For example, polyurethane polymers and copolymers, made from the reactions of compounds containing hydroxyl groups with compounds containing isocyanate groups, may be used in retail and pharmaceutical packaging, furniture, household items, automobile components, adhesives, coatings, and various other consumer and industrial products.

The chemical industry strives to make these products with low-cost feedstocks that are in abundant supply. Currently, the main feedstocks for polyurethanes, and other plastics, are petrochemicals isolated from petroleum. However, as fossil fuels deplete over time, alternative sources are being sought as replacements for feedstocks. Further, the chemical industry continuously strives to produce products and use feedstocks that are environmentally friendly.

SUMMARY OF THE INVENTION

Disclosed herein are thiol ester composition comprising thiol ester molecules having ester linkages comprising a) a residue of a polyol and a carboxylic acid residues having i) at least 4 carbon atoms and ii) a thiol group located on a terminal carbon atom or a carbon atom adjacent to the terminal carbon atom. In an embodiment, the polyol of the residue of polyol was a diol, triol, or a tetraol. In some embodiments, the polyol of the residue of polyol was cyclohexane diol, trimethylol propane, glycerol, pentaerythritol, or combinations thereof. In other embodiments, the polyol of the residue of polyol was glycerol. In an embodiment, the carboxylic acid residues having a thiol group located on a terminal carbon atom or a carbon atom adjacent to the terminal carbon atom have from 10 to 11 carbon atoms. In some embodiments, the carboxylic acid residues having the thiol group located on the terminal carbon atom or the carbon atom adjacent to the terminal carbon atom have only 10 carbon atoms. In other embodiments, the carboxylic acid residues are substantially devoid of hydroxyl groups. In an embodiment, the thiol ester molecules have an average thiol sulfur content of 9 to 16 weight %. In an embodiment, the thiol ester molecules of the thiol ester composition has an average ratio of thiol groups located on a terminal carbon atom to thiol groups located on the carbon atom adjacent to the terminal carbon atom is greater than 5:1. In an embodiment, the average ratio of carboxylic acid residues having a thiol group located on a terminal carbon atom or a carbon atom adjacent to the terminal carbon atom to hydroxyl groups of the polyol of the residue of the polyol is greater than 0.70:1. In a particular embodiment, the thiol ester molecules of the thiol ester composition comprise have ester linkages comprising a) a polyol residue derived from cyclohexane diol, trimethylol propane, glycerol, pentaerythritol, or combinations thereof, and b) carboxylic acid residues having a thiol group located on a terminal carbon atom or a carbon atom adjacent to the terminal carbon atom having from 10 to 11 carbon atoms wherein thiol ester molecules have an average ratio of thiol groups located on a terminal carbon atom to thiol groups located on the carbon atom adjacent to the terminal carbon atom is greater than 5:1, and wherein the thiol ester molecules have an average thiol sulfur content of 9 to 16 weight %.

The thiol ester compositions comprising the thiol ester molecules having thiol groups located on a terminal carbon atom or on a carbon atom adjacent to the terminal carbon atom may be produced by a) contacting ethylene and natural source oil with a metathesis catalyst composition, b) forming unsaturated ester molecules having terminal carbon-carbon double bonds at metathesis conditions capable of forming the unsaturated ester molecules having terminal carbon-carbon double bonds, c) contacting the unsaturated ester molecules having terminal carbon-carbon double bonds and hydrogen sulfide, and d) forming the thiol ester composition comprising thiol ester molecules having the thiol group located on the terminal carbon atom at conditions capable of forming thiol ester molecules having the thiol group located on the terminal carbon. In an embodiment, wherein the metathesis catalyst composition comprises ruthenium carbene metathesis catalyst or a molybdenum carbene metathesis catalyst. In some embodiments, metathesis catalyst comprises dichloro(phenylmethylene) bis(tricyclohexylphosphine) ruthenium or 1,3-bis-(2,4,6-trimethylphenyl)-2-(imidazolidinylidene) (phenylmethylene) dichloro (tricyclohexylphosphine) ruthenium. In an embodiment, the metathesis conditions include a ethylene partial pressure ranging from 50 to 3000 psig and a temperature ranging from 5° C. to 100° C. In an embodiment, the natural source oil comprises a tallow oil, an olive oil, a peanut oil, a castor bean oil, a sunflower oil, a sesame oil, a poppy seed oil, a palm oil, an almond seed oil, a hazelnut oil, a rapeseed oil, a canola oil, a soybean oil, a corn oil, a safflower oil, a cottonseed oil, a camelina oil, a flaxseed oil, or a walnut oil, or any combination thereof. In some embodiments, the natural source oil is soybean oil, corn oil, canola oil, or castor bean oil. In other embodiments, the natural source oil is soybean oil.

Disclosed herein are thiol ester composition comprising thiol ester molecules having ester linkages comprising a) a residue of a polyol and a carboxylic acid residues having i) at least 4 carbon atoms and ii) a terminal α-hydroxy thiol group. In an embodiment, the polyol of the residue of polyol was a diol, triol, or a tetraol. In some embodiments, the polyol of the residue of polyol was cyclohexane diol, trimethylol propane, glycerol, pentaerythritol, or combinations thereof. In other embodiments, the polyol of the residue of the polyol is derived from glycerol. In an embodiment, the carboxylic acid residues having a terminal α-hydroxy thiol group have from 10 to 11 carbon atoms. In an embodiment, the carboxylic acid residues having a terminal α-hydroxy thiol group has only 10 carbon atoms. In an embodiment, the thiol ester molecules have an average thiol sulfur content of 9 to 16 weight %. In an embodiment, the average ratio of carboxylic acid residues having a terminal α-hydroxy thiol group to hydroxyl groups of the polyol of the residue of the polyol is greater than 0.70:1. In a particular embodiment, the thiol ester molecules of the thiol ester composition have ester linkages comprising a) a polyol residue derived from cyclohexane diol, trimethylol propane, glycerol, pentaerythritol, or combinations thereof, and b) a carboxylic acid residues having a terminal α-hydroxy thiol group having from 10 to 11 carbon atoms, and wherein the thiol ester molecules have an average thiol sulfur content of 9 to 16 weight %.

The thiol ester compositions comprising the thiol ester molecules having a terminal α-hydroxy thiol group may be produced by a) contacting ethylene and natural source oil with a metathesis catalyst composition, b) forming unsaturated estermolecules having terminal carbon-carbon double bonds at metathesis conditions capable of forming the unsaturated ester molecules having terminal carbon-carbon double bonds, c) contacting the unsaturated ester moleucles having terminal carbon-carbon double bonds and an oxygen containing compound, d) forming an epoxide ester molecules having terminal epoxide groups at conditions capable of forming epoxide ester molecules having terminal epoxide groups, e) contacting the epoxide ester molecules and hydrogen sulfide, and f) forming the thiol ester composition comprising thiol ester molecules having a terminal α-hydroxy thiol groups at conditions capable of forming thiol ester molecules. In an embodiment, the metathesis catalyst composition comprises ruthenium carbene metathesis catalyst or a molybdenum carbene metathesis catalyst. In some embodiments, the metathesis catalyst comprises dichloro(phenylmethylene) bis(tricyclohexylphosphine) ruthenium or 1,3-bis-(2,4,6-trimethylphenyl)-2-(imidazolidinylidene) (phenylmethylene) dichloro (tricyclohexylphosphine) ruthenium. In an embodiment, the metathesis conditions include a ethylene partial pressure ranging from 50 to 3000 psig and a temperature ranging from 5° C. to 100° C. In an embodiment, the natural source oil comprises a tallow oil, an olive oil, a peanut oil, a castor bean oil, a sunflower oil, a sesame oil, a poppy seed oil, a palm oil, an almond seed oil, a hazelnut oil, a rapeseed oil, a canola oil, a soybean oil, a corn oil, a safflower oil, a cottonseed oil, a camelina oil, a flaxseed oil, or a walnut oil, or any combination thereof. In some embodiments, the natural source oil is soybean oil, corn oil, canola oil, or castor bean oil. In other embodiments, the natural source oil is soybean oil.

DEFINITIONS

To define more clearly the terms used herein, the following definitions are provided. To the extent that any definition or usage provided by any document incorporated herein by reference conflicts with the definition or usage provided herein, the definition or usage provided herein controls.

While compositions and methods are described in terms of "comprising" various components or steps, the compositions and methods can also "consist essentially of" or "consist of" the various components or steps.

The terms "a," "an," and "the" are intended, unless specifically indicated otherwise, to include plural alternatives, e.g., at least one. For instance, the disclosure of "a thiol compound" is meant to encompass one, or mixtures or combinations of more than one, thiol compound, unless otherwise specified.

As used in this disclosure, the term "composition" indicates a system that includes molecules having the indicated features. The molecules may have a variety of structures, which have the indicated described herein. Further, a composition may have a variety of other components present, both intentional and unintentional, which do not have the indicated features and may or may not participate in the reactions described herein.

The term "hydrocarbyl group" is used herein in accordance with the definition specified by IUPAC: a univalent group formed by removing a hydrogen atom from a hydrocarbon (i.e., a group containing only carbon and hydrogen). Similarly, a "hydrocarbylene group" refers to a group formed by removing two hydrogen atoms from a hydrocarbon (either two hydrogen atoms from one carbon atom or one hydrogen atom from two different carbon atoms). A "hydrocarbon group" refers to a generalized group formed by removing one or more hydrogen atoms (as necessary for the particular group) from a hydrocarbon. A "hydrocarbyl group," "hydrocarbylene group," and "hydrocarbon group" can be acyclic or cyclic groups, and/or may be linear or branched. A "hydrocarbyl group," "hydrocarbylene group," and "hydrocarbon group" can include rings, ring systems, aromatic rings, and aromatic ring systems, which contain only carbon and hydrogen. "Hydrocarbyl groups," "hydrocarbylene groups," and "hydrocarbon groups" include, by way of example, aryl, arylene, alkyl, alkylene, cycloalkyl, cycloalkylene, aralkyl, aralkylene, and combinations of these groups, among others. Finally, it should be noted that the "hydrocarbyl group," "hydrocarbylene group," or "hydrocarbon group" definitions include "alkyl group," "alkylene group," and "alkyl groups," respectively, as members.

The term "alkyl group" is used herein in accordance with the definition specified by IUPAC: a univalent group formed by removing a hydrogen atom from an alkane. Similarly, an "alkylene group" refers to a group formed by removing two hydrogen atoms from an alkane (either two hydrogen atoms from one carbon atom or one hydrogen atom from two different carbon atoms). An "alkane group" refers to a generalized group formed by removing one or more hydrogen atoms (as necessary for the particular group) from a alkane. An "alkyl group," "alkylene group," and "alkane group" can be acyclic or cyclic groups, and/or may be linear or branched unless otherwise specified.

The term "organyl group" in used herein in accordance with the definition specified by IUPAC: an organic substituent group, regardless of functional type, having one free valence at a carbon atom. Similarly, an "organylene group" refers to an organic group, regardless of functional type, formed by removing two hydrogen atoms from an organic compound (either two hydrogen atoms from one carbon atom or one hydrogen atom from two different carbon atoms) and an "organic group" refers to a generalized organic group formed by removing one or more hydrogen atoms from an organic compound. Thus, an "organyl group," an "organylene group," and an "organic group" can contain organic functional group(s) and/or atom(s) other than carbon and hydrogen (i.e., an organic group that can comprise functional groups and/or atoms in addition to carbon and hydrogen). For instance, non-limiting examples of atoms other than carbon and hydrogen include halogens, oxygen, nitrogen, phosphorus, and the like. Non-limiting examples of functional groups include ethers, aldehydes, ketones, esters, sulfides, amines, and phosphines, and so forth. An "organyl group," "organylene group," or "organic group" may be aliphatic, inclusive of being cyclic or acyclic, or aromatic. "Organyl groups," "organylene groups," and "organic groups" also encompass heteroatom-containing rings, heteroatom-containing ring systems, heteroaromatic rings, and heteroaromatic ring systems. "Organyl groups," "organylene groups," and "organic groups" may be linear or branched unless otherwise specified. Finally, it should be noted that the "organyl group," "organylene group," or "organic group" definitions include "hydrocarbyl group," "hydrocarbylene group," "hydrocarbon group," respectively, and "alkyl group," "alkylene group," and "alkyl group," respectively, as members.

The term "natural" refers to materials obtained, by any method, from naturally occurring fruits, nuts, vegetables, plants and animals. As an example, "natural source oil" refers to source oils extracted, and optionally purified, from naturally occurring fruits, nuts, vegetables, plants and animals. Additionally, "unsaturated natural source oil" refers to unsaturated source oils extracted, and optionally purified, from naturally occurring fruits, nuts, vegetables, plants, and animals. It should be noted that "natural source oil" and "unsaturated natural source oil" also includes the respective oils extracted, and optionally purified, from genetically modified nuts, vegetables, plant, and animal sources.

The term "natural source raw material" refers to materials obtained by extraction, chemical breakdown, or chemical processing of "natural" materials. A non-limiting example includes natural source oils that can be extracted from naturally occurring fruits, nuts, vegetables, plants and animals. As another non-limiting example, glycerol and carboxylic acids or carboxylic acid esters, saturated or unsaturated, can be produced and isolated by the chemical processing of triglycerides extracted from naturally occurring fruits, nuts, vegetables, plants, and animals.

The term "thiol ester composition" refers to a composition that includes "thiol ester molecules." The thiol ester molecule has at least one thiol group and at least one ester group within the thiol ester molecule.

The term "hydroxy thiol ester composition" refers to a composition that includes "hydroxy thiol ester molecules." The hydroxy thiol ester molecule has at least one thiol group, at least one ester group, and at least one hydroxy or alcohol group within the hydroxy thiol ester molecule. The term "α-hydroxy thiol ester" refers to a composition that includes "α-hydroxy thiol ester molecules." The α-hydroxy thiol ester molecule has at least one thiol group, and one "α-hydroxy thiol group." The "α-hydroxy thiol group" has a hydroxy group and a thiol group on adjacent carbon atoms.

The term "unsaturated ester composition" refers to a composition that includes "unsaturated ester molecules." The unsaturated ester molecules have at least one ester group and at least one carbon-carbon double bond within the unsaturated ester molecule.

An ester molecule having an ester linkage comprising a residue of a polyol and a carboxylic acid residue describes esters formed via the combination of the hydroxy group(s) of the polyol and the carboxylic acid group of the carboxylic acid. It should be noted that this description does not mean that the step of forming the particular ester occurs via a reaction between the polyol and carboxylic acid, unless specifically recited as such. The description is only a method for describing the particular ester.

The term "polyol of the residue of the polyol" refers to the parent polyol that formed the residue of the polyol.

For any particular compound disclosed herein, any structure presented also encompasses all conformational isomers, regioisomers, and stereoisomers that may arise from a particular set of substituents, unless otherwise specified. The structure also encompasses all enantiomers, diastereomers, and other optical isomers whether in enantiomeric or racemic forms, as well as mixtures of stereoisomers, as would be recognized by a skilled artisan, unless otherwise specified.

All publications and patents mentioned herein are incorporated herein by reference for the purpose of describing and disclosing the constructs and methodologies described in the publications, which might be used in connection with the presently described invention. The publications discussed throughout the text are provided solely for their disclosure prior to the filing date of the present application. Nothing herein is to be construed as an admission that the inventors are not entitled to antedate such disclosure by virtue of prior invention.

DETAILED DESCRIPTION

The present techniques generally relate to thiol ester compositions comprising thiol ester molecules having a thiol group located on a terminal carbon atom or a thiol group located on a carbon atom adjacent to a terminal carbon atom. The present techniques, also relate to α-hydroxy thiol ester compositions comprising, or consisting essentially of, thiol ester molecules having a terminal α-hydroxy thiol group.

Generally, the techniques for forming thiol ester compositions comprising thiol ester molecules having a thiol group located on a terminal carbon atom or a thiol group located on a carbon atom adjacent to a terminal carbon atom include forming unsaturated ester compositions comprising, or consisting essentially of, unsaturated ester molecules having terminal carbon-carbon double bonds and reacting the unsaturated ester compositions comprising, or consisting essentially of, unsaturated ester molecules having terminal carbon-carbon double bonds to form the thiol ester compositions comprising thiol ester molecules having a thiol group located on a terminal carbon atom or a thiol group located on a carbon atom adjacent to a terminal carbon atom. The techniques for forming the α-hydroxy thiol ester compositions comprising, or consisting essentially of, thiol ester molecules having a terminal α-hydroxy thiol group generally include forming unsaturated ester compositions comprising, or consisting essentially of, unsaturated ester molecules having terminal carbon-carbon double bonds and reacting the unsaturated ester compositions comprising, or consisting essentially of, unsaturated ester molecules having terminal carbon-carbon double bonds with an oxygen containing compound to form an epoxide ester composition comprising, or consisting essentially of, epoxide ester molecules having terminal epoxide groups, and subsequently reacting the epoxide ester composition comprising, or consisting essentially of, epoxide ester molecules having terminal epoxide groups, with hydrogen sulfide to form an α-hydroxy thiol ester compositions comprising, or consisting essentially of, thiol ester molecules having a terminal α-hydroxy thiol group.

The thiol ester compositions comprising, or consisting essentially of, thiol ester molecules having a thiol group located on a terminal carbon atom or a thiol group located on a carbon atom adjacent to a terminal carbon atom and the α-hydroxy thiol ester compositions comprising, or consisting essentially of, thiol ester molecules having a terminal α-hydroxy thiol group may have advantages over previous materials. For example, the close proximity of the thiol groups to a terminal carbon atom may provide advantages in producing thiourethanes, polythiourethanes, epoxy compositions, and materials produced utilizing the thiol-ene reaction.

One or more specific embodiments of the compositions and techniques to produce the compositions are described herein. In an effort to provide a concise description of these embodiments, not all features of an actual implementation are described. It should be appreciated that in the development of any such actual implementation, as in any engineering or design project, numerous implementation-specific decisions must be made to achieve the developer's specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Thiol Ester Compositions

In an aspect, the present invention relates to thiol ester compositions comprising, or consisting essentially of, thiol ester molecules having a thiol groups located on terminal carbon atoms and/or thiol groups located on a carbon atom adjacent to a terminal carbon atom. In an aspect, thiol ester molecules may be described as comprising, consisting essentially of, one or more functional groups present in the thiol ester molecules of the thiol ester composition. Each of the functional groups that may be present in the thiol ester molecules are independently described herein and may be utilized in any combination to describe the thiol ester molecules.

The independent functional groups that can be utilized to describe the thiol ester molecules having a thiol groups located on terminal carbon atoms and/or thiol groups located on a carbon atom adjacent to a terminal carbon atom include: the location of the thiol group, the number of (or average number of) ester groups per thiol ester molecule, the number of (or average number of) thiol groups per thiol ester molecule, the ratio of (or average ratio of) thiol groups to ester groups, the number of (or average number of) carbon-carbon double bonds per thiol ester molecule, the average thiol sulfur content of the thiol ester molecules. In some embodiments, the thiol ester molecules have thiol groups located on terminal carbon atoms and/or thiol groups located on a carbon atom adjacent to a terminal carbon atom may be substantially devoid of hydroxyl groups.

The thiol ester molecules of the thiol ester compositions may be produced from any unsaturated ester having terminal double bonds, as described herein. It should be noted that the feedstock unsaturated esters having terminal double bonds may have multiple terminal double bonds and may contain many different unsaturated ester molecules having terminal double bonds. This fact, combined with carbon-carbon double bond reactivity and statistical probability, dictate that each thiol ester molecule having thiol groups located on terminal carbon atoms and/or thiol groups located on a carbon atom adjacent to a terminal carbon atom of the thiol ester molecule may not have the same number of functional groups, the same ratios of functional groups, and/or the same additional features. Thus, the number of functional group, ratios of functional groups, and/or additional features of the thiol ester molecules having thiol groups located on terminal carbon atoms and/or thiol groups located on a carbon atom adjacent to a terminal carbon atom of the thiol ester molecule may be referred to as an average per thiol ester molecule within the thiol ester composition.

In an embodiment, the thiol ester molecules having thiol groups located on terminal carbon atoms and/or thiol groups located on a carbon atom adjacent to a terminal carbon atom have at least 2 ester groups; alternatively at least 3 ester groups; or alternatively, at least 4 ester groups. In other embodiments, the thiol ester molecules having thiol groups located on terminal carbon atoms and/or thiol groups located on a carbon atom adjacent to a terminal carbon atom have from 2 to 8 ester; alternatively, 3 to 6 ester groups; alternatively, 3 to 4 ester groups; alternatively, only 3 ester groups; or alternatively, only 4 ester groups. In further embodiments, the thiol ester molecules having thiol groups located on terminal carbon atoms and/or thiol groups located on a carbon atom adjacent to a terminal carbon atom have an average of at least 2 ester groups per thiol ester molecule; alternatively, an average of at least 2.5 ester groups per thiol ester molecule; or alternatively, an average of at least 3 ester groups per thiol ester molecule. In yet further embodiments, the thiol esters have an average of from 2 to 8 ester groups per thiol ester molecule; alternatively, an average of from 2 to 7 ester groups per thiol ester molecule; alternatively, an average of from 2.5 to 5 ester groups per thiol ester molecule; or alternatively, an average of from 3 to 4 ester groups per thiol ester molecule. In yet other embodiments, the thiol ester molecules having thiol groups located on terminal carbon atoms and/or thiol groups located on a carbon atom adjacent to a terminal carbon atom have an average of about 3 ester groups per thiol ester molecule; or alternatively, an average of about 4 ester groups per thiol ester molecule.

In an embodiment, the thiol ester molecules having thiol groups located on terminal carbon atoms and/or thiol groups located on a carbon atom adjacent to a terminal carbon atom of the thiol ester composition have at least 2 thiol groups; alternatively, at least 3 thiol groups; or alternatively, at least 4 thiol groups. In other embodiments, the thiol ester molecules having thiol groups located on terminal carbon atoms and/or thiol groups located on a carbon atom adjacent to a terminal carbon atom have from 2 to 8 thiol groups; alternatively, 3 to 6 thiol groups; alternatively, 3 to 4 thiol groups; alternatively, only 3 thiol groups; or alternatively, only 4 thiol groups. In further embodiments, the thiol ester molecules having thiol groups located on terminal carbon atoms and/or thiol groups located on a carbon atom adjacent to a terminal carbon atom have an average of at least 1.5 thiol groups per thiol ester molecule; alternatively, an average of at least 2.5 thiol groups per thiol ester molecule; or alternatively, an average of at least 3 thiol groups per thiol ester molecule. In yet further embodiments, the thiol ester molecules have an average of from 1.5 to 8 thiol groups per thiol ester molecule; alternatively, an average of from 2 to 7 thiol groups per thiol ester molecule; alternatively, an average of from 2.5 to 5 thiol groups per thiol ester molecule; or alternatively, an average of from 3 to 4 thiol groups per thiol ester molecule. In yet other embodiments, the thiol ester molecules having thiol groups located on terminal carbon atoms and/or thiol groups located on a carbon atom adjacent to a terminal carbon atom have an average of about 3 thiol groups per thiol ester molecule; or alternatively, an average of about 4 thiol groups per thiol ester molecule.

In an embodiment, the thiol group, of thiol ester molecules, may be located on a terminal thiol atom, located on a carbon adjacent to a terminal carbon atom, or a mixture thereof. In some embodiments, the thiol group of the thiol ester molecule may be located on a terminal carbon atom group; alternatively, the thiol group of the thiol ester molecule may be located on the carbon atom adjacent to a terminal carbon atom.

Generally, the location of the thiol group within the thiol ester molecule may depend upon the particular method utilized to produce it. For example, when reacting unsaturated esters having a terminal carbon-carbon double bond located at a terminal position, it may be possible to choose reaction conditions to produce a thiol ester molecules having a thiol group located on a terminal carbon atom (forming a primary thiol group) or a thiol group located on the carbon atom adjacent to the terminal carbon atom (forming a secondary or tertiary thiol group). It should be noted that in further reactions, primary, secondary, and tertiary thiol groups may have different reactivities. Consequently, it may be desirable to control the ratio of (or average ratio of) thiol groups located on a terminal carbon atom to thiol group located on the carbon atom adjacent to the terminal carbon atom. In some embodiments, the average ratio of thiol groups located on a terminal carbon atom to thiol groups located on the carbon atom adjacent to the terminal carbon atom is greater than 5:1; alternatively, greater than 8:1; or alternatively, greater than 10:1. In other embodiments the average ratio of thiol groups located on a terminal carbon atom to thiol groups located on the carbon atom adjacent to the terminal carbon atom is greater than 1:5; alternatively, greater than 1:8; or alternatively, greater than 1:10.

In an embodiment, the thiol ester molecules may contain carbon-carbon double bonds. These carbon-carbon double bonds may result from incomplete conversion of the feedstock during the reaction with hydrogen sulfide described herein. In some embodiments, the average ratio of carbon-carbon double bonds to thiol groups is less than 1:5; alternatively, less than 1:7; or alternatively, less than 1:10.

In another aspect, the thiol ester molecules within the thiol ester compositions may be described as having ester linkages comprising a residue of a polyol and a carboxylic acid residue having a thiol group. Additional features of the residue of the polyol and carboxylic acid residue having a thiol group are independently described herein and may be utilized in any combination to further describe the thiol ester molecules.

The thiol ester molecules described as having ester linkages comprising a residue of a polyol and a carboxylic acid residue having a thiol group may be produced from any unsaturated ester, as described herein. It should be noted that the feedstock unsaturated esters may have multiple double bonds and may contain many different unsaturated ester molecules. This fact, combined with carbon-carbon double bond reactivity and statistical probability, dictate that each thiol ester molecule having ester linkages comprising a residue of a polyol and a carboxylic acid residue having a thiol group may not have the same structure. Thus, particular features of the thiol ester molecules having ester linkages comprising a residue of a polyol and a carboxylic acid residue having a thiol group may be described as an average per thiol ester molecule.

In an embodiment, the thiol ester molecule having ester linkages comprises a residue of a polyol and a carboxylic acid residues having a thiol group. The residue of the polyol and the carboxylic acid residue having a thiol group are independent elements of thiol ester molecules having ester linkage. Consequently, the features of the residue of the polyol and the carboxylic acid having a thiol group are independently described herein and may be used in any combination to describe the thiol ester molecules having ester linkages may comprise residue of a polyol and at least two carboxylic acid residues having a thiol group.

The carboxylic acid residue having a thiol group may be further described by its structural features. These structural features are independently described herein and may be utilized in any combination to describe the carboxylic acid residue of the thiol ester molecules having ester linkages comprising a residue of a polyol and carboxylic acid residues having a thiol group.

In an embodiment, the carboxylic acid residue having the thiol group is linear. In another embodiment, the carboxylic acid residue having the thiol group is branched.

In an embodiment, the thiol group of the carboxylic acid residue may be located on a terminal carbon atom (a carboxylic acid residue having a thiol group located on a terminal carbon atom), located on a carbon adjacent to a terminal carbon atom (a carboxylic acid residue having a thiol group located on a carbon atom adjacent to a terminal carbon atom), or a mixture thereof. In some embodiments, the thiol group of the carboxylic acid residue may be located on a terminal carbon atom group; alternatively, the thiol group of the carboxylic acid residue may be located on the carbon atom adjacent to a terminal carbon atom. In an embodiment, the average ratio of carboxylic acid residues having thiol groups located on a terminal carbon atom to carboxylic acid residues having thiol groups located on the carbon atom adjacent to the terminal carbon atom is greater than 5:1; alternatively, greater than 8:1; or alternatively, greater than 10:1. In other embodiments the average ratio of carboxylic acid residues having thiol groups located on a terminal carbon atom to carboxylic acid residues having thiol groups located on the carbon atom adjacent to the terminal carbon atom is greater than 1:5; alternatively, greater than 1:8; or alternatively, greater than 1:10.

In an embodiment, the carboxylic acid residue having a thiol group located on a terminal carbon atom and/or thiol group located on a carbon atom adjacent to a terminal carbon atom may have at least 4 carbon atoms; alternatively, at least 6 carbon atoms; or alternatively, at least 8 carbon atoms. In some embodiments, the carboxylic acid residue having a thiol group located on a located on a terminal carbon atom and/or thiol group located on a carbon atom adjacent to a terminal carbon atom may have from 4 to 20 carbon atoms; alternatively, from 6 to 18 carbon atoms; alternatively, from 8 to 14 carbon atoms; alternatively, from 10 to 11 carbon atoms; alternatively, only 10 carbon atoms; or alternatively, only 11 carbon atoms. In an embodiment, the carboxylic acid residue having a thiol group located on a located on a terminal carbon atom and/or thiol group located on a carbon atom adjacent to a terminal carbon atom may have an average of at least 4 carbon atoms; alternatively, at least 6 carbon atoms; or alternatively, at least 8 carbon atoms. In some embodiments, the carboxylic acid residue having a thiol group located on a located on a terminal carbon atom and/or thiol group located on a carbon atom adjacent to a terminal carbon atom may have an average of 4 to 20 carbon atoms; alternatively, of 6 to 18 carbon atoms; alternatively, of 8 to 14 carbon atoms; alternatively, of 10 to 11 carbon atoms; alternatively, of about 10 carbon atoms; or alternatively, of about 11 carbon atoms.

In an embodiment, the carboxylic acid residue having a thiol group is substantially devoid of hydroxyl group. In further embodiments, the carboxylic acid residue having a thiol group is devoid of hydroxyl groups. In yet other embodiments, the carboxylic acid residue having a thiol group is substantially devoid of other functional groups. In further embodiments, the carboxylic acid residue having a thiol group is devoid of other functional groups (i.e. outside of the thiol group located on a terminal carbon atom or the thiol group located on a carbon atom adjacent to a terminal carbon atom and the carbonyl group forming the ester linkage, the carboxylic acid contains only carbon and hydrogen).

In an embodiment, the carboxylic acid residues having a thiol group located on a terminal carbon atom may have Structure CRT 1

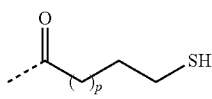

CRT 1 wherein p may be positive integer ranging from 1 to 17; alternatively from 3 to 15; alternatively, from 5 to 11; or alternatively 7 to 8. In some embodiments, p may be 7 or alternatively 8. In other embodiments, p may represent an average number (whole or fractional) of carbon atom ranging from 1 to 17; alternatively from 3 to 15; alternatively, from 5 to 11; alternatively 7 to 8; alternatively about 7; or alternatively, about 8. Within the carboxylic acid residue structure CRT 1 the dashed line is the bond to the oxygen atom of the ester linkage.

In an embodiment, the carboxylic acid residues having a thiol group located on a carbon atom adjacent to a terminal carbon atom may have Structure CRT 2

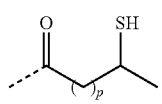

CRT 2 wherein p may be positive integer ranging from 1 to 17; alternatively from 3 to 15; alternatively, from 5 to 11; or alternatively 7 to 8. In some embodiments, p may be 7 or alternatively 8. In other embodiments, p may represent an average number (whole or fractional) of carbon atom ranging from 1 to 17; alternatively from 3 to 15; alternatively, from 5 to 11; alternatively 7 to 8; alternatively about 7; or alternatively, about 8. Within the carboxylic acid residue structure CRT 2 the dashed line is the bond to the oxygen atom of the ester linkage.

Suitable the carboxylic acid residues having a thiol group located on the terminal carbon atom include a 4-thiol butanoic acid residue, a 5-thiol pentanoic acid residue, a 6-thiol hexanoic acid residue, a 7-thiol heptanoic acid residue, a 8-thiol octanoic acid residue, a 9-thiol nonanoic acid residue, a 10-thiol decanoic acid residue, a 11-thiol undecanoic acid residue, a 12-thiol dodecanoic acid residue, a 13-thiol tridecanoic acid residue, a 14-thiol tetradecanoic acid residue, a 15-thiol pentadecanoic acid residue, a 16-thiol hexadecanoic acid residue, a 17-thiol heptadecanoic acid residue, a 18-thiol octadecanoic acid residue, a 19-thiol nonadecanoic acid residue, a 20-thiol eicosene, or any combination thereof. In some embodiments, the carboxylic acid residues having a thiol group located on the terminal carbon atom include a 6-thiol hexanoic acid residue, a 7-thiol heptanoic acid residue, a 8-thiol octanoic acid residue, a 9-thiol nonanoic acid residue, a 10-thiol decanoic acid residue, a 11-thiol undecanoic acid residue, a 12-thiol dodecanoic acid residue, a 13-thiol tridecanoic acid residue, a 14-thiol tetradecanoic acid residue, a 15-thiol pentadecanoic acid residue, a 16-thiol hexadecanoic acid residue, a 17-thiol heptadecanoic acid residue, a 18-thiol octadecanoic acid residue, or any combination thereof; alternatively, a 8-thiol octanoic acid residue, a 9-thiol nonanoic acid residue, a 10-thiol decanoic acid residue, a 11-thiol undecanoic acid residue, a 12-thiol dodecanoic acid residue, a 13-thiol tridecanoic acid residue, a 14-thiol tetradecanoic acid residue, or any combination thereof; or alternatively, a 10-thiol decanoic acid residue, a 11-undecanoic acid residue, or any combination thereof. In other embodiment, the carboxylic acid residues having a thiol group located on the terminal carbon atom may be a 6-thiol hexanoic acid residue; alternatively, a 7-thiol heptanoic acid residue; alternatively, a 8-thiol octanoic acid residue; alternatively, a 9-thiol nonanoic acid residue; alternatively, a 10-thiol decanoic acid residue; alternatively, a 11-thiol undecanoic acid residue; alternatively, a 12-thiol dodecanoic acid residue; alternatively, a 13-thiol tridecanoic acid residue; alternatively, a 14-thiol tetradecanoic acid residue; alternatively, a 15-thiol pentadecanoic acid residue; alternatively, a 16-thiol hexadecanoic acid residue; alternatively, a 17-thiol heptadecanoic acid residue; or alternatively, a 18-thiol octadecanoic acid residue.

Suitable carboxylic acid residues having a thiol group adjacent to the terminal carbon atom include a 3-thiol butanoic acid residue, a 4-thiol pentanoic acid residue, a 5-thiol hexanoic acid residue, a 6-thiol heptanoic acid residue, a 7-thiol octanoic acid residue, a 8-thiol nonanoic acid residue, a 9-thiol decanoic acid residue, a 10-thiol undecanoic acid residue, a 11-thiol dodecanoic acid residue, a 12-thiol tridecanoic acid residue, a 13-thiol tetradecanoic acid residue, a 14-thiol pentadecanoic acid residue, a 15-thiol hexadecanoic acid residue, a 16-thiol heptadecanoic acid residue, a 17-thiol octadecanoic acid residue, a 18-thiol nonadecanoic acid residue, a 19-thiol eicosene, or any combination thereof. In some embodiments, the carboxylic acid residues having a thiol group located on the terminal carbon atom include a 5-thiol hexanoic acid residue, a 6-thiol heptanoic acid residue, a 7-thiol octanoic acid residue, a 8-thiol nonanoic acid residue, a 9-thiol decanoic acid residue, a 10-thiol undecanoic acid residue, a 11-thiol dodecanoic acid residue, a 12-thiol tridecanoic acid residue, a 13-thiol tetradecanoic acid residue, a 14-thiol pentadecanoic acid residue, a 15-thiol hexadecanoic acid residue, a 16-thiol heptadecanoic acid residue, a 17-thiol octadecanoic acid residue, or any combination thereof; alternatively, a 7-thiol octanoic acid residue, a 8-thiol nonanoic acid residue, a 9-thiol decanoic acid residue, a 10-thiol undecanoic acid residue, a 11-thiol undecanoic acid residue, a 12-thiol tridecanoic acid residue, a 13-thiol tetradecanoic acid residue, or any combination thereof; or alternatively, a 9-thiol decanoic acid residue, a 10-undecanoic acid residue, or any combination thereof. In other embodiment, the carboxylic acid residues having a thiol group located on the terminal carbon atom may be a 5-thiol hexanoic acid residue; alternatively, a 6-thiol heptanoic acid residue; alternatively, a 7-thiol octanoic acid residue; alternatively, a 8-thiol nonanoic acid residue; alternatively, a 9-thiol decanoic acid residue; alternatively, a 10-thiol undecanoic acid residue; alternatively, a 11-thiol dodecanoic acid residue; alternatively, a 12-thiol tridecanoic acid residue; alternatively, a 13-thiol tetradecanoic acid residue; alternatively, a 14-thiol pentadecanoic acid residue; alternatively, a 15-thiol hexadecanoic acid residue; alternatively, a 16-thiol heptadecanoic acid residue; or alternatively, a 17-thiol octadecanoic acid residue.

The residue of the polyol may be further described by its structural features. These structural features are independently described herein and may be utilized in any combination to describe the residue of the polyol of the thiol ester molecules having ester linkages comprising, or consisting essentially of a residue of a polyol and carboxylic acid residues having a thiol group located on a terminal carbon atom and/or thiol group located on a carbon atom adjacent to a terminal carbon atom.

In an embodiment, residue of the polyol may have 2 to 20 carbon atoms. In some embodiments, the residue of the polyol may have 2 to 12 carbon atoms; alternatively, 2 to 8 carbon atoms; or alternatively, 2 to 5 carbon atoms. In some embodiments, the polyol of the residue of the polyol may have had 2 to 8 hydroxyl group; alternatively, 3 to 6 hydroxyl groups; alternatively, 2 to 4 hydroxyl groups; alternatively, 4 to 8 hydroxyl groups; alternatively, only 3 hydroxyl groups; alternatively, only 4 hydroxyl groups; alternatively, only 5 hydroxyl groups; or alternatively, only 6 hydroxyl groups.

In other embodiments, the residue of the polyol may be a residue of a mixture of polyols. In such an instance the residue of the polyol may have an average of 2 to 20 carbon atoms per polyol molecule; alternatively, an average of 2 to 12 carbon atoms per polyol molecule; alternatively, an average of 2 to 8 carbon atoms per polyol molecule; or alternatively, an average of 2 to 5 carbon atoms per polyol molecule. Further, the mixture of polyols of the residues of the polyols may have had an average of at least 2.5 hydroxyl groups per polyol molecule; alternatively, 2.5 to 8 hydroxyl groups per polyol molecule; alternatively, an average of 2 to 6 hydroxyl groups per polyol molecule; alternatively, an average of 2.5 to 5 hydroxyl groups per polyol molecule; alternatively, an average of 2.5 to 4.5 hydroxyl group per polyol molecule; alternatively, an average of 2.5 to 3.5 hydroxyl group per polyol molecule; alternatively, an average of 3 to 4 hydroxyl group per polyol molecule; alternatively, an average of about 3 hydroxyl groups per polyol molecule; alternatively, an average of about 4 hydroxyl groups per polyol molecule; alternatively, an average of about 5 hydroxyl groups per polyol molecule; or alternatively an average of about 6 hydroxy groups per polyol molecule.

In an embodiment, the polyol that formed the residue of the polyol or mixture of polyols that formed the residues of the polyols may have had a molecular weight or average molecular weight less than 300. In other embodiments, the polyol that formed the residue of the polyol or mixture of polyols that formed the residues of the polyols may have had a molecular weight or average molecular weight less than 250; alternatively less than 200; alternatively, less than 150; or alternatively, less than 100.

In an embodiments, the polyol that formed the residue of the polyol was a diol, triol, a tetraol, pentaol, hexaol, or combination thereof; alternatively a diol, triol, tetraol or combination thereof; or alternatively, a triol, tetraol or combination thereof. In some embodiments, the polyol that formed the residue of the polyol was a diol; alternatively, a triol; alternatively, a tetraol; alternatively, a pentaol; or alternatively, a hexaol. Suitable polyols that may form the residue of the polyol include ethane diol, propanediol, butanediol, pentanediol, hexanediol, cyclohexane diol, phenylethane diol, cyclohexanedimethanol, dimethyolpropane, benzenedimethanol, cyclohexanetriol, trihydroxybenzene, trimethyolethane, trimethylolpropane, trimethylolbutane, glycerol, pentaerythritol, sorbitol, or any combination thereof; alternatively, cyclohexane diol, trimethylol propane, glycerol, pentaerythritol, or combinations thereof; alternatively, glycerol, pentaerythritol, or combinations thereof. In some embodiments, the polyol that may form the residue of the polyol include 1,2-ethanediol, 1,3-propanediol, 1,4-butanediol, 1,5-pentanediol, 1,6-hexanediol, dimethylolpropane, neopentyl glycol, 2-propyl-2-ethyl-1,3-propanediol, 1,2-propanediol, 1,2-butanediol, 1,3-butanediol, 1,4-butanediol, diethylene glycol, triethylene glycol, polyethylene glycol, dipropylene glycol, tripropylene glycol, polypropylene glycol, 1,1-cyclohexanedimethanol, 1,2-cyclohexanedimethanol, 1,3-cyclohexanedimethanol, 1,4-cyclohexanedimethanol, 1,3-dioxane-5,5-dimethanol, 1-phenyl-1,2-ethanediol, trimethylolpropane, trimethylolethane, trimethylolbutane, glycerol, 1,2,5-hexanetriol, pentaerythritol, ditrimethylolpropane, diglycerol, ditrimethylolethane, 1,3,5-trihydroxybenzene, 1,2-benzenedimethanol, 1,3-benzenedimethanol, 1,4-benzenedimethanol, 1-phenyl-1,2-ethanediol, sorbitol, or any combination thereof. In other embodiments, the polyol that may be used as the polyol residue may be trimethylolpropane, glycerol, pentaerythritol, or combinations thereof; alternatively, trimethylolpropane; alternatively, glycerol; alternatively, pentaerythritol; or alternatively sorbitol.

It should be appreciated that not all of the hydroxyl groups of the polyol that form the residue of the polyol may form ester linkages. In some instances some of the hydroxyl groups may not form ester linkages and may remain as hydroxyl group. In an embodiment, greater than 80, 85, 90, 95 percent of all hydroxyl groups of the residue of the polyol form ester linkages. In other embodiments, substantially all of the hydroxyl groups of the polyol, which forms the residue of a polyol forming linkages with a carboxylic acid having a thiol group located on a terminal thiol atom, located on a carbon adjacent to a terminal carbon atom, or a combination thereof, forms ester linkages. In yet other embodiments, the thiol ester molecules having ester linkages comprising a residue of a polyol and carboxylic acid residues having a thiol group are substantially devoid of hydroxy groups derived from the polyol. In some embodiments, the average ratio of carboxylic acid residues having a thiol group located on a terminal carbon atom or a carbon atom adjacent to the terminal carbon atom to hydroxyl groups of the polyol of the residue of the polyol is greater than 0.70:1; alternatively, greater than 0.75:1; alternatively, greater than 0.80:1; alternatively, greater than 0.85:1; alternatively, greater than 0.90:1; alternatively, greater than 0.95:1.

It will be appreciated that not all of the ester linkages comprising the residue of the polyol may comprise carboxylic acid residues having a thiol group located on a terminal carbon atom and/or a thiol group located on a carbon atom adjacent to the terminal carbon atom. For example, some of the ester linkages may comprise a residue of the polyol and carboxylic acid residue having a terminal carbon-carbon double bond resulting from incomplete conversion of the feedstock during the reaction with hydrogen sulfide described herein. In such an instance, the thiol ester molecules having ester linkages comprising a residue of a polyol and a carboxylic acid residues having a thiol group may be further defined by the average ratio of carboxylic acid residues having a carbon-carbon double bond to carboxylic acid residues having a thiol group. In an embodiment, average ratio of carboxylic acid residues having a carbon-carbon double bond to carboxylic acid residues having a thiol group may be less than 1:5; alternatively, less than 1:7; or alternatively, less than 1:10. Additionally or alternatively, the feedstock used to produce the thiol ester molecules may contain an ester linkage with saturated carboxylic acid that can not be thiolated using the methods described herein and/or unsaturated carboxylic acid residue that were not thiolated. Considering this situation, in some embodiments, greater than 75, 80, 85, or 90 percent of all ester linkages comprising the residue of the polyol comprise carboxylic acid residues having the thiol group located on a terminal carbon atom and/or a thiol group located on a carbon atom adjacent to the terminal carbon atom.

In an embodiment, the thiol ester molecules, whether described as having particular functional groups or as thiol ester molecules having ester linkages comprising a residue of a polyol and carboxylic acid residue having a thiol group located on a terminal carbon atom and/or thiol group located on a carbon atom adjacent to a terminal carbon atom, may have an average ratio of thiol groups to ester groups in the thiol ester molecules of less than 1.15:1; alternatively, less than 1.1:1; or alternatively, less than 1.05:1. In some embodiments, the thiol ester molecules, whether described as having particular functional groups or as thiol ester molecules having ester linkages comprising a polyol residue and carboxylic acid residues having a thiol group located on a terminal carbon atom and/or thiol group located on a carbon atom adjacent to a terminal carbon atom, may have an average ratio of thiol groups to ester groups in the thiol ester molecules that ranges from 0.75:1 to 1.15:1; alternatively, ranges from 0.85:1 to 1.1:1; or alternatively, ranges from 0.90:1 to 1.05:1. In other embodiments, the thiol ester molecules, whether described as having particular functional groups or as thiol ester molecules having ester linkages comprising a polyol residue and carboxylic acid residues having a thiol group located on a terminal carbon atom and/or thiol group located on a carbon atom adjacent to a terminal carbon atom, may have an average ratio of thiol groups to ester groups in the thiol ester molecules of about 1:1.

In some embodiments, the thiol ester molecules, whether described as having particular functional groups or as thiol ester molecules having ester linkages comprising a polyol residue and carboxylic acid residues having a thiol group located on a terminal carbon atom and/or thiol group located on a carbon atom adjacent to a terminal carbon atom, may have an average thiol sulfur content of 5 to 20 weight percent; alternatively, 7 to 18 weight percent; alternatively, 9 to 16 weight percent. In other embodiment, the thiol ester molecules, whether described as having particular functional groups or as thiol ester molecules having ester linkages comprising a polyol residue and carboxylic acid residues having a thiol group located on a terminal carbon atom and/or thiol group located on a carbon atom adjacent to a terminal carbon atom, may have a thiol equivalent weight of 140 to 500 grams; alternatively, 170 to 400 grams; alternatively, 200 to 350 grams.

α-Hydroxy Thiol Ester Compositions

In an aspect, the present invention relates to α-hydroxy thiol ester compositions comprising, or consisting essentially of, α-hydroxy thiol ester molecules having terminal α-hydroxy thiol groups. The α-hydroxy thiol ester molecules may be described as comprising, consisting essentially of, one or more functional group present in the α-hydroxy thiol ester molecules of the α-hydroxy thiol ester composition. Each of the functional groups that may be present in the α-hydroxy thiol ester molecules thiol groups are independently described herein and may be utilized in any combination to described the α-hydroxy thiol ester molecules.

The independent functional groups that can be utilized to describe the α-hydroxy thiol ester molecules having terminal α-hydroxy thiol groups include: the number of (or average number of) ester groups per α-hydroxy thiol ester molecule, the number of (or average number of) terminal α-hydroxy thiol groups per α-hydroxy thiol ester molecule, the ratio of (or average ratio of) terminal α-hydroxy thiol groups to ester groups per α-hydroxy thiol ester molecule, the number of (or average number of) unreacted carbon-carbon double bonds per α-hydroxy thiol ester molecule, the number of (or average number of) unreacted epoxide per α-hydroxy thiol ester molecule, and the average thiol sulfur content of the α-hydroxy thiol ester molecules.

The α-hydroxy thiol ester molecules having terminal α-hydroxy thiol groups of the α-hydroxy thiol ester compositions may be produced from any epoxidized unsaturated ester composition (epoxide ester composition) comprising epoxidized unsaturated ester molecules (epoxide ester molecules) having terminal epoxide groups described herein. It should be noted that the feedstock epoxidized unsaturated esters may have multiple epoxide and may contain many different epoxidized unsaturated ester molecules. This fact, combined with epoxide group reactivity and statistical probability, dictate that each α-hydroxy thiol ester molecule having terminal α-hydroxy thiol groups of the α-hydroxy thiol ester composition may not have the same number of functional groups, the same ratios of functional groups, and/or the same additional features. Thus, the number of functional group, ratios of functional groups, and/or additional features of the α-hydroxy thiol ester molecules of the α-hydroxy thiol ester composition may be referred to as an average per α-hydroxy thiol ester molecules within the α-hydroxy thiol ester composition.

In an embodiment, the α-hydroxy thiol ester molecules having terminal α-hydroxy thiol groups may have at least 2 ester groups; alternatively at least 3 ester groups; or alternatively, at least 4 ester groups. In other embodiments, the α-hydroxy thiol ester molecules having terminal α-hydroxy thiol groups may have from 2 to 8 ester groups; alternatively, 3 to 6 ester groups; alternatively, 3 to 4 ester groups; alternatively, only 3 ester groups; or alternatively, only 4 ester groups. In further embodiments, the α-hydroxy thiol ester molecules having terminal α-hydroxy thiol groups may have an average of at least 2 ester groups per α-hydroxy thiol ester molecule; alternatively, an average of at least 2.5 ester groups per α-hydroxy thiol ester molecule; or alternatively, an average of at least 3 ester groups per α-hydroxy thiol ester molecule. In yet further embodiments, the α-hydroxy thiol esters having terminal α-hydroxy thiol groups may have an average of from 2 to 8 ester groups per α-hydroxy thiol ester molecule; alternatively, an average of from 2 to 7 ester groups per α-hydroxy thiol ester molecule; alternatively, an average of from 2.5 to 5 ester groups per α-hydroxy thiol ester molecule; or alternatively, an average of from 3 to 4 ester groups per α-hydroxy thiol ester molecule. In yet other embodiments, the α-hydroxy thiol ester molecules having terminal α-hydroxy thiol groups may have an average of about 3 ester groups per α-hydroxy thiol ester molecule; or alternatively, an average of about 4 ester groups per α-hydroxy thiol ester molecule.

In an embodiment, the α-hydroxy thiol ester molecules of the α-hydroxy thiol ester composition have at least 2 terminal α-hydroxy thiol groups; alternatively, at least 3 terminal α-hydroxy thiol groups; or alternatively, at least 4 terminal α-hydroxy thiol groups. In other embodiments, the α-hydroxy thiol ester molecules have from 2 to 8 terminal α-hydroxy thiol groups; alternatively, 3 to 6 terminal α-hydroxy thiol groups; alternatively, 3 to 4 terminal α-hydroxy thiol groups; alternatively, only 3 terminal α-hydroxy thiol groups; or alternatively, only 4 terminal α-hydroxy thiol groups. In further embodiments, the α-hydroxy thiol ester molecules have an average of at least 1.5 terminal α-hydroxy thiol groups per α-hydroxy thiol ester molecules; alternatively, an average of at least 2.5 terminal α-hydroxy thiol groups per α-hydroxy thiol ester molecule; or alternatively, an average of at least 3 terminal α-hydroxy thiol groups per α-hydroxy thiol ester molecule. In yet further embodiments, the α-hydroxy thiol ester molecules have an average of from 1.5 to 8 terminal α-hydroxy thiol groups per α-hydroxy thiol ester molecule; alternatively, an average of from 2 to 7 terminal α-hydroxy thiol groups per α-hydroxy thiol ester molecule; alternatively, an average of from 2.5 to 5 terminal α-hydroxy thiol groups per α-hydroxy thiol ester molecule; or alternatively, an average of from 3 to 4 terminal α-hydroxy thiol groups per α-hydroxy thiol ester molecule. In yet other embodiments, the α-hydroxy thiol ester molecules have an average of about 3 terminal α-hydroxy thiol groups per α-hydroxy thiol ester molecule; or alternatively, an average of about 4 terminal α-hydroxy thiol groups per α-hydroxy thiol ester molecule.

Unless otherwise specified, either the thiol group or the hydroxyl group of the α-hydroxy thiol group may be located on the terminal carbon atom. In an embodiment, the thiol group of the terminal α-hydroxy thiol group may be located on the terminal carbon atom. In other embodiments, the hydroxyl group of the terminal α-hydroxy thiol group may be located on the terminal carbon atom.

In an embodiment, the α-hydroxy thiol ester molecules having terminal α-hydroxy thiol groups may contain epoxide groups. These epoxide groups may result from incomplete conversion of the feedstock during the reaction with hydrogen sulfide described herein. In some embodiments, the average ratio of epoxide to α-hydroxy thiol groups is less than 1:5; alternatively, less than 1:7; or alternatively, less than 1:10.

In another aspect, the α-hydroxy thiol ester molecules within the α-hydroxy thiol ester compositions may be described as having ester linkages comprising a residue of a polyol and a carboxylic acid residue having a terminal α-hydroxy thiol group. Additional features of the residue of the polyol and carboxylic acid residue having a terminal α-hydroxy thiol group are independently described herein and may be utilized in any combination to further describe the α-hydroxy thiol ester molecules.

The α-hydroxy thiol ester molecules described as having ester linkages comprising a residue of a polyol and a carboxylic acid residue having a terminal α-hydroxy thiol group may be produced from any epoxidized ester molecule having a terminal epoxide groups described herein. It should be noted that the feedstock epoxized ester molecules may have multiple epoxide groups and may contain many different epoxidized ester molecules. This fact, combined with epoxide reactivity and statistical probability, dictate that each α-hydroxy thiol ester molecule having ester linkages comprising a residue of a polyol and a carboxylic acid residue having a terminal α-hydroxy thiol group may not have the same structure. Thus, particular features of the α-hydroxy thiol ester molecules having ester linkages comprising a residue of a polyol and a carboxylic acid residue having a terminal α-hydroxy thiol group may be described as an average per α-hydroxy thiol ester molecule.

In an embodiment, the α-hydroxy thiol ester molecules having ester linkages comprise a residue of a polyol and carboxylic acid residues having a terminal α-hydroxy thiol group. The residue of the polyol and the carboxylic acid residue having a terminal α-hydroxy thiol group are independent elements of α-hydroxy thiol ester molecules having ester linkages. Consequently, the features of the residue of the polyol and the carboxylic acid having a terminal α-hydroxy thiol group are independently described herein and may be used in any combination to describe the α-hydroxy thiol ester molecules having ester linkages comprising a residue of a polyol and at least two carboxylic acid residues having a terminal α-hydroxy thiol group.

The carboxylic acid residue having a terminal α-hydroxy thiol group may be further described by its structural features. These structural features are independently described herein and may be utilized in any combination to describe the carboxylic acid residue of the α-hydroxy thiol ester molecules having ester linkages comprising a residue of a polyol and carboxylic acid residues having a terminal α-hydroxy thiol group.

In an embodiment, the carboxylic acid residue having the terminal α-hydroxy thiol group is linear. In another embodiment, the carboxylic acid residue having the terminal α-hydroxy thiol group is branched.

Unless otherwise specified, either the thiol group or the hydroxy group of the α-hydroxy thiol group within the carboxylic acid residue having a terminal α-hydroxy thiol group may be located on the terminal carbon atom. In an embodiment, the thiol group of the α-hydroxy thiol group within the carboxylic acid residue having a terminal α-hydroxy thiol group may be located on the terminal carbon atom. In other embodiments, the hydroxyl group of the α-hydroxy thiol group within the carboxylic acid residue having a terminal α-hydroxy thiol group may be located on the terminal carbon atom.

In an embodiment, the carboxylic acid residue having a terminal α-hydroxy thiol group may have at least 4 carbon atoms; alternatively, at least 6 carbon atoms; or alternatively, at least 8 carbon atoms. In some embodiments, the carboxylic acid residue having a terminal α-hydroxy thiol group may have from 4 to 20 carbon atoms; alternatively, from 6 to 18 carbon atoms; alternatively, from 8 to 14 carbon atoms; alternatively, from 10 to 11 carbon atoms; alternatively, only 10 carbon atoms; or alternatively, only 11 carbon atoms. In an embodiment, the carboxylic acid residue a terminal α-hydroxy thiol group may have an average of at least 4 carbon atoms; alternatively, at least 6 carbon atoms; or alternatively, at least 8 carbon atoms. In some embodiments, the carboxylic acid residue a terminal α-hydroxy thiol group may have an average of 4 to 20 carbon atoms; alternatively, of 6 to 18 carbon atoms; alternatively, of 8 to 14 carbon atoms; alternatively, of 10 to 11 carbon atoms; alternatively, of about 10 carbon atoms; or alternatively, of about 11 carbon atoms.

In some embodiments, the carboxylic acid residue having a terminal α-hydroxy thiol group may be substantially devoid of other functional groups. In further embodiments, the carboxylic acid residue having a terminal α-hydroxy thiol group may be devoid of other functional groups (i.e. outside of the terminal α-hydroxy and the carbonyl group forming the ester linkage, the carboxylic acid residue contains only carbon and hydrogen).

In an embodiment, the carboxylic acid residues having a terminal α-hydroxy thiol group may have Structure CRHT 1 or Structure CRHT 2.

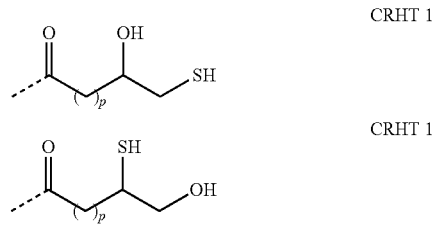

wherein p may be positive integer ranging from 1 to 17; alternatively from 3 to 15; alternatively, from 5 to 11; or alternatively 7 to 8. In some embodiments, p may be 7 or alternatively 8. In other embodiments, p may represent an average number (whole or fractional) of carbon atom ranging from 1 to 17; alternatively from 3 to 15; alternatively, from 5 to 11; alternatively 7 to 8; alternatively about 7; or alternatively, about 8. Within the carboxylic acid residue structure CRHT 1 the dashed line is the bond to the oxygen atom of the ester linkage. In an embodiment, the carboxylic acid residues having a terminal α-hydroxy thiol group may have Structure CRHT 1. In other embodiments, the carboxylic acid residues having a terminal α-hydroxy thiol group may have Structure CRHT 2.

The residue of the polyol may be further described by its structural features. These structural features are independently described herein and may be utilized in any combination to describe the residue of the polyol of the α-hydroxy thiol ester molecules having ester linkages comprising, or consisting essentially of a residue of a polyol and carboxylic acid residues having a terminal α-hydroxy thiol group.

In an embodiment, the residue of the polyol may have 2 to 20 carbon atoms. In some embodiments, the residue of the polyol may have 2 to 12 carbon atoms; alternatively, 2 to 8 carbon atoms; or alternatively, 2 to 5 carbon atoms. In some embodiments, the polyol of the residue of the polyol may have had 2 to 8 hydroxyl group; alternatively, 3 to 6 hydroxyl groups; alternatively, 2 to 4 hydroxyl groups; alternatively, 4 to 8 hydroxyl groups; alternatively, only 3 hydroxyl groups; alternatively, only 4 hydroxyl groups; alternatively, only 5 hydroxyl groups; or alternatively, only 6 hydroxyl groups.

In other embodiments, the residue of the polyol may be a residue of a mixture of polyols. In such an instance the residue of the polyol may have an average of 2 to 20 carbon atoms per polyol molecule; alternatively, an average of 2 to 12 carbon atoms per polyol molecule; alternatively, an average of 2 to 8 carbon atoms per polyol molecule; or alternatively, an average of 2 to 5 carbon atoms per polyol molecule. Further, the mixture of polyols of the residues of the polyols may have had an average of at least 2.5 hydroxyl groups per polyol molecule; alternatively, 2.5 to 8 hydroxyl groups per polyol molecule; alternatively, an average of 2 to 6 hydroxyl groups per polyol molecule; alternatively, an average of 2.5 to 5 hydroxyl groups per polyol molecule; alternatively, an average of 2.5 to 4.5 hydroxyl group per polyol molecule; alternatively, an average of 2.5 to 3.5 hydroxyl group per polyol molecule; alternatively, an average of 3 to 4 hydroxyl group per polyol molecule; alternatively, an average of about 3 hydroxyl groups per polyol molecule; alternatively, an average of about 4 hydroxyl groups per polyol molecule; alternatively, an average of about 5 hydroxyl groups per polyol molecule; or alternatively an average of about 6 hydroxy groups per polyol molecule.

In an embodiment, the polyol that formed the residue of the polyol or mixture of polyols that formed the residues of the polyols may have had a molecular weight or average molecular weight less than 300. In other embodiments, the polyol that formed the residue of the polyol or mixture of polyols that formed the residues of the polyols may have had a molecular weight or average molecular weight less than 250; alternatively less than 200; alternatively, less than 150; or alternatively, less than 100.

In an embodiments, the polyol that formed the residue of the polyol is a diol, triol, a tetraol, pentaol, hexaol, or combination thereof; alternatively a diol, triol, tetraol or combination thereof; or alternatively, a triol, tetraol or combination thereof. In some embodiments, the polyol that formed the residue of the polyol is a diol; alternatively, a triol; alternatively, a tetraol; alternatively, a pentaol; or alternatively, a hexaol. Suitable polyols that may form the residue of the polyol include ethane diol, propanediol, butanediol, pentanediol, hexanediol, cyclohexane diol, phenylethane diol, cyclohexanedimethanol, dimethyolpropane, benzenedimethanol, cyclohexanetriol, trihydroxybenzene, trimethyolethane, trimethylolpropane, trimethylolbutane, glycerol, pentaerythritol, sorbitol, or any combination thereof; alternatively, cyclohexane diol, trimethylol propane, glycerol, pentaerythritol, or combinations thereof; alternatively, glycerol, pentaerythritol, or combinations thereof. In some embodiments, the polyol that may form the residue of the polyol include 1,2-ethanediol, 1,3-propanediol, 1,4-butanediol, 1,5-pentanediol, 1,6-hexanediol, dimethylolpropane, neopentyl glycol, 2-propyl-2-ethyl-1,3-propanediol, 1,2-propanediol, 1,2-butanediol, 1,3-butanediol, 1,4-butanediol, diethylene glycol, triethylene glycol, polyethylene glycol, dipropylene glycol, tripropylene glycol, polypropylene glycol, 1,1-cyclohexanedimethanol, 1,2-cyclohexanedimethanol, 1,3-cyclohexanedimethanol, 1,4-cyclohexanedimethanol, 1,3-dioxane-5,5-dimethanol, 1-phenyl-1,2-ethanediol, trimethylolpropane, trimethyolethane, trimethylolbutane, glycerol, 1,2,5-hexanetriol, pentaerythritol, ditrimethylolpropane, diglycerol, ditrimethylolethane, 1,3,5-trihydroxybenzene, 1,2-benzenedimethanol, 1,3-benzenedimethanol, 1,4-benzenedimethanol, 1-phenyl-1,2-ethanediol, sorbitol, or any combination thereof. In other embodiments, the polyol that may be used as the polyol residue may be trimethylolpropane, glycerol, pentaerythritol, or combinations thereof; alternatively, trimethylolpropane; alternatively, glycerol; alternatively, pentaerythritol; or alternatively sorbitol.

It should be appreciated that not all of the hydroxyl groups of the polyol that form the residue of the polyol may form ester linkages. In some instances some of the hydroxyl groups may not form ester linkages and may remain as hydroxyl group. In an embodiment, greater than 80, 85, 90, 95 percent of all hydroxyl groups of the residue of the polyol form ester linkages. In other embodiments, substantially, all of the hydroxyl groups of the polyol, which forms the residue of a polyol forming linkages with a carboxylic acid having a terminal α-hydroxy thiol group, forms ester linkages. In yet other embodiments, the α-hydroxy thiol ester molecules having ester linkages comprising a residue of a polyol and carboxylic acid residues having a terminal α-hydroxy thiol group are substantially devoid of hydroxy groups derived from the polyol. In some embodiments, the average ratio of carboxylic acid residues having a terminal α-hydroxy thiol to hydroxyl groups of the polyol of the residue of the polyol is greater than 0.70:1; alternatively, greater than 0.75:1; alternatively, greater than 0.80:1; alternatively, greater than 0.85:1; alternatively, greater than 0.90:1; alternatively, greater than 0.95:1.

It will be appreciated that not all of the ester linkages comprising the residue of the polyol may comprise carboxylic acid residues having a terminal α-hydroxy thiol group. For example, some of the ester linkages may comprise a residue of the polyol and carboxylic acid group having a terminal epoxide group due to incomplete conversion of the epoxide feedstock during the reaction with hydrogen sulfide described herein. In such an instance, the α-hydroxy thiol ester molecules having ester linkages comprising a residue of a polyol and a carboxylic acid residues having a terminal α-hydroxy thiol group may be further defined by the average ratio of carboxylic acid residues having an terminal epoxide group to carboxylic acid residues having a terminal α-hydroxy thiol group. In an embodiment, average ratio of carboxylic acid residues having a terminal epoxide group to carboxylic acid residues having a terminal α-hydroxy thiol group may be less than 1:5; alternatively, less than 1:7; or alternatively, less than 1:10. Additionally or alternatively, the feedstock used to produce the α-hydroxy thiol ester molecules may contain ester linkages with saturated carboxylic acid that can not be thiolated and/or carboxylic acid residue having epoxide group which were not thiolated. Considering this situation, in some embodiments, greater than 75, 80, 85, or 90 percent of all ester linkages comprising the residue of the polyol comprise carboxylic acid residues having the terminal α-hydroxy thiol group.

In an embodiment, the α-hydroxy thiol ester molecules, whether described as having particular functional groups or as α-hydroxy thiol ester molecules having ester linkages comprising a residue of a polyol and carboxylic acid residues having a terminal α-hydroxy thiol group, may have an average ratio of α-hydroxy thiol groups to ester groups in the α-hydroxy thiol ester molecules of less than 1.15:1; alternatively, less than 1.1:1; or alternatively, less than 1.05:1. In some embodiments, the α-hydroxy thiol ester molecules, whether described as having particular functional groups or as α-hydroxy thiol ester molecules having ester linkages comprising a polyol residue and carboxylic acid residues having a terminal α-hydroxy thiol group, may have an average ratio of α-hydroxy thiol groups to ester groups in the α-hydroxy thiol ester molecules that ranges from 0.75:1 to 1.15:1; alternatively, ranges from 0.85:1 to 1.1:1; or alternatively, ranges from 0.90:1 to 1.05:1. In other embodiments, the α-hydroxy thiol ester molecules, whether described as having particular functional groups or as α-hydroxy thiol ester molecules having ester linkages comprising a polyol residue and carboxylic acid residues having a terminal α-hydroxy thiol group, may have an average ratio of α-hydroxy thiol groups to ester groups in the thiol ester molecules of about 1:1.

In some embodiments, the α-hydroxy thiol ester molecules, whether described as having particular functional groups or as α-hydroxy thiol ester molecules having ester linkages comprising a polyol residue and carboxylic acid residues having a terminal α-hydroxy thiol group, may have an average thiol sulfur content of 5 to 20 weight percent; alternatively, 7 to 18 weight percent; alternatively, 9 to 16 weight percent. In other embodiment, the α-hydroxy thiol ester molecules, whether described as having particular functional groups or as α-hydroxy thiol ester molecules having ester linkages comprising a polyol residue and carboxylic acid residues having a terminal α-hydroxy thiol group, may have a thiol equivalent weight of 150 to 500 grams; alternatively, 180 to 400 grams; alternatively, 200 to 350 grams per equivalent. In other embodiment, the α-hydroxy thiol ester molecules, whether described as having particular functional groups or as α-hydroxy thiol ester molecules having ester linkages comprising a polyol residue and carboxylic acid residues having a terminal α-hydroxy thiol group, may have a hydroxyl equivalent weight of 130 to 500 grams per equivalent; alternatively, 170 to 400 grams per equivalent; alternatively, 190 to 350 grams per equivalent.

Cross-Linked Thiol Ester Compositions

In an aspect, the present invention relates to cross-linked thiol ester compositions comprising, or consisting essentially of cross-linked thiol ester molecules. Generally, the cross-linked thiol ester molecules are oligomers of thiol ester molecules that are connected together by polysulfide linkages —$S_x$— wherein x is an integer greater than 1. As the cross-linked thiol ester may be described as an oligomer of thiol ester molecules, the thiol ester molecules may be described as the monomer from which the cross-linked thiol esters are produced. In embodiments, the cross-linked thiol ester may be produced from thiol ester molecules and may be called a cross-linked thiol ester molecule. In other embodiments, the cross-linked thiol ester molecules may be produced from α-hydroxy thiol ester molecules and may be called a crossed-linked α-hydroxy thiol ester molecule. Generally, any thiol ester molecule and/or hydroxy thiol ester molecule describe herein may be utilized as a monomer for the cross-linked thiol ester compositions.

In an aspect, the cross-linked thiol ester composition comprises a thiol ester oligomer having at least two thiol ester monomers connected by a polysulfide linkage having a structure —$S_Q$—, wherein Q is an integer greater than 1. In an aspect, the polysulfide linkage may be the polysulfide linkage —$S_Q$—, wherein Q is 2, 3, 4, or mixtures thereof. In other embodiments, Q can be 2; alternatively, 3; or alternatively, 4.

In an aspect, the cross-linked thiol ester composition comprises a thiol ester oligomer having at least 3 thiol ester monomers connected by polysulfide linkages; alternatively, 5 thiol ester monomers connected by polysulfide linkages; alternatively, 7 thiol ester monomers connected by polysulfide linkages; or alternatively, 10 thiol ester monomers connected by polysulfide linkages. In yet other embodiments, the cross-linked thiol ester composition comprises a thiol ester oligomer having from 3 to 20 thiol ester monomers connected by polysulfide linkages; alternatively, from 5 to 15 thiol ester monomers connected by polysulfide linkages; or alternatively, from 7 to 12 thiol ester monomers connected by polysulfide linkages.

In an aspect, the cross-linked thiol ester molecules may include both thiol ester monomers and thiol ester oligomers. For example, the cross-linked thiol ester composition may have a combined thiol ester monomer and thiol ester oligomer average molecular weight greater than 2,000, greater than 5,000 or greater than 10,000. Further, the cross-linked thiol ester composition may have a combined thiol ester monomer and thiol ester oligomer average molecular weight ranging from 2,000 to 20,000, from 3,000 to 15,000 or from 7,500 to 12,500. In another aspect, the thiol ester monomers and thiol ester oligomers may have a total thiol sulfur content greater than 0.5 weight percent, greater than 1 weight percent, greater than 2 weight percent or greater than 4 weight percent. Further, the thiol ester monomers and the thiol ester oligomers may have a total thiol sulfur content from 0.5 weight percent to 8 weight percent, from 4 weight percent to 8 weight percent or 0.5 weight percent to 4 weight percent.

In an aspect, the cross-linked α-hydroxy thiol ester composition comprises an α-hydroxy thiol ester oligomer having at least two α-hydroxy thiol ester monomers connected by a polysulfide linkage having a structure —$S_Q$—, wherein Q is an integer greater than 1. In an aspect, the polysulfide linkage may be the polysulfide linkage —$S_Q$—, wherein Q is 2, 3, 4, or mixtures thereof. In other embodiments, Q can be 2; alternatively, 3; or alternatively, 4.

In an aspect, cross-linked α-hydroxy thiol ester composition comprises a α-hydroxy thiol ester oligomer having at least 3 α-hydroxy thiol ester monomers connected by polysulfide linkages; alternatively, at least 5 α-hydroxy thiol ester monomers connected by polysulfide linkages; alternatively, at least 7 α-hydroxy thiol ester monomers connected by polysulfide linkages; or alternatively, at least 10 α-hydroxy thiol ester monomers connected by polysulfide linkages. In yet other embodiments, the cross-linked α-hydroxy thiol ester composition comprises a α-hydroxy thiol ester oligomer having from 3 to 20 α-hydroxy thiol ester monomers connected by polysulfide linkages; alternatively, from 5 to 15 α-hydroxy thiol ester monomers connected by polysulfide linkages; or alternatively, from 7 to 12 α-hydroxy thiol ester monomers connected by polysulfide linkages.

In an aspect, the cross-linked α-hydroxy thiol ester molecules may include both α-hydroxy thiol ester monomers and α-hydroxy thiol ester oligomers. For example, the cross-linked α-hydroxy thiol ester composition may have a combined α-hydroxy thiol ester monomer and α-hydroxy thiol ester oligomer average molecular weight greater than 2,000, greater than 5,000 or greater than 10,000. Further, the cross-linked α-hydroxy thiol ester composition may have a combined α-hydroxy thiol ester monomer and α-hydroxy thiol ester oligomer average molecular weight ranging from 2,000 to 20,000, from 3,000 to 15,000 or from 7,500 to 12,500. In another aspect, the α-hydroxy thiol ester monomers and α-hydroxy thiol ester oligomers may have a total thiol sulfur content greater than 0.5 weight percent, greater than 1 weight percent, greater than 2 weight percent or greater than 4 weight percent. Further, the α-hydroxy thiol ester monomers and the α-hydroxy thiol ester oligomers may have a total thiol sulfur content from 0.5 weight percent to 8 weight percent, from 4 weight percent to 8 weight percent or 0.5 weight percent to 4 weight percent.

Terminal Epoxide Compositions

In an aspect, the epoxide ester compositions comprising, or consisting essentially of, epoxide ester molecules having terminal epoxide groups may be utilized as a feedstock for producing α-hydroxy thiol ester compositions comprising, or consisting essentially of, α-hydroxy thiol ester molecules having terminal α-hydroxy thiol groups. The epoxide ester molecules having terminal epoxide groups may be described as comprising, consisting essentially of, one or more functional groups present in the epoxide ester molecules having terminal epoxide groups of the epoxide ester composition. Each of the functional groups that may be present in the epoxide ester molecules having terminal epoxide groups are independently described herein and may be utilized in any combination to described the epoxide ester molecules having terminal epoxide groups.

The independent functional groups that can be utilized to describe ester molecules having terminal epoxide groups include: the number of (or average number of) ester groups (per epoxide ester molecule), the number of (or average number of) terminal epoxide groups (per epoxide ester molecule), the ratio of (or average ratio of) terminal epoxide groups to ester groups (per epoxide ester molecule), the number of (or average number of) unreacted carbon-carbon double bonds (per epoxide ester molecule), and the average epoxide content of the epoxide ester molecules.

The epoxide ester molecules having terminal epoxide groups of the epoxide ester compositions may be produced from any unsaturated ester composition comprising unsaturated ester molecules having terminal carbon-carbon double bonds described herein. It should be noted that the feedstock unsaturated esters may have multiple terminal carbon-carbon double bonds and may contain many different unsaturated ester molecules. This fact, combined with carbon-carbon double bond reactivity and statistical probability, dictate that each epoxide ester molecule having terminal epoxide groups of the epoxide ester composition may not have the same number of functional groups, the same ratios of functional groups, and/or the same additional features. Thus, the number of functional group, ratios of functional groups, and/or additional features of the epoxide ester molecules having terminal epoxide groups of the epoxide ester composition may be referred to as an average per epoxide thiol ester molecules within the epoxide ester composition.

In an embodiment, the epoxide ester molecules having terminal epoxide groups may have at least 2 ester groups; alternatively at least 3 ester groups; or alternatively, at least 4 ester groups. In other embodiments, the epoxide ester molecules having terminal epoxide groups may have from 2 to 8 ester groups; alternatively, 3 to 6 ester groups; alternatively, 3 to 4 ester groups; alternatively, only 3 ester groups; or alternatively, only 4 ester groups. In further embodiments, the epoxide ester molecules having terminal epoxide groups may have an average of at least 2 ester groups per epoxide ester molecule; alternatively, an average of at least 2.5 ester groups per epoxide ester molecule; or alternatively, an average of at least 3 ester groups per epoxide ester molecule. In yet further embodiments, the epoxide ester molecules having terminal epoxide groups may have an average of from 2 to 8 ester groups per epoxide ester molecule; alternatively, an average of from 2 to 7 ester groups per epoxide ester molecule; alternatively, an average of from 2.5 to 5 ester groups per epoxide ester molecule; or alternatively, an average of from 3 to 4 ester groups per epoxide ester molecule. In yet other embodiments, the epoxide ester molecules having terminal epoxide groups may have an average of about 3 ester groups per epoxide ester molecule; or alternatively, an average of about 4 ester groups per epoxide ester molecule.

In an embodiment, the epoxide ester molecules of the epoxide ester composition have at least 2 terminal epoxide groups; alternatively, at least 3 terminal epoxide groups; or alternatively, at least 4 terminal epoxide groups. In other embodiments, epoxide ester molecules have from 2 to 8 terminal epoxide groups; alternatively, 3 to 6 terminal epoxide groups; alternatively, 3 to 4 terminal epoxide groups; alternatively, only 3 terminal epoxide groups; or alternatively, only 4 terminal epoxide groups. In further embodiments, the epoxide ester molecules have an average of at least 1.5 terminal epoxide groups per epoxide ester molecules; alternatively, an average of at least 2.5 terminal epoxide groups per epoxide ester molecules; or alternatively, an average of at least 3 terminal epoxide groups per epoxide ester molecules. In yet further embodiments, the epoxide ester molecules have an average of from 1.5 to 8 terminal epoxide groups per epoxide ester molecules; alternatively, an average of from 2 to 7 terminal epoxide groups per epoxide ester molecules; alternatively, an average of from 2.5 to 5 terminal epoxide groups per epoxide ester molecules; or alternatively, an average of from 3 to 4 terminal epoxide groups per epoxide ester molecules. In yet other embodiments, the epoxide ester molecules have an average of about 3 terminal epoxide groups per epoxide ester molecules; or alternatively, an average of about 4 terminal epoxide groups per epoxide ester molecules.

In an embodiment, the epoxide ester molecules having terminal epoxide groups may contain carbon-carbon double bonds. These carbon-carbon double bonds may result from incomplete conversion of the feedstock during the formation of the epoxide molecules. In some embodiments, the average ratio of carbon-carbon double bonds to epoxide groups is less than 1:5; alternatively, less than 1:7; or alternatively, less than 1:10.

In another aspect, the epoxide ester molecules within the epoxide ester compositions may be described as having ester linkages comprising a residue of a polyol and a carboxylic acid residue having a terminal epoxide group. Additional features of the residue of the polyol and carboxylic acid residue having a terminal epoxide group are independently described herein and may be utilized in any combination to further describe the epoxide ester molecules.

The epoxide ester molecules described as having ester linkages comprising a residue of a polyol and a carboxylic acid residue having a terminal epoxide group may be produced from any unsaturated ester having a terminal carbon-carbon double bond described herein. It should be noted that the feedstock unsaturated esters may have multiple carbon-carbon double bonds and may contain many different unsaturated ester molecules. This fact, combined with carbon-carbon double reactivity differences and statistical probability, dictate that each epoxide ester molecule having ester linkages comprising a residue of a polyol and a carboxylic acid residue having a terminal epoxide group may not have the same structure. Thus, particular features of the epoxide ester molecules having ester linkages comprising a residue of a polyol and a carboxylic acid residue having a terminal epoxide group may be described as an average per epoxide ester molecule.

In an embodiment, the epoxide ester molecules having ester linkages comprises a residue of a polyol and a carboxylic acid residue having a terminal epoxide group. The residue of the polyol and the carboxylic acid residue having a terminal epoxide group are independent elements of epoxide ester molecules having ester linkages. Consequently, the features of the residue of the polyol and the carboxylic acid having a terminal epoxide group are independently described herein and may be used in any combination to describe the epoxide ester molecules having ester linkages comprising a residue of a polyol and carboxylic acid residues having a terminal epoxide group.

The carboxylic acid residue having a terminal epoxide group may be further described by its structural features. These structural features are independently described herein and may be utilized in any combination to describe the carboxylic acid residue of the epoxide ester molecules having ester linkages comprising a residue of a polyol and carboxylic acid residues having a terminal epoxide group.

In an embodiment, the carboxylic acid residue having the terminal epoxide group is linear. In another embodiment, the carboxylic acid residue having the terminal epoxide group is branched.

In an embodiment, the carboxylic acid residue having a terminal epoxide group may have at least 4 carbon atoms; alternatively, at least 6 carbon atoms; or alternatively, at least 8 carbon atoms. In some embodiments, the carboxylic acid residue having a terminal epoxide group may have from 4 to 20 carbon atoms; alternatively, from 6 to 18 carbon atoms; alternatively, from 8 to 14 carbon atoms; alternatively, from 10 to 11 carbon atoms; alternatively, only 10 carbon atoms; or alternatively, only 11 carbon atoms. In an embodiment, the carboxylic acid residue a terminal epoxide group may have an average of at least 4 carbon atoms; alternatively, at least 6 carbon atoms; or alternatively, at least 8 carbon atoms. In some embodiments, the carboxylic acid residue a terminal epoxide group may have an average of 4 to 20 carbon atoms; alternatively, of 6 to 18 carbon atoms; alternatively, of 8 to 14 carbon atoms; alternatively, of 10 to 11 carbon atoms; alternatively, of about 10 carbon atoms; or alternatively, of about 11 carbon atoms.

In an embodiment, the carboxylic acid residue having a terminal epoxide group may be substantially devoid of other functional groups. In further embodiments, the carboxylic acid residue having a terminal epoxide group may be devoid of other functional groups (i.e. outside of the terminal α-hydroxy and the carbonyl group forming the ester linkage, the carboxylic acid residue contains only carbon and hydrogen).

In an embodiment, the carboxylic acid residues having a terminal epoxide group may have Structure CRE 1.

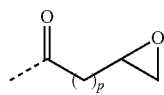

CRE 1 wherein p may be positive integer ranging from 1 to 17; alternatively from 3 to 15; alternatively, from 5 to 11; or alternatively 7 to 8. In some embodiments, p may be 7 or alternatively 8. In other embodiments, p may represent an average number (whole or fractional) of carbon atom ranging from 1 to 17; alternatively from 3 to 15; alternatively, from 5 to 11; alternatively 7 to 8; alternatively about 7; or alternatively, about 8. Within the carboxylic acid residue structure CRE 1 the dashed line is the bond to the oxygen atom of the ester linkage.

The residue of the polyol may be further described by its structural features. These structural features are independently described herein and may be utilized in any combination to describe the residue of the polyol of the epoxide ester molecules having ester linkages comprising, or consisting essentially of a residue of a polyol and carboxylic acid residues having a terminal epoxide group.

In an embodiment, residue of the polyol may have 2 to 20 carbon atoms. In some embodiments, the residue of the polyol may have 2 to 12 carbon atoms; alternatively, 2 to 8 carbon atoms; or alternatively, 2 to 5 carbon atoms. In some embodiments, the polyol of the residue of the polyol may have had 2 to 8 hydroxyl group; alternatively, 3 to 6 hydroxyl groups; alternatively, 2 to 4 hydroxyl groups; alternatively, 4 to 8 hydroxyl groups; alternatively, only 3 hydroxyl groups; alternatively, only 4 hydroxyl groups; alternatively, only 5 hydroxyl groups; or alternatively, only 6 hydroxyl groups.

In other embodiments, the residue of the polyol may be a residue of a mixture of polyols. In such an instance the residue of the polyol may have an average of 2 to 20 carbon atoms per polyol molecule; alternatively, an average of 2 to 12 carbon atoms per polyol molecule; alternatively, an average of 2 to 8 carbon atoms per polyol molecule; or alternatively, an average of 2 to 5 carbon atoms per polyol molecule. Further, the mixture of polyols of the residues of the polyols may have had an average of at least 2.5 hydroxyl groups per polyol molecule; alternatively, 2.5 to 8 hydroxyl groups per polyol molecule; alternatively, an average of 2 to 6 hydroxyl groups per polyol molecule; alternatively, an average of 2.5 to 5 hydroxyl groups per polyol molecule; alternatively, an average of 2.5 to 4.5 hydroxyl group per polyol molecule; alternatively, an average of 2.5 to 3.5 hydroxyl group per polyol molecule; alternatively, an average of 3 to 4 hydroxyl group per polyol molecule; alternatively, an average of about 3 hydroxyl groups per polyol molecule; alternatively, an average of about 4 hydroxyl groups per polyol molecule; alternatively, an average of about 5 hydroxyl groups per polyol molecule; or alternatively an average of about 6 hydroxy groups per polyol molecule.

In an embodiment, the polyol that formed the residue of the polyol or mixture of polyols that formed the residues of the polyols may have had a molecular weight or average molecular weight less than 300. In other embodiments, the polyol that formed the residue of the polyol or mixture of polyols that formed the residues of the polyols may have had a molecular weight or average molecular weight less than 250; alternatively less than 200; alternatively, less than 150; or alternatively, less than 100.

In an embodiments, the polyol that formed the residue of the polyol is a diol, triol, a tetraol, pentaol, hexaol, or combination thereof; alternatively a diol, triol, tetraol or combination thereof; or alternatively, a triol, tetraol or combination thereof. In some embodiments, the polyol that formed the residue of the polyol is a diol; alternatively, a triol; alternatively, a tetraol; alternatively, a pentaol; or alternatively, a hexaol. Suitable polyols that may form the residue of the polyol include ethane diol, propanediol, butanediol, pentanediol, hexanediol, cyclohexane diol, phenylethane diol, cyclohexanedimethanol, dimethyolpropane, benzenedimethanol, cyclohexanetriol, trihydroxybenzene, trimethyolethane, trimethylolpropane, trimethylolbutane, glycerol, pentaerythritol, sorbitol, or any combination thereof; alternatively, cyclohexane diol, trimethylol propane, glycerol, pentaerythritol, or combinations thereof; alternatively, glycerol, pentaerythritol, or combinations thereof. In some embodiments, the polyol that may form the residue of the polyol include 1,2-ethanediol, 1,3-propanediol, 1,4-butanediol, 1,5-pentanediol, 1,6-hexanediol, dimethylolpropane, neopentyl glycol, 2-propyl-2-ethyl-1,3-propanediol, 1,2-propanediol, 1,2-butanediol, 1,3-butanediol, 1,4-butanediol, diethylene glycol, triethylene glycol, polyethylene glycol, dipropylene glycol, tripropylene glycol, polypropylene glycol, 1,1-cyclohexanedimethanol, 1,2-cyclohexanedimethanol, 1,3-cyclohexanedimethanol, 1,4-cyclohexanedimethanol, 1,3-dioxane-5,5-dimethanol, 1-phenyl-1,2-ethanediol, trimethylolpropane, trimethylolethane, trimethylolbutane, glycerol, 1,2,5-hexanetriol, pentaerythritol, ditrimethylolpropane, diglycerol, ditrimethylolethane, 1,3,5-trihydroxybenzene, 1,2-benzenedimethanol, 1,3-benzenedimethanol, 1,4-benzenedimethanol, 1-phenyl-1,2-ethanediol, sorbitol, or any combination thereof. In other embodiments, the polyol that may be used as the polyol residue may be trimethylolpropane, glycerol, pentaerythritol, or combinations thereof; alternatively, trimethylolpropane; alternatively, glycerol; alternatively, pentaerythritol; or alternatively sorbitol.

It should be appreciated that not all of the hydroxyl groups of the polyol that form the residue of the polyol may form ester linkages. In some instances some of the hydroxyl groups may not form ester linkages and may remain as hydroxyl group. In an embodiment, greater than 80, 85, 90, 95 percent of all hydroxyl groups of the residue of the polyol form ester linkages. In other embodiments, substantially all of the hydroxyl groups of the polyol, which forms the residue of a polyol forming linkages with a carboxylic acid having a terminal epoxide group, form ester linkages. In yet other embodiments, the epoxide ester molecules having ester linkages that may comprise a residue of a polyol and a carboxylic acid residue having a terminal epoxide group are substantially devoid of hydroxy groups derived from the polyol. In some embodiments, the average ratio of carboxylic acid residues having a terminal epoxide group to hydroxyl groups of the polyol of the residue of the polyol is greater than 0.70:1; alternatively, greater than 0.75:1; alternatively, greater than 0.80:1; alternatively, greater than 0.85:1; alternatively, greater than 0.90:1; alternatively, greater than 0.95:1.

It will be appreciated that not all of the ester linkages comprising the residue of the polyol may comprise carboxylic acid residues having a terminal epoxide group. For example, some of the ester linkages may comprise a residue of the polyol and carboxylic acid group having a terminal carbon-carbon double bond due to incomplete conversion of the feedstock unsaturated ester molecules during the formation of the epoxide ester molecules. In such an instance, the epoxide ester molecules having ester linkages comprising a residue of a polyol and a carboxylic acid residues having a terminal epoxide group may be further defined by the average ratio of carboxylic acid residues having a carbon-carbon double bond to carboxylic acid residues having a terminal epoxide group. In an embodiment, the average ratio of carboxylic acid residues having a carbon-carbon double bond to carboxylic acid residues having a terminal epoxide group may be less than 1:5; alternatively, less than 1:7; or alternatively, less than 1:10. Additionally or alternatively, the feedstock used to produce the epoxide ester molecules may contain ester linkages with saturated carboxylic acid residues that can not be thiolated and/or carboxylic acid residues having carbon-carbon double bonds which were not thiolated. Considering this situation, in some embodiments, greater than 75, 80, 85, or 90 percent of all ester linkages comprising the residue of the polyol comprise carboxylic acid residues having the terminal epoxide group.

In an embodiment, the epoxide ester molecules, whether described as having particular functional groups or as epoxide ester molecules having ester linkages comprising a residue of a polyol and carboxylic acid residues having a terminal epoxide group, may have an average ratio of epoxide groups to ester groups in the epoxide ester molecules of less than 1.15:1; alternatively, less than 1.1:1; or alternatively, less than 1.05:1. In some embodiments, the epoxide ester molecules, whether described as having particular functional groups or as epoxide ester molecules having ester linkages comprising a polyol residue and carboxylic acid residues having a terminal epoxide group, may have an average ratio of epoxide groups to ester groups in the epoxide ester molecules that ranges from 0.75:1 to 1.15:1; alternatively, ranges from 0.85:1 to 1.1:1; or alternatively, ranges from 0.90:1 to 1.05:1. In other embodiments, the epoxide ester molecules, whether described as having particular functional groups or as epoxide ester molecules having ester linkages comprising a polyol residue and carboxylic acid residues having a terminal epoxide group, may have an average ratio of epoxide groups to ester groups in the thiol ester molecules of about 1:1.

In some embodiments, the epoxide ester molecules, whether described as having particular functional groups or as epoxide ester molecules having ester linkages comprising a polyol residue and carboxylic acid residues having a terminal epoxide group, may have an average epoxide oxygen content of 2.5 to 12 weight percent; alternatively, 3.5 to 10 weight percent; alternatively, 4.5 to 9 weight percent. In other embodiment, the epoxide ester molecules, whether described as having particular functional groups or as epoxide ester molecules having ester linkages comprising a polyol residue and carboxylic acid residues having a terminal epoxide group, may have an epoxy equivalent weight of 140 to 500 grams; alternatively, 170 to 400 grams; alternatively, 200 to 350 grams.

Process for Making Thiol Ester Compositions

The thiol ester molecules having thiol groups located on a terminal carbon atom and/or thiol groups located on the carbon atom adjacent to the terminal carbon atom or the thiol ester compositions comprising, or consisting essentially of, the aforementioned thiol ester molecules may be formed or produced by contacting hydrogen sulfide and unsaturated ester molecules having a terminal carbon-carbon double bond or unsaturated ester composition comprising, or consisting essentially of, the aforementioned unsaturated ester molecules having a terminal carbon-carbon double bond.

Generally the method for producing the thiol ester molecules (or composition comprising, or consisting essentially of thiol ester molecules) comprises a) contacting hydrogen sulfide and unsaturated ester molecules having terminal carbon-carbon double bonds (or composition comprising, or consisting essentially of, unsaturated ester molecules having terminal carbon-carbon double bonds), and b) forming thiol ester molecules (or the thiol ester composition comprising, or consisting essentially of, thiol ester molecules). Generally, the thiol ester molecules (or composition comprising, or consisting essentially of or thiol ester molecules) are formed at conditions capable of forming the thiol ester molecules (or thiol ester composition comprising, or consisting essentially of, the thiol ester molecules). The processes described herein can be applied to any unsaturated ester molecules having a terminal carbon-carbon double bond (or unsaturated ester composition comprising, or consisting essentially of, unsaturated ester molecules having a terminal carbon-carbon double bond) described herein. The processes described herein can be used to produce any thiol ester molecules having thiol groups located on a terminal carbon atom and/or thiol groups located on the carbon atom adjacent to the terminal carbon atom (or thiol ester compositions comprising, or consisting essentially of, thiol ester molecules having thiol groups located on a terminal carbon atom and/or thiol groups located on the carbon atom adjacent to the terminal carbon atom) described herein. The process for producing the thiol ester composition can also include any additional process steps or process conditions described herein.

The molar ratio of hydrogen sulfide to terminal alkene groups utilized in the process to produce the thiol ester molecules (or composition) can be any molar ratio that produces the desired thiol ester molecules (or compositions). For example, the thiol ester molecules may have a molar ratio of the hydrogen sulfide to terminal alkene groups of greater than 2. In other embodiments, the molar ratio of hydrogen sulfide to terminal alkene groups may be greater than 5; alternatively, greater than 10; alternatively, greater than 15; or alternatively, greater than 20. In other embodiments, the molar ratio of hydrogen sulfide to terminal alkene groups may be from 2 to 500; alternatively, from 5 to 200; alternatively, from 10 to 100; or alternatively, from 100 to 200.

The reaction between the unsaturated ester molecules and hydrogen sulfide may be catalyzed. The catalyst may be a heterogeneous catalyst or a homogeneous catalyst. In other embodiments, the reaction of the unsaturated ester molecules and hydrogen sulfide may be initiated by a free radical initiator or ultraviolet (UV) radiation. Free radical initiators or ultraviolet (UV) radiation is preferred when thiol ester molecules having a thiol group located on a terminal carbon atom are desired. Heterogeneous catalysts and/or homogenous acid catalysts are preferred when thiol ester molecules having a thiol group located on the carbon atom adjacent to a terminal carbon atom are desired.

The free radical initiator may be any free radical initiator capable of forming free radicals under thermal or light photolysis. For example, the free radical initiator may be selected from the general class of compounds having a —N=N— group or a —O—O— group. Specific classes of free radical initiators may include diazo compounds, dialkyl peroxides, hydroperoxides, and peroxy esters. Specific initiators may include, but are not limited to, azobenzene, 2,2'-azobis(2-methylpropionitrile, 4,4'-azobis(4-cyanovaleric acid), 1,1'-azobis(cyclohexanecarbonitrile), 2,2'-azobis(2-methylpropane-), 2,2'-azobis(2-methylpropionamidine)dihydrochloride, methylpropionitrile, azodicarboxamide, tert-butyl hydroperoxide, di-tert-butyl peroxide, octylperbenzoate. In some embodiments, the free radical initiated reaction may be performed at a reaction temperature within ±50° C. of the 1 hour half life of the free radical initiator. In other embodiments, the free radical initiated reaction may be performed at a reaction temperature within ±25° C. of the 1 hour half life of the free radical initiator; alternatively, at a reaction temperature within ±20° C. of the 1 hour half life of the free radical initiator; alternatively, at a reaction temperature within ±15° C. of the 1 hour half life of the free radical initiator; alternatively, at a reaction temperature within ±10° C. of the 1 hour half life of the free radical initiator. In an embodiment in which the free radical initiator catalyst reaction of the unsaturated ester and hydrogen sulfide is initiated by light photolysis, the light can be any light capable of creating free radicals. For example, the light may be ultraviolet (UV) or visible radiation.

The reaction of the unsaturated ester molecules having terminal carbon-carbon double bonds and hydrogen sulfide may be initiated by UV radiation. In these embodiments, the UV radiation can be any UV radiation capable of initiating the reaction of the terminal alkene group and hydrogen sulfide. In some embodiments, the UV radiation may be generated by a medium pressure mercury lamp. Although UV radiation has been described as the light source, other suitable types of light sources will be apparent to those of skill in the art and are to be considered within the scope of the present invention.

The heterogeneous catalyst may comprise one or a mixture of acid clays (such as Filtrol®-24, which is commercially available from Englehard), acid zeolites (such as LZY-84, which is commercially available from UOP), cobalt/molybdenum oxide supported catalysts (such as TK-554, which is commercially available from Haldor-Topsoe), and nickel/molybdenum supported oxide catalysts (such as TK-573, which is commercially available from Haldor-Topsoe). The homogeneous acid catalyst may be an organic sulfonic acid. Non-limiting examples of organic sulfonic acids which may be utilized separately or in any combination include methanesulfonic acid and toluenesulfonic acid. Other suitable types of heterogeneous and homogeneous catalysts will be apparent to those of skill in the art and are to be considered within the scope of the present invention.

The reaction of the and hydrogen sulfide may be performed in a batch reactor or a continuous reactor. Continuous reactors that may be utilized include continuous stirred reactors, fixed bed reactors, and the like. Batch reactors that may be utilized include UV batch reactors. Other types of batch and continuous reactors that can be used in embodiments of the present invention will be apparent to those of skill in the art and are to be considered within the scope of the present invention.

If a continuous reactor is used for the reaction, an hourly space velocity feed weight of the terminal alkene composition ranging from 0.1 to 5 may be used to produce the desired thiol ester molecules. Alternatively, the hourly space velocity feed weight may range from 0.1 to 5; alternatively, from 0.1 to 2. Alternatively, the unsaturated ester molecule weight hourly space velocity may be about 0.1; alternatively, the unsaturated ester weight hourly space velocity may be about 0.25; or alternatively, the feed unsaturated ester weight hourly space velocity may be about 2.

The reaction time used for the reaction of the unsaturated ester molecules having a terminal carbon-carbon double bond and hydrogen sulfide may be determined by the formation of the desired thiol ester molecules. For example, the time required for the reaction of the unsaturated ester molecules having a terminal carbon-carbon double bond and hydrogen sulfide may be at least 5 minutes. In some embodiments, the time required for the reaction of the unsaturated ester molecules having a terminal carbon-carbon double bond and hydrogen sulfide may range from 5 minutes to 72 hours; alternatively, from 10 minutes to 48 hours; or alternatively, from 15 minutes to 36 hours.

The reaction between the unsaturated ester molecules having a terminal carbon-carbon double bond and hydrogen sulfide may be performed at any temperature capable of forming the desired thiol ester molecules. For example, the unsaturated ester molecules having a terminal carbon-carbon double bond and hydrogen sulfide may be reacted at a temperature greater than −20° C. In other embodiments, the unsaturated ester molecules having a terminal carbon-carbon double bond and hydrogen sulfide may be reacted at a temperature greater than 0° C.; alternatively, greater than 20° C.; alternatively, greater than 50° C.; alternatively, greater than 80° C.; or alternatively, greater than 100° C. In yet other embodiments, the unsaturated ester molecules having a terminal carbon-carbon double bond and hydrogen sulfide may be reacted at a temperature from −20° C. to 200° C.; alternatively, from 120° C. to 240° C.; alternatively, from 170° C. to 210° C.; alternatively, from 185° C. to 195° C.; alternatively, from 20° C. to 200° C.; alternatively, from 20° C. to 170° C.; or alternatively, from 80° C. to 140° C.

The reaction between the unsaturated ester molecules having a terminal carbon-carbon double bond and hydrogen sulfide may be performed at any pressure that maintains a portion of the hydrogen sulfide in a liquid state. For example, the unsaturated ester molecules having a terminal carbon-carbon double bond and hydrogen sulfide reaction may be performed at a pressure ranging from 100 psig to 2000 psig. In other embodiments, the unsaturated ester molecules having a terminal carbon-carbon double bond and hydrogen sulfide reaction may be performed at a pressure ranging from 150 psig to 1000 psig; or alternatively, from 200 psig to 600 psig.

In some aspects, the reaction between hydrogen sulfide and the unsaturated ester molecules may occur in the presence of a solvent. In other aspects, the reaction between the unsaturated ester molecules and hydrogen sulfide occurs in the substantial absence of a solvent. When the solvent is present, the solvent may be a selected from aromatic hydrocarbons, aliphatic hydrocarbons, organic alcohols, organic ethers, organic carbonates, organic esters, halogenated aliphatic hydrocarbons, aromatic hydrocarbons, halogenated aromatic hydrocarbons, and combinations thereof. Aliphatic hydrocarbons, which may be useful as a solvent, include $C_4$ to $C_{20}$ hydrocarbons, or alternatively, $C_5$ to $C_{10}$ hydrocarbons, and may be cyclic or acyclic and include linear or branched isomers, unless otherwise specified. Non-limiting examples of suitable acyclic aliphatic solvents include pentane, hexane, heptane, octane, and combinations thereof. Non-limiting examples of suitable cyclic aliphatic solvents include cyclohexane, methyl cyclohexane, and combinations thereof. Aromatic hydrocarbons, which may be useful as a solvent, include $C_6$ to $C_{20}$ aromatic hydrocarbons; or alternatively, $C_6$ to $C_{10}$ aromatic hydrocarbons. Non-limiting examples of suitable aromatic hydrocarbons include benzene, toluene, xylene (including ortho-xylene, meta-xylene, para-xylene, or mixtures thereof), and ethylbenzene, or combinations thereof. Organic alcohols, organic ethers, organic carbonates, organic esters, which may be useful as a solvent include $C_2$ to $C_{20}$ organic alcohols, organic ethers, organic carbonates, organic esters, organic ketones, or organic aldehydes; alternatively, $C_2$ to $C_{10}$ organic alcohols, organic ethers, organic carbonates, organic esters, organic ketones, or organic aldehydes; or alternatively, $C_2$ to $C_5$ organic alcohols, organic ethers, organic carbonates, organic esters, organic ketones, or organic aldehydes. Non-limiting examples of suitable alcohol solvents include methanol, 1-propanol, 2-propanol, 1-butanol, 2-butanol, 2-methyl-2-propanol, or mixtures thereof. Suitable ether solvents may be cyclic or acyclic. Non-limiting examples of suitable ethers which may be useful as a solvent include dimethyl ether, diethyl ether, methyl ethyl ether, monoethers or diethers of glycols (e.g., dimethyl glycol ether), furans, substituted furans, dihydrofuran, substituted dihydrofurans, tetrahydrofuran (THF), substituted tetrahydrofurans, tetrahydropyrans, substituted tetrahydropyrans, 1,3-dioxanes, substituted 1,3-dioxanes, 1,4-dioxanes, substituted 1,4-dioxanes, or mixtures thereof. In an embodiment, each substituent of a substituted furan, substituted dihydrofuran, substituted tetrahydrofuran, substituted tetrahydropyran, substituted 1,3-dioxane, or substituted 1,4-dioxane, can be a $C_1$ to $C_5$ alkyl group. Non-limiting examples of suitable organic carbonates, which may be utilized as a solvent, include ethylene carbonate, propylene carbonate, diethyl carbonate, diethyl carbonate, and combinations thereof. Non-limiting examples of suitable esters, which may be utilized as a solvent, include ethyl acetate, propyl acetate, butyl acetate, isobutyl isobutyrate, and combinations thereof. Halogenated aliphatic hydrocarbons, which may be useful as a solvent, include $C_1$ to $C_{15}$ halogenated aliphatic hydrocarbons; alternatively, $C_1$ to $C_{10}$ halogenated aliphatic hydrocarbons; or alternatively, $C_1$ to $C_5$ halogenated aliphatic hydrocarbons. Non-limiting examples of such halogenated aliphatic hydrocarbons, which may be utilized as a solvent, include carbon tetrachloride, chloroform, methylene chloride, dichloroethane, trichloroethane, and combinations thereof. Halogenated aromatic hydrocarbons, which may be useful as a solvent, include $C_6$ to $C_{20}$ halogenated aromatic hydrocarbons; or alternatively, $C_6$ to $C_{10}$ halogenated aromatic hydrocarbons. Non-limiting examples of suitable halogenated aromatic hydrocarbons include chlorobenzene, dichlorobenzene, and combinations thereof.

If a solvent is used for the reaction between the unsaturated ester and hydrogen sulfide, the quantity of solvent can be any amount that facilitates the reaction. In some embodiments, the mass of the solvent is less than 30 times the mass of the unsaturated ester. In other embodiments, the mass of the solvent is less than 20 times the mass of the unsaturated ester; alternatively, less than 15 times the mass of the unsaturated ester; alternatively, less than 10 times the mass of the unsaturated ester; or alternatively, less than 5 times the mass of the unsaturated ester. In other embodiments, the mass of the solvent is from 2 times to 20 times the mass of the unsaturated ester; alternatively, from 3 times to 15 times the mass of the unsaturated ester; alternatively, 4 times to 15 times the mass of the unsaturated ester; or alternatively, from 5 times to 10 times the mass of the unsaturated ester.

The process to produce the desired thiol ester composition may include a step to remove excess or residual hydrogen sulfide and/or the optional solvent after reacting the hydrogen sulfide and the unsaturated ester molecules having a terminal carbon-carbon double bond. For example, the thiol ester composition may be vacuum stripped at a temperature ranging between 25° C. and 250° C.; or, alternatively, between 50° C. and 200° C. In some embodiments, the thiol ester composition may be subjected to wiped film evaporation. In other embodiments, the thiol ester composition may be sparged with an inert gas to remove hydrogen sulfide, at a temperature between 25° C. and 250° C.; or, alternatively, between 50° C. and 200° C. The inert gas may be nitrogen, or any other suitable inert gas, such as argon. Generally, the stripped or sparged thiol ester composition may include less than 0.1 weight percent hydrogen sulfide. In other embodiments, the stripped or sparged thiol ester composition may include less than 0.05 weight percent hydrogen sulfide; alternatively, less than 0.025 weight percent hydrogen sulfide; or alternatively, less than 0.01 weight percent hydrogen sulfide.

Process for Making α-Hydroxy Thiol Ester Compositions

The α-hydroxy thiol ester molecules having terminal α-hydroxy thiol ester groups or the α-hydroxy thiol ester compositions comprising, or consisting essentially of, the aforementioned α-hydroxy thiol ester molecules may be formed or produced by contacting hydrogen sulfide and epoxide ester molecules having a terminal epoxide groups or epoxide ester composition comprising, or consisting essentially of, epoxide ester molecules having a terminal epoxide groups.

Generally the method for producing the α-hydroxy thiol ester molecules (or composition comprising, or consisting essentially of α-hydroxy thiol ester molecules) comprises a) contacting hydrogen sulfide and epoxide ester molecules having a terminal epoxide group (or composition comprising, or consisting essentially of, epoxide ester molecules having terminal epoxide groups), and b) forming α-hydroxy thiol ester molecules having terminal α-hydroxy thiol groups (or the α-hydroxy thiol ester composition comprising, or consisting essentially of, α-hydroxy thiol ester molecules having terminal α-hydroxy thiol groups). Generally, the α-hydroxy thiol ester molecules having α-hydroxy thiol groups (or the α-hydroxy thiol ester composition comprising, or consisting essentially of, α-hydroxy thiol ester molecules having terminal α-hydroxy thiol groups) are formed at conditions capable of forming α-hydroxy thiol ester molecules having α-hydroxy thiol groups (or the α-hydroxy thiol ester composition comprising, or consisting essentially of, α-hydroxy thiol ester molecules having terminal α-hydroxy thiol groups). The processes described herein can be applied to any epoxide ester molecules having a terminal epoxide group (or epoxide ester composition comprising, or consisting essentially of, epoxide ester molecules having a terminal epoxide group) described herein. The processes described herein can be used to produce any α-hydroxy thiol ester molecules having terminal α-hydroxy thiol groups (or α-hydroxy thiol ester compositions comprising, or consisting essentially of, α-hydroxy thiol ester molecules having terminal α-hydroxy thiol groups) described herein. The process for producing the and α-hydroxy thiol molecules (or the α-hydroxy thiol ester composition) can also include any additional process steps or process conditions described herein.

The molar ratio of hydrogen sulfide to terminal epoxide groups utilized in the process to produce the α-hydroxy thiol ester molecules (or α-hydroxy thiol ester composition) can be any molar ratio that produces the desired α-hydroxy thiol ester molecules (or α-hydroxy thiol ester composition). For example, the process may use a molar ratio of the hydrogen sulfide to terminal epoxide groups greater than 2. In other embodiments, the molar ratio of hydrogen sulfide to terminal epoxide groups may be greater than 5; alternatively, greater than 10; alternatively, greater than 15; or alternatively, greater than 20. In other embodiments, the molar ratio of hydrogen sulfide to terminal epoxide groups may be from 2 to 500; alternatively, from 5 to 200; alternatively, from 10 to 100; or alternatively, from 100 to 200.

The reaction between the epoxide ester molecules and hydrogen sulfide may be catalyzed. In some embodiments, the catalyst may be a heterogeneous catalyst; alternatively, or a homogeneous catalyst. Examples of suitable catalysts are described herein. Additional types of suitable catalysts will be apparent to those of skill in the art and are to be considered within the scope of the present invention.

The reaction of the epoxide ester molecules having a terminal epoxide group and hydrogen sulfide may be performed in a batch reactor or a continuous reactor. Continuous reactors that may be utilized include continuous stirred reactors, fixed bed reactors, and the like. Batch reactors that may be utilized include autoclave reactors. Other types of batch and continuous reactors that can be used in embodiments of the present invention will be apparent to those of skill in the art and are to be considered within the scope of the present invention.

If a continuous reactor is used for the reaction, an hourly space velocity feed weight of the epoxide ester molecules having terminal epoxide group may range from 0.1 to 5. Alternatively, the hourly space velocity feed weight may range from 0.1 to 5; alternatively, from 0.1 to 2. Alternatively, the unsaturated ester molecule weight hourly space velocity may be about 0.1; alternatively, the weight hourly space velocity of the epoxide ester molecules having terminal epoxide groups may be about 0.25; or alternatively, about 2.

The reaction between the hydrogen sulfide and the epoxide ester molecules having terminal epoxide groups may be performed at any temperature capable of forming the desired α-hydroxy thiol ester molecules (α-hydroxy thiol ester composition). In some embodiments, the epoxide ester molecules having terminal epoxide groups and hydrogen sulfide may be reacted at a temperature greater than –20° C. In other embodiments, the reaction temperature may be greater than 0° C.; alternatively, greater than 20° C.; alternatively, greater than 50° C.; or alternatively, greater than 80° C. In yet other embodiments, the reaction temperature may range from –20° C. to 200° C.; alternatively, from 20° C. to 170° C.; or alternatively, from 80° C. to 140° C.

The reaction between the hydrogen sulfide and the epoxide ester molecules having terminal epoxide groups may be performed at any reaction pressure that maintains a substantial portion of the hydrogen sulfide in a liquid state. In some embodiments, the reaction pressure may range from 100 psig to 2000 psig. In other embodiments, the reaction pressure may range from 150 to 1000 psig; or alternatively, from 200 to 600 psig.

The time required for the reaction of the epoxide ester molecules having terminal epoxide group and hydrogen sulfide can be any time required to form the desired α-hydroxy thiol molecules having a terminal α-hydroxy thiol group (or α-hydroxy thiol composition comprising, or consisting essentially of α-hydroxy thiol molecules having a terminal α-hydroxy thiol group). Generally, the time required for the reaction of the epoxide ester molecules and hydrogen sulfide is at least 15 minutes. In some embodiments, the time required for the reaction of the epoxide ester molecules and hydrogen sulfide ranges from 15 minutes to 72 hours; alternatively, from 30 minutes to 48 hours; alternatively, from 45 minutes to 36 hours.

The reaction between the hydrogen sulfide and the epoxide ester molecules having terminal epoxide groups may occur in the presence of a solvent. However, the reaction may also be performed in the substantial absence of a solvent. When the solvent is present, the solvent may be a selected from aromatic hydrocarbons, aliphatic hydrocarbons, organic alcohols, organic ethers, organic carbonates, organic esters, halogenated aliphatic hydrocarbons, aromatic hydrocarbons, halogenated aromatic hydrocarbons, and combinations thereof. Aliphatic hydrocarbons, which may be useful as a solvent, include $C_4$ to $C_{20}$ hydrocarbons, or alternatively, $C_5$ to $C_{10}$ hydrocarbons, and may be cyclic or acyclic and include linear or branched isomers, unless otherwise specified. Non-limiting examples of suitable acyclic aliphatic solvents include pentane, hexane, heptane, octane, and combinations thereof. Non-limiting examples of suitable cyclic aliphatic solvents include cyclohexane, methyl cyclohexane, and combinations thereof. Aromatic hydrocarbons, which may be useful as a solvent, include $C_6$ to $C_{20}$ aromatic hydrocarbons; or alternatively, $C_6$ to $C_{10}$ aromatic hydrocarbons. Non-limiting examples of suitable aromatic hydrocarbons include benzene, toluene, xylene (including ortho-xylene, meta-xylene, para-xylene, or mixtures thereof), and ethylbenzene, or combinations thereof. Organic alcohols, organic ethers, organic carbonates, organic esters, which may be useful as a solvent include $C_2$ to $C_{20}$ organic alcohols, organic ethers, organic carbonates, organic esters, organic ketones, or organic aldehydes; alternatively, $C_2$ to $C_{10}$ organic alcohols, organic ethers, organic carbonates, organic esters, organic ketones, or organic aldehydes; or alternatively, $C_2$ to $C_5$ organic alcohols, organic ethers, organic carbonates, organic esters, organic ketones, or organic aldehydes. Non-limiting examples of suitable alcohol solvents include methanol, 1-propanol, 2-propanol, 1-butanol, 2-butanol, 2-methyl-2-propanol, or mixtures thereof. Suitable ether solvents may be cyclic or acyclic. Non-limiting examples of suitable ethers which may be useful as a solvent include dimethyl ether, diethyl ether, methyl ethyl ether, monoethers or diethers of glycols (e.g., dimethyl glycol ether), furans, substituted furans, dihydrofuran, substituted dihydrofurans, tetrahydrofuran (THF), substituted tetrahydrofurans, tetrahydropyrans, substituted tetrahydropyrans, 1,3-dioxanes, substituted 1,3-dioxanes, 1,4-dioxanes, substituted 1,4-dioxanes, or mixtures thereof. In an embodiment, each substituent of a substituted furan, substituted dihydrofuran, substituted tetrahydrofuran, substituted tetrahydropyran, substituted 1,3-dioxane, or substituted 1,4-dioxane, can be a $C_1$ to $C_5$ alkyl group. Non-limiting examples of suitable organic carbonates, which may be utilized as a solvent, include ethylene carbonate, propylene carbonate, diethyl carbonate, diethyl carbonate, and combinations thereof. Non-limiting examples of suitable esters, which may be utilized as a solvent, include ethyl acetate, propyl acetate, butyl acetate, isobutyl isobutyrate, and combinations thereof. Halogenated aliphatic hydrocarbons, which may be useful as a solvent, include $C_1$ to $C_{15}$ halogenated aliphatic hydrocarbons; alternatively, $C_1$ to $C_{10}$ halogenated aliphatic hydrocarbons; or alternatively, $C_1$ to $C_5$ halogenated aliphatic hydrocarbons. Non-limiting examples of such halogenated aliphatic hydrocarbons, which may be utilized as a solvent, include carbon tetrachloride, chloroform, methylene chloride, dichloroethane, trichloroethane, and combinations thereof. Halogenated aromatic hydrocarbons, which may be useful as a solvent, include $C_6$ to $C_{20}$ halogenated aromatic hydrocarbons; or alternatively, $C_6$ to $C_{10}$ halogenated aromatic hydrocarbons. Non-limiting examples of suitable halogenated aromatic hydrocarbons include chlorobenzene, dichlorobenzene, and combinations thereof.

When a solvent is used for the reaction between the hydrogen sulfide and the epoxide ester molecules having terminal epoxide groups, any amount that may facilitate the reaction may be used. In some embodiments, the mass of the solvent may be less than 30 times the mass of the epoxide ester molecules having terminal epoxide groups. In other embodiments, the mass of the solvent may be less than 20 times the mass of the epoxide ester molecules having terminal epoxide groups; alternatively, less than 15 times the mass of epoxide ester molecules having terminal epoxide groups; alternatively, less than 10 times the mass of the epoxide ester molecules having terminal epoxide groups; or alternatively, less than 5 times the mass of the epoxide ester molecules having terminal epoxide groups. In other embodiments, the mass of the solvent is from 2 times to 20 times the mass of the epoxide ester molecules having terminal epoxide groups; alternatively, from 3 times to 15 times the mass of the epoxide ester molecules having terminal epoxide groups; alternatively; 4 times to 15 times the mass of the epoxide ester molecules having terminal epoxide groups; or alternatively, from 5 times to 10 times the mass of the epoxide ester molecules having terminal epoxide groups.

The process to produce the α-hydroxy thiol ester molecules having a terminal α-hydroxy thiol group may include a step to remove excess or residual hydrogen sulfide and/or the optional solvent after reacting the hydrogen sulfide and the epoxide ester molecules having a terminal epoxide group. For example, the α-hydroxy thiol ester composition may be vacuum stripped at a temperature ranging between 25° C. and 250° C.; or, alternatively, between 50° C. and 200° C. In some embodiments, the α-hydroxy thiol ester composition may be subjected to wiped film evaporation. In other embodiments, the α-hydroxy thiol ester composition may be sparged with an inert gas to remove hydrogen sulfide, at a temperature between 25° C. and 250° C.; or, alternatively, between 50° C. and 200° C. The inert gas may be nitrogen, or any other suitable inert gas, such as argon. Generally, the stripped or sparged α-hydroxythiol thiol ester composition may include less than 0.1 weight percent hydrogen sulfide. In other embodiments, the stripped or sparged α-hydroxy thiol ester composition may include less than 0.05 weight percent hydrogen sulfide; alternatively, less than 0.025 weight percent hydrogen sulfide; or alternatively, less than 0.01 weight percent hydrogen sulfide.

Process for Making Cross-Linked Thiol Ester Compositions

As an embodiment of the present invention, a process for producing a cross-linked thiol ester composition is advantageously provided. In some embodiments, the process to produce the cross-linked thiol ester composition comprises contacting a thiol ester composition with an oxidizing agent and reacting the thiol ester composition and an oxidizing agent to form the thiol ester oligomer having at least two thiol ester monomers connected by a polysulfide linkage having the structure $—S_Q—$, wherein Q is an integer greater than 1. Alternatively, the process to produce the cross-linked thiol ester composition comprises contacting a α-hydroxy thiol ester composition comprising with an oxidizing agent and reacting the α-hydroxy thiol ester composition and an oxidizing agent to form the α-hydroxy thiol ester oligomer having at least two thiol ester monomers connected by a polysulfide linkage having the structure $—S_Q—$, wherein Q is an integer greater than 1. The disclosed methods may be applied to any thiol ester composition (or thiol ester composition) or hydroxy thiol ester molecules (or α-hydroxy thiol ester composition) described herein to produce any cross-linked thiol ester molecules (or cross-linked thiol ester composition) or cross-linked α-hydroxy thiol ester molecules (or cross-linked α-hydroxy thiol ester composition) described herein. The process to produce the cross-linked thiol ester molecules (or cross-linked thiol ester composition) or cross-linked α-hydroxy thiol ester (or cross-linked α-hydroxy thiol ester composition) can also include any additional process steps or process conditions as described herein.

In an aspect, the oxidizing agent can be elemental sulfur, oxygen, or hydrogen peroxide. In some embodiments, the oxidizing agent can be elemental sulfur. In other embodiments, the oxidizing agent can be oxygen. In some oxygen oxidizing agent embodiments, the oxidizing agent is air. In further embodiments, the oxidizing agent is hydrogen peroxide.

When elemental sulfur is used as the oxidizing agent, the quantity of elemental sulfur utilized to form the cross-linked thiol ester molecules (or cross-linked thiol ester composition) or cross-linked α-hydroxy thiol ester (or cross-linked α-hydroxy thiol ester composition) is determined as a function of the thiol sulfur content of the cross-linked thiol ester molecules (or cross-linked thiol ester composition) or cross-linked α-hydroxy thiol ester (or cross-linked α-hydroxy thiol ester composition), respectively. In an aspect, the weight ratio of elemental sulfur to thiol sulfur in the thiol ester composition or α-hydroxy thiol ester composition is at least 0.5. In some embodiments, the weight ratio of elemental sulfur to thiol sulfur in the thiol ester composition or α-hydroxy thiol ester composition is at least 5; alternatively, at least 10, alternatively, at least 15, or alternatively, at least 20. In other embodiments, the weight ratio of elemental sulfur to thiol sulfur in the thiol ester composition or α-hydroxy thiol ester composition ranges from 0.5 to 32; alternatively, ranges from 1 to 24; alternatively, ranges from 2 to 16; or alternatively, ranges from 3 to 10.

In an aspect, the reaction of the thiol ester molecule or α-hydroxy thiol ester molecules and elemental sulfur occurs in the presence of a catalyst. The catalyst can be any catalyst that catalyzes the formation of the polysulfide linkage between at least two thiol ester monomers. In some embodiments, the catalyst is an amine. In further embodiments, the catalyst is a tertiary amine.

The formation of the cross-linked thiol ester molecules (or cross-linked thiol ester composition) or cross-linked α-hydroxy thiol ester (or cross-linked α-hydroxy thiol ester composition) can occur in a batch reactor or a continuous reactor, as described herein. The formation of the cross-linked thiol ester molecules (or cross-linked thiol ester composition) or cross-linked α-hydroxy thiol ester (or cross-linked α-hydroxy thiol ester composition) can occur at any temperature capable of forming the thiol ester. In some embodiments, the formation of the cross-linked thiol ester molecules (or crosslinked thiol ester composition) or cross-linked α-hydroxy thiol ester (or cross-linked α-hydroxy thiol ester composition) can occur at a temperature greater than 25° C. In other embodiments, the formation of the cross-linked thiol ester composition or cross-linked α-hydroxy thiol ester composition can occurs at a temperature greater than 50° C.; alternatively, greater than 70° C.; or alternatively, greater than 80° C. In yet other embodiments, the formation of the cross-linked thiol ester molecules (or cross-linked thiol ester composition) or cross-linked α-hydroxy thiol ester (or cross-linked α-hydroxy thiol ester composition) occurs at a temperature from 25° C. to 150° C.; alternatively, from 50° C. to 150° C.; alternatively, from 70° C. to 120° C.; or alternatively, from 80° C. to 110° C.

The time required to form the c cross-linked thiol ester molecules (or cross-linked thiol ester composition) or cross-linked α-hydroxy thiol ester (or cross-linked α-hydroxy thiol ester composition) can be any time required to form the desired cross-linked thiol ester molecules or α-hydroxy thiol ester molecules. Generally, the time required to form the cross-linked thiol ester molecules (or cross-linked thiol ester composition) or cross-linked α-hydroxy thiol ester (or cross-linked α-hydroxy thiol ester composition) is at least 15 minutes. In some embodiments, the time required to form the cross-linked thiol ester molecules (or cross-linked thiol ester composition) or cross-linked α-hydroxy thiol ester (or cross-linked α-hydroxy thiol ester composition) is at least 30 minutes; alternatively, at least 1 hour; or alternatively, at least 2 hours. In yet other embodiments, the time required to form the cross-linked thiol ester molecules (or cross-linked thiol ester composition) or cross-linked α-hydroxy thiol ester (or cross-linked α-hydroxy thiol ester composition) ranges from 15 minutes to 72 hours; alternatively, from 30 minutes to 48 hours; alternatively, from 1 hour minutes to 36 hours; or alternatively, from 2 hours and 24 hours.

In embodiments, the process to produce the cross-linked thiol ester molecules (or cross-linked thiol ester composition) or cross-linked α-hydroxy thiol ester (or cross-linked α-hydroxy thiol ester composition) further comprises a step to remove residual hydrogen sulfide. In some embodiments the cross-linked thiol ester composition or cross-linked α-hydroxy thiol ester composition is vacuum stripped. In some embodiments, the cross-linked thiol ester composition or cross-linked α-hydroxy thiol ester composition is vacuum striped at a temperature between 25° C. and 250° C.; alternatively, between 50° C. and 200° C.; or alternatively, 75 and 150° C. In some embodiments, the cross-linked thiol ester composition or cross-linked α-hydroxy thiol ester composition is sparged with an inert gas to remove residual hydrogen sulfide. In other embodiments, the cross-linked thiol ester composition or cross-linked α-hydroxy thiol ester composition is sparged with an inert gas at a temperature between 25° C. and 250° C.; alternatively, between 50° C. and 200° C.; or alternatively, between 75 and 150° C. In yet other embodiments, the vacuum stripping is performed while sparging the cross-linked thiol ester composition or cross-linked α-hydroxy thiol ester composition with an inert gas. In yet other embodiments, the vacuum stripping is performed while sparging the cross-linked thiol ester composition or cross-linked α-hydroxy thiol ester composition an inert gas at a temperature between 25° C. and 250° C.; alternatively, between 50° C. and 200° C.; or alternatively, 75 and 150° C. In some embodiments, the inert gas is nitrogen.

Generally, the stripped or sparged cross-linked thiol ester composition or cross-linked α-hydroxy thiol ester composition comprises less than 0.1 weight percent hydrogen sulfide. In other embodiments, the stripped or sparged thiol-containing ester composition or cross-linked α-hydroxy thiol ester composition comprises less than 0.05 weight percent hydrogen sulfide; alternatively, less than 0.025 weight percent hydrogen sulfide; or alternatively, less than 0.01 weight percent hydrogen sulfide.

Process for Making Terminal Epoxide Ester Compositions

The unsaturated ester composition comprising, or consisting essentially of, unsaturated ester molecules having a terminal carbon-carbon double bond may be used to form epoxide ester composition comprising epoxide ester molecules having a terminal epoxide group by reacting the unsaturated ester molecules having a terminal carbon-carbon double bond with an oxygen containing compound, optionally in the presence of a catalyst. Generally the method for producing the epoxide ester molecules (or composition comprising, or consisting essentially of epoxide ester molecules) comprises a) contacting unsaturated ester molecules having terminal carbon-carbon double bonds (or composition comprising, or consisting essentially of, unsaturated ester molecules having terminal carbon-carbon double bonds) and an oxygen containing compound and b) forming epoxide ester molecules having terminal epoxide groups (or the epoxide ester composition comprising, or consisting essentially of, epoxide ester molecules having terminal epoxide groups). Generally, the epoxide ester molecules having epoxide groups (or the epoxide ester composition comprising, or consisting essentially of, epoxide ester molecules having terminal epoxide groups) are formed at conditions capable of forming epoxide ester molecules having epoxide groups (or the epoxide ester composition comprising, or consisting essentially of, epoxide ester molecules having terminal epoxide groups). The method of producing the epoxide ester molecules having terminal epoxide groups (or epoxide ester composition comprising, or consisting essentially of, the epoxide ester molecules having terminal epoxide groups) can also include any additional process steps or process conditions described herein.

A number of techniques that are well known in the art may be used to perform the epoxidation. Some exemplary techniques include reaction of the compounds having the unsaturated ester molecules having a terminal carbon-carbon double bond with a peracid (e.g. peracetic acid or performic acid, or the reaction of the compounds having terminal alkene groups with a peracid generated in situ (e.g. peracetic acid or performic acid created by reacting acetic, or formic acid, with hydrogen peroxide in the presence of a strong acid such as sulfur acid or methanesulfonic acid).

For example, the cross-counter flow process described in U.S. Pat. No. 4,584,390, herein included by reference in its entirety, may be used. This process uses a sequence of tank reactors to implement a countercurrent staged reaction in which, at each stage, two phases (e.g., organic and aqueous) are stirred together and then separated in a phase separator before being sent (in opposite directions) to the next reactor. The organic phase at each stage includes the terminal alkene composition which is being sequentially epoxidized, while the aqueous phase includes hydrogen peroxide and a formic acid (e.g., a performic acid). Each reaction is carried out at a temperature of about 50° C. to about 80° C., while each phase separation is carried out at a temperature in the range of 15° C. to 60° C. One of ordinary skill in the art will recognize that other carboxylic acids (e.g., acetic acid, among others) may be used in this process, forming percarboxylic acids. Further, small amounts of other materials (e.g., sulfuric acid, among others) may be added as catalysts.

A mixture of epoxide ester molecules having a terminal epoxide group may be formed in the epoxidation reaction.

The epoxide ester molecules (or epoxide ester composition comprising, or consisting essentially of epoxide ester molecules having a terminal epoxide group), may have any feature described herein and may be produced form any unsaturated ester molecules having a terminal carbon-carbon double bond (or unsaturated ester composition comprising, or consisting essentially of unsaturated ester molecules having a terminal carbon-carbon double bond) described herein.

Unsaturated Ester Molecules Having Terminal Carbon-Carbon Double Bonds and Processes for Making them An intermediate in producing the products described herein are unsaturated ester molecules having terminal carbon-carbon double bonds and unsaturated ester composition comprising unsaturated ester molecules having terminal carbon-carbon double bonds. The unsaturated ester molecules having terminal carbon-carbon double bonds (or unsaturated ester composition comprising, or consisting essentially of, unsaturated ester molecules having terminal carbon-carbon double bonds) are described herein along with a process by which they may be prepared.

Unsaturated Ester Molecules Having Terminal Carbon-Carbon Double Bonds

In an aspect, the present invention relates to unsaturated ester compositions comprising, or consisting essentially of unsaturated ester molecules having terminal carbon-carbon double bonds. In an aspect the unsaturated ester molecules having terminal carbon-carbon double bonds may be described as comprising, consisting essentially of, one or more functional group present in the unsaturated ester molecules of the unsaturated ester composition. Each of the functional groups that may be present in the unsaturated ester molecules having terminal carbon-carbon double bonds are independently described herein and may be utilized in any combination to described the unsaturated ester molecules having terminal carbon-carbon double bonds.

The independent functional groups that can be utilized to describe the thiol ester molecules having terminal carbon-carbon double bonds include the number of (or average number of) ester groups per unsaturated ester molecule, the number of (or average number of) terminal carbon-carbon double bonds per unsaturated ester molecule, and the ratio of (or average ratio of) terminal carbon-carbon double bonds to ester group. In some embodiments, the unsaturated ester molecules having terminal carbon-carbon double bonds may be substantially devoid of hydroxyl groups. In other embodiments, the unsaturated ester molecules having terminal carbon-carbon double bonds may be substantially devoid of functional groups other than ester groups and carbon-carbon double bonds (terminal or otherwise).

The unsaturated ester molecules having terminal carbon-carbon double bonds may be produced using the methods described herein. It should be noted that the production method may utilize feedstocks containing more than one structure. This fact, combined with feedstock reactivity differences and statistical probability, dictate that the unsaturated esters having terminal carbon-carbon double bonds may have many different structures. Thus, each unsaturated thiol ester molecule having terminal carbon-carbon double bonds may not have the same number of functional groups, the same ratios of functional groups, and/or the same additional features. Consequently, the number of functional group, ratios of functional groups, and/or additional features of the unsaturated ester molecules having terminal carbon-carbon double bonds may be referred to as an average within the unsaturated ester composition.

In an embodiment, the unsaturated ester molecules having terminal carbon-carbon double bonds may have at least 2 ester groups; alternatively at least 3 ester groups; or alternatively, at least 4 ester groups. In other embodiments, the unsaturated ester molecules having terminal carbon-carbon double bonds have from 2 to 8 ester groups; alternatively, 3 to 6 ester groups; alternatively, 3 to 4 ester groups; alternatively, only 3 ester groups; or alternatively, only 4 ester groups. In further embodiments, the unsaturated ester molecules having terminal carbon-carbon double bonds have an average of at least 2 ester groups per unsaturated ester molecule; alternatively, an average of at least 2.5 ester groups per unsaturated ester molecule; or alternatively, an average of at least 3 ester groups per unsaturated ester molecule. In yet further embodiments, the unsaturated ester molecules having terminal carbon-carbon double bonds have an average of from 2 to 8 ester groups per unsaturated ester molecule; alternatively, an average of from 2 to 7 ester groups per unsaturated ester molecule; alternatively, an average of from 2.5 to 5 ester groups per unsaturated ester molecule; or alternatively, an average of from 3 to 4 ester groups per unsaturated ester molecule. In yet other embodiments, the unsaturated ester molecules having terminal carbon-carbon double bonds have an average of about 3 ester groups per unsaturated ester molecule; or alternatively, an average of about 4 ester groups per unsaturated ester molecule.

In an embodiment, the unsaturated ester molecules having terminal carbon-carbon double bonds of the thiol ester composition have at least 2 terminal carbon-carbon double bonds; alternatively, at least terminal carbon-carbon double bonds; or alternatively, at least 4 terminal carbon-carbon double bonds. In other embodiments, the unsaturated ester molecules having terminal carbon-carbon double bonds have from 2 to 8 terminal carbon-carbon double bonds; alternatively, 3 to 6 terminal carbon-carbon double bonds; alternatively, 3 to 4 terminal carbon-carbon double bonds; alternatively, only 3 terminal carbon-carbon double bonds; or alternatively, only 4 terminal carbon-carbon double bonds. In further embodiments, the unsaturated ester molecules having terminal carbon-carbon double bonds have an average of at least 1.5 terminal carbon-carbon double bonds per unsaturated ester molecule; alternatively, an average of at least 2.5 terminal carbon-carbon double bonds per unsaturated ester molecule; or alternatively, an average of at least 3 terminal carbon-carbon double bonds per unsaturated ester molecule. In yet further embodiments, the unsaturated ester molecules having terminal carbon-carbon double bonds have an average of from 1.5 to 8 terminal carbon-carbon double bonds per unsaturated ester molecule; alternatively, an average of from 2 to 7 terminal carbon-carbon double bonds per unsaturated ester molecule; alternatively, an average of from 2.5 to 5 terminal carbon-carbon double bonds per unsaturated ester molecule; or alternatively, an average of from 3 to 4 terminal carbon-carbon double bonds per unsaturated ester molecule. In yet other embodiments, the unsaturated ester molecules having terminal carbon-carbon double bonds have an average of about 3 terminal carbon-carbon double bonds per unsaturated ester molecule; or alternatively, an average of about 4 terminal carbon-carbon double bonds per unsaturated ester molecule.

In an embodiment, the unsaturated ester molecules having terminal carbon-carbon double bonds may contain internal carbon-carbon double bonds. These internal carbon-carbon double bonds may result from incomplete conversion of the feedstock. In some embodiments, the average ratio of terminal carbon-carbon double bonds to internal carbon-carbon double bonds is less than 1:5; alternatively, less than 1:7; or alternatively, less than 1:10.

In an aspect, the unsaturated ester molecules within the unsaturated ester compositions may be described as having ester linkages comprising a residue of a polyol and a carboxylic acid residue having a terminal carbon-carbon double bond. Additional features of the residue of the polyol and carboxylic acid residue having a terminal carbon-carbon double bond are independently describe herein and may be utilized in any combination to further describe the unsaturated ester molecules.

The unsaturated ester molecules described as having ester linkages comprising a residue of a polyol and a carboxylic acid residue having a terminal carbon-carbon double bond may be produced from any unsaturated esters described herein. It should be noted that the feedstock unsaturated esters may have multiple double bonds, have double bonds at different positions, and may contain many different unsaturated ester molecules. This fact, combined with carbon-carbon double bond reactivity and/or statistical probability, dictate that each unsaturated thiol ester molecule having ester linkages comprising a residue of a polyol and a carboxylic acid residue having a terminal carbon-carbon double bond may not have the same structure. Thus, particular features of the unsaturated ester molecules having ester linkages comprising a residue of a polyol and a carboxylic acid residue having a terminal carbon-carbon double bond may be described as an average per unsaturated ester molecule.

In an embodiment, the unsaturated ester molecules having ester linkages comprising a residue of a polyol and carboxylic acid residues having a terminal carbon-carbon double bond. The residue of the polyol and the carboxylic acid residue having a terminal carbon-carbon double bond independent elements of unsaturated ester molecules having ester linkages. Consequently, the features of the residue of the polyol and the carboxylic acid having a terminal carbon-carbon double bond are independently described herein and may be used in any combination to describe the unsaturated ester molecules having ester linkages comprising a residue of a polyol and at least two carboxylic acid residues having a terminal carbon-carbon double bond.

The carboxylic acid residue having a terminal carbon-carbon double bond may be further described by its structural features. These structural features are independently described herein and may be utilized in any combination to describe the carboxylic acid residue having a terminal carbon-carbon double bond of the unsaturated ester molecules having ester linkages comprising a residue of a polyol and carboxylic acid residues having a terminal carbon-carbon double bond.

In an embodiment, the carboxylic acid residue having the terminal carbon-carbon double bond is linear. In some embodiments, the carboxylic acid residue having the terminal carbon-carbon double bond is branched.

In an embodiment, the carboxylic acid residue having the terminal carbon-carbon double bond may have at least 4 carbon atoms; alternatively, at least 6 carbon atoms; or alternatively, at least 8 carbon atoms. In some embodiments, the carboxylic acid residue having the terminal carbon-carbon double bond may have from 4 to 20 carbon atoms; alternatively, from 6 to 18 carbon atoms; alternatively, from 8 to 14 carbon atoms; alternatively, from 10 to 11 carbon atoms; alternatively, only 10 carbon atoms; or alternatively, only 11 carbon atoms. In some embodiments, the carboxylic acid equivalent having a terminal carbon-carbon double bond may be a mixture of carboxylic acid residues having a terminal carbon-carbon double bond. In such embodiments, the carboxylic acid residues having a terminal carbon-carbon double bond may have an average of at least 6 carbon atoms; or alternatively, at least 8 carbon atoms; alternatively, from 6 to 18 carbon atoms; alternatively, from 8 to 14 carbon atoms; alternatively, from 10 to 11 carbon atoms; alternatively, about 10 carbon atoms; or alternatively, about 11 carbon atoms.

In an embodiment, the carboxylic acid residue having the terminal carbon-carbon double bond is substantially devoid of other functional groups. In further embodiments, the carboxylic acid residue having the terminal carbon-carbon double bond is devoid of other functional groups (i.e. that outside of the terminal carbon-carbon double bond and the carbonyl group forming the ester linkage, the carboxylic acid contains only carbon and hydrogen).

In an embodiment, the carboxylic acid residues having a terminal carbon-carbon double bond epoxide group may have Structure CRU 1.

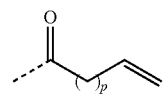

CRU 1 wherein p may be positive integer ranging from 1 to 17; alternatively from 3 to 15; alternatively, from 5 to 11; or alternatively 7 to 8. In some embodiments, p may be 7 or alternatively 8. In other embodiments, p may represent an average number (whole or fractional) of carbon atom ranging from 1 to 17; alternatively from 3 to 15; alternatively, from 5 to 11; alternatively 7 to 8; alternatively about 7; or alternatively, about 8. Within the carboxylic acid residue structure CRU 1 the dashed line is the bond to the oxygen atom of the ester linkage.

Suitable carboxylic acid residues having a terminal carbon-carbon double bond include 3-butenoic acid residue, a 4-pentenoic acid residue, a 5-hexenoic acid residue, a 6-heptenoic acid residue, a 7-octenoic acid residue, a 8-nonenoic acid residue, a 9-decenoic acid residue, a 10-undecenoic acid residue, a 11-dodecenoic acid residue, a 12-tridecenoic acid residue, a 13-tetradecenoic acid residue, a 14-pentadecenoic acid residue, a 15-hexadecenoic acid residue, a 16-heptadecenoic acid residue, a 17-octadecenoic acid residue, a 18-nonadecenoic acid residue, a 19-eicosene, or any combination thereof. In some embodiments, the carboxylic acid residues having a thiol group located on the terminal carbon atom include a 5-hexenoic acid residue, a 6-heptenoic acid residue, a 7-octenoic acid residue, a 8-nonenoic acid residue, a 9-decenoic acid residue, a 10-undecenoic acid residue, a 11-dodecenoic acid residue, a 12-tridecenoic acid residue, a 13-tetradecenoic acid residue, a 14-pentadecenoic acid residue, a 15-hexadecenoic acid residue, a 16-heptadecenoic acid residue, a 17-octadecenoic acid residue, or any combination thereof; alternatively, a 7-octenoic acid residue, a 8-nonenoic acid residue, a 9-decenoic acid residue, a 10-undecenoic acid residue, a 11-dodecenoic acid residue, a 12-tridecenoic acid residue, a 13-tetradecenoic acid residue, or any combination thereof; or alternatively, 9-decenoic acid residue, a 10-undecenoic acid residue, or any combination thereof. In other embodiments, the carboxylic acid residues having a terminal carbon-carbon double bond may be a 5-hexenoic acid residue; alternatively, a 6-heptenoic acid residue; alternatively, a 7-octenoic acid residue; alternatively, a 8-nonenoic acid residue; alternatively, a 9-decenoic acid residue; alternatively, a 10-undecenoic acid residue; alternatively, a 11-dodecenoic acid residue; alternatively, a 12-tridecenoic acid residue; alternatively, a 13-tetradecenoic acid residue; alternatively, a 14-pentadecenoic acid residue; alternatively, a 15-hexadecenoic acid residue; alternatively, a 16-heptadecenoic acid residue; or alternatively, a 17-octadecenoic acid residue.

The residue of the polyol may be further described by its structural features. These structural features are independently described herein and may be utilized in any combination to describe the residue of the polyol of the unsaturated ester molecules having ester linkages comprising a residue of a polyol and carboxylic acid residues having a terminal carbon-carbon double bond.

In an embodiment, residue of the polyol may have had 2 to 20 carbon atoms. In some embodiments, the residue of the polyol may have 2 to 12 carbon atoms; alternatively, 2 to 8 carbon atoms; or alternatively, 2 to 5 carbon atoms. In further embodiments, the polyol may be a mixture of polyols having an average of 2 to 20 carbon atoms per polyol molecule; alternatively, an average of from 2 to 12 carbon atoms per polyol molecule; alternatively, an average of 2 to 8 carbon atoms; alternatively an average of 2 to 5 carbon atoms per polyol molecule.

In an embodiment, the polyol of the residue of the polyol may have had 2 to 8 hydroxyl group; alternatively, 3 to 6 hydroxyl groups; alternatively, 2 to 4 hydroxyl groups; alternatively, 4 to 8 hydroxyl groups; alternatively, only 3 hydroxyl groups; alternatively, only 4 hydroxyl groups; alternatively, only 5 hydroxyl groups; or alternatively, only 6 hydroxyl groups. In other embodiments, mixtures of residue of polyol may be used and the mixture of polyols of the residues of the polyols may have had an average at least 2 hydroxyl groups per polyol molecule; alternatively, at least 2.5 hydroxyl groups per polyol molecule; alternatively, 2.5 to 8 hydroxyl groups per polyol molecule; alternatively, an average of 2 to 6 hydroxyl groups per polyol molecule; alternatively, an average of 2.5 to 5 hydroxyl groups per polyol molecule; alternatively, an average of 2.5 to 4.5 hydroxyl group per polyol molecule; alternatively, an average of 2.5 to 3.5 hydroxyl group per polyol molecule; alternatively, an average of 3 to 4 hydroxyl group per polyol molecule; alternatively, an average of about 3 hydroxyl groups per polyol molecule; alternatively, an average of about 4 hydroxyl groups per polyol molecule; alternatively, an average of about 5 hydroxyl groups per polyol molecule; or alternatively an average of about 6 hydroxy groups per polyol molecule.

In an embodiment, the polyol that formed the residues of the polyol or mixture of polyols that formed the residues of the polyols may have had a molecular weight or average molecular weight less than 300. In other embodiments, the polyol that formed the residue of the polyol or mixture of polyols that formed the residues of the polyols may have had a molecular weight or average molecular weight less than 250; alternatively less than 200; alternatively, less than 150; or alternatively, less than 100.

In an embodiments, the polyol that formed the residue of the polyol is a diol, triol, a tetraol, pentaol, hexaol, or combination thereof; alternatively a diol, triol, tetraol or combination thereof; or alternatively, a triol, tetraol or combination thereof. In some embodiments, the polyol that formed the residue of the polyol is a diol; alternatively, a triol; alternatively, a tetraol; alternatively, a pentaol; or alternatively, a hexaol. Suitable polyols that may form the residue of the polyol include ethane diol, propanediol, butanediol, pentanediol, hexanediol, cyclohexane diol, phenylethane diol, cyclohexanedimethanol, dimethyolpropane, benzenedimethanol, cyclohexanetriol, trihydroxybenzene, trimethyolethane, trimethylolpropane, trimethylolbutane, glycerol, pentaerythritol, sorbitol, or any combination thereof; alternatively, cyclohexane diol, trimethylol propane, glycerol, pentaerythritol, or combinations thereof; alternatively, glycerol, pentaerythritol, or combinations thereof. In some embodiments, the polyol that may form the residue of the polyol include 1,2-ethanediol, 1,3-propanediol, 1,4-butanediol, 1,5-pentanediol, 1,6-hexanediol, dimethylolpropane, neopentyl glycol, 2-propyl-2-ethyl-1,3-propanediol, 1,2-propanediol, 1,2-butanediol, 1,3-butanediol, 1,4-butanediol, diethylene glycol, triethylene glycol, polyethylene glycol, dipropylene glycol, tripropylene glycol, polypropylene glycol, 1,1-cyclohexanedimethanol, 1,2-cyclohexanedimethanol, 1,3-cyclohexanedimethanol, 1,4-cyclohexanedimethanol, 1,3-dioxane-5,5-dimethanol, 1-phenyl-1,2-ethanediol, trimethylolpropane, trimethylolethane, trimethylolbutane, glycerol, 1,2,5-hexanetriol, pentaerythritol, ditrimethylolpropane, diglycerol, ditrimethylolethane, 1,3,5-trihydroxybenzene, 1,2-benzenedimethanol, 1,3-benzenedimethanol, 1,4-benzenedimethanol, 1-phenyl-1,2-ethanediol, sorbitol, or any combination thereof. In other embodiments, the polyol that may be used as the polyol residue may be trimethylolpropane, glycerol, pentaerythritol, or combinations thereof; alternatively, trimethylolpropane; alternatively, glycerol; alternatively, pentaerythritol; or alternatively sorbitol.

It should be appreciated that not all of the hydroxyl groups of the polyol that form the residue of the polyol of the unsaturated ester molecule having ester linkages must form ester linkages. In some instances some of the hydroxyl groups may not form ester linkages and may remain as hydroxyl group. In an embodiment, greater than 80, 85, 90, 95 percent of all hydroxyl groups of the residue of the polyol form ester linkages. In an embodiment, the unsaturated ester molecules having ester linkages that may comprise a residue of a polyol and carboxylic acid residues having a terminal carbon-carbon double bond are substantially devoid of hydroxy groups derived from the polyol. In other embodiments, substantially all of the hydroxyl groups of the polyol that forms the residue of a polyol form ester linkages with a carboxylic acid residue having a terminal carbon-carbon double bond. In some embodiments, the average ratio of carboxylic acid residues having a terminal carbon-carbon double bond to hydroxyl groups of the polyol of the residue of the polyol is greater than 0.70:1; alternatively, greater than 0.75:1; alternatively, greater than 0.80:1; alternatively, greater than 0.85:1; alternatively, greater than 0.90:1; alternatively, greater than 0.95:1.

It will be appreciated that not all of the ester linkages comprising the residue of the polyol may comprise carboxylic acid residues having a terminal carbon-carbon double bond. For example, some of methods of producing the unsaturated ester having ester linkages comprising a residue of a polyol and a carboxylic acid residues having a terminal carbon-carbon double bond may have ester linkages with saturated carboxylic acid residues. Considering this situation, the unsaturated ester molecules having ester linkages comprising any residue of a polyol described herein and any carboxylic acid residue having a terminal carbon-carbon double bond described herein may have an average of greater than 75, 80, 85, or 90 percent of hydroxyl units of the polyol forming the residue of the polyol residue having an ester linkage with a carboxylic acid having a terminal carbon-carbon double bond.

In an embodiment, the unsaturated ester molecules, whether described as having particular functional groups or as unsaturated ester molecules having ester linkages comprising a residue of a polyol and at least two carboxylic acid residues having a terminal carbon-carbon double bond may have an average ratio of terminal carbon-carbon double bonds to ester groups in the unsaturated ester molecules less than 1.15:1; alternatively, less than 1.1:1; or alternatively, less than 1.05:1. In some embodiments, the thiol ester molecules, whether described as having particular functional groups or as unsaturated ester molecules having ester linkages comprising a residue of a polyol and at least two carboxylic acid residues having a terminal carbon-carbon double bond may have an average ratio of terminal carbon-carbon double bonds to ester groups in the unsaturated ester molecules ranges from 0.75:1 to 1.15:1; alternatively, ranges from 0.85:1 to 1.1:1; or alternatively, ranges from 0.90:1 to 1.05:1. In other embodiments, the thiol ester molecules, whether described as having particular functional groups or as unsaturated ester molecules having ester linkages comprising a residue of a polyol and carboxylic acid residues having a terminal carbon-carbon double bond may have an average ratio of terminal carbon-carbon double bonds to ester groups in the unsaturated ester molecules of about 1:1.

Processes for Producing Unsaturated Ester Molecules Having Terminal Carbon-Carbon Double Bonds The unsaturated esters having terminal carbon-carbon double bonds may be produced via various methods. In an aspect, the unsaturated ester having terminal carbon-carbon double bonds may be produced by metathesis of an unsaturated ester having internal carbon-carbon double bonds with ethylene. In another aspect, the unsaturated esters having terminal carbon-carbon double bonds may be produced by reacting a polyol with a carboxylic acid having a terminal carbon-carbon double bond, a simple ester of a carboxylic acid having a terminal carbon-carbon double bond, or an anhydride of a carboxylic acid having a terminal carbon-carbon double bond. In yet another aspect, the unsaturated esters having terminal carbon-carbon double bonds may be produced via the thermal cracking of unsaturated esters having an internal carbon-carbon double bond and a hydroxy group separated from a carbon atom of the internal carbon-carbon double bond by a methylene group.

The choice of the technique utilized to produce the unsaturated esters having a terminal carbon-carbon double bond may depend on the purity of the source composition, the cost of the process, the identity of the source composition, and the desired purity of the final composition. For example, the metathesis process may provide a higher purity composition, e.g., due to a higher yield, but may have a higher cost of implementation due to catalyst costs and purification costs for the source compound. In contrast, thermal cracking may be easier to implement and function on a wider variety of species. However, the yields associated with thermal cracking may be low, e.g., 50% or less, and, thus, the costs associated with purifying the terminal alkene composition may be higher.

Metathesis of Unsaturated Esters Having Internal Carbon-Carbon Double Bonds

In an aspect, the unsaturated esters having a terminal carbon-carbon double bonds (or the unsaturated esters compositions comprising or consisting essentially of, unsaturated esters having a terminal carbon-carbon double bonds) may be produced by a) contacting ethylene and unsaturated ester molecules having internal carbon-carbon double bonds (or an unsaturated ester composition comprising, or consisting essentially of, unsaturated ester molecules having internal carbon-carbon double bonds) with a metathesis catalyst composition and b) forming unsaturated ester molecules having terminal carbon-carbon double bonds (or composition comprising, or consisting essentially of, unsaturated ester molecules having terminal carbon-carbon double bonds). Generally, the unsaturated ester molecules having terminal carbon-carbon double bonds (or composition comprising, or consisting essentially of, unsaturated ester molecules having terminal carbon-carbon double bonds) are formed at conditions capable of forming the unsaturated ester molecules having terminal carbon-carbon double bonds (or the unsaturated ester composition comprising, or consisting essentially of, unsaturated ester molecules having terminal carbon-carbon double bonds). Generally, any unsaturated ester composition comprising unsaturated ester molecules having internal carbon-carbon double bonds described herein may be utilized. In some embodiments, the unsaturated ester composition comprising unsaturated ester molecules having an internal carbon-carbon double bond may be any unsaturated natural source oil described herein. Furthermore, the method may be utilized to produce any unsaturated ester composition comprising, or consisting essentially of, unsaturated ester molecules having a terminal carbon-carbon double bond described herein. The metathesis process for producing the unsaturated ester composition comprising, or consisting essentially of, unsaturated ester molecules having terminal carbon-carbon double bonds can also include any additional process steps or process conditions described herein.

Metathesis Scheme 1 provides a general metathesis reaction for one particular unsaturated ester having internal carbon-carbon bonds found within some unsaturated ester compositions (e.g. a natural source oil such as soybean oil). One having ordinary skill in the art will recognize Metathesis Scheme 1 is not limiting. The unsaturated ester compositions comprising, or consisting essentially of, unsaturated ester molecules having internal carbon-carbon double bonds described herein may contain additional unsaturated ester having internal carbon-carbon double bonds or may contain totally different unsaturated esters having internal carbon-carbon double bonds than is shown in Metathesis Reaction Scheme 1. Metathesis Scheme 1 is merely a sample, non-limiting, representation of the metathesis reaction between ethylene and an unsaturated ester molecule having internal carbon-carbon double bonds. Additionally, one having ordinary skill in the art will appreciated that Metathesis Scheme 1 only provides some of the expected by-product that would be produced by the metathesis reaction between ethylene and an unsaturated ester molecule having internal carbon-carbon double bonds. Depending upon the actual composition of the unsaturated ester compositions comprising, or consisting essentially of, unsaturated ester molecules having internal carbon-carbon double bonds and the metathesis reaction conditions, other products, by-products, and impurities may be produced.

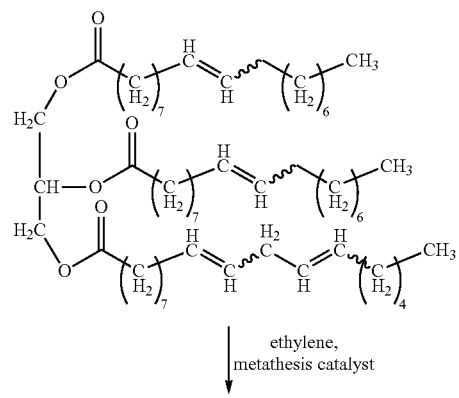

Metathesis Scheme 1 ethylene, metathesis catalyst

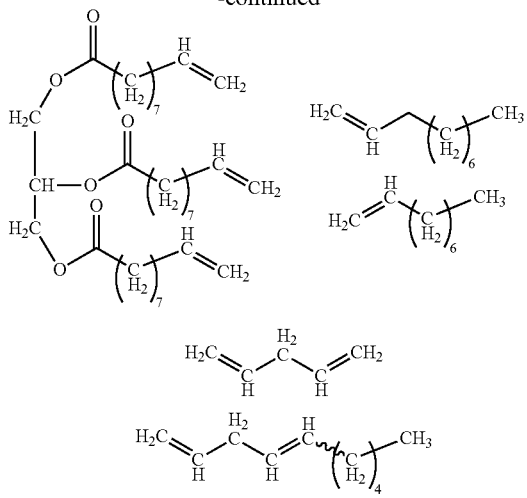

Generally, any metathesis catalyst that is capable of producing unsaturated ester molecules having a terminal carbon-carbon double bond from an unsaturated ester composition comprising, or consisting essentially of, unsaturated esters having an internal carbon-carbon double bond may be used. However, depending upon other metathesis reaction parameters (e.g. unsaturated ester composition characteristics and/or the metathesis reaction conditions), particular class(es) of metathesis catalyst(s) may be selected in particular instances.

Metathesis catalysts and/or metathesis catalyst systems can be classified by the compound(s) of the metathesis catalyst contacted with the unsaturated ester composition comprising, or consisting essentially of, unsaturated esters having an internal carbon-carbon double bond. Often the true catalytic species may be difficult to determine because the initial catalytic specie is transformed to other species once the metathesis reaction is initiated. One of ordinary skill in the art will readily recognize the type of metathesis catalyst or metathesis catalyst system based upon the compound(s) contacted with the unsaturated ester composition comprising, or consisting essentially of, unsaturated esters having an internal carbon-carbon double bond. In some instances, a precursor of the metathesis catalyst or metathesis catalyst system may be contacted with the unsaturated ester composition comprising, or consisting essentially of, unsaturated esters having an internal carbon-carbon double bond to create the metathesis catalyst or metathesis catalyst system in situ. One of skill in the art will readily recognize the particular type of metathesis catalyst and/or metathesis catalyst system from the materials added/contacted with the unsaturated ester composition comprising, or consisting essentially of, unsaturated esters having an internal carbon-carbon double bond.

In an embodiment, the metathesis catalyst can be a metal oxide based metathesis catalyst system, a metal halide based metathesis catalyst system, or a metal carbene based metathesis catalyst system. In some embodiments, the metathesis catalyst can be a metal oxide based metathesis catalyst system or a metal halide based metathesis catalyst system. In other embodiments, the metathesis catalyst may be a metal oxide based metathesis catalyst system; alternatively, a metal halide based metathesis catalyst system; or alternatively, a metal carbene based metathesis catalyst system.

For example, the metal oxide based metathesis catalysts or catalyst systems (hereafter referred to as "metal oxide metathesis catalyst(s)") may include cobalt oxide, molybdenum oxide, tungsten oxide, rhenium oxide, or combinations thereof. In various embodiments, the metal oxide metathesis catalyst may include a support, or, alternatively, the metal oxide metathesis catalyst may be unsupported. Supports that may be useful include alumina, silica, silica-alumina, and aluminum-phosphate. In embodiments, the metal oxide metathesis catalyst may include a metal alkyl activator, as described herein. Non-limiting examples of metal oxide metathesis catalysts that may be used in embodiments include molybdenum oxide on alumina ($MoO_3/Al_2O_3$), tungsten oxide on silica ($WO_3/SiO_2$), rhenium oxide on alumina ($Re_2O_7/Al_2O_3$), cobalt oxide and molybdenum oxide on alumina ($CoO/MoO_3/Al_2O_3$), and rhenium oxide on alumina activated with tetramethyl tin ($Re_2O_7/Al_2O_3/SnMe_4$). Other suitable metal oxide metathesis catalysts are known to those skilled in the art.

Metal halide based metathesis catalysts and/or catalyst systems (hereafter referred to as "metal halide metathesis catalyst(s)") may include a halide of tungsten, molybdenum, or a mixture thereof. In various embodiments, the halide of the metal halide metathesis catalyst may be chloride, bromide, or iodide. In one embodiment, the halide is chloride. In another embodiment, the halide is bromide. In another embodiment, the halide is iodide. In various embodiments, the metal halide metathesis catalyst may include tungsten chloride, molybdenum chloride, or mixtures thereof. In one embodiment, the metal halide metathesis catalyst includes tungsten chloride. In another embodiment, the metal halide metathesis catalyst includes molybdenum chloride. Typically, the metal halide metathesis catalyst may include a metal alkyl activator, as described herein. The metal halide metathesis catalyst may include other agents in addition to the metal halide and metal alkyl activator, for example, alcohol or oxygen, to provide and/or increase metathesis activity. Non-limiting examples of metal halide metathesis catalysts include tungsten chloride/tetrabutyl tin ($WCl_6/SnMe_4$), tungsten chloride/ethylaluminum dichloride ($WCl_6/EtAlCl_2$), tungsten chloride/ethylaluminum dichloride/ethyl alcohol ($WCl_6/EtAlCl_2/EtOH$), molybdenum chloride/triethyl aluminum ($MoCl_5/AlEt_3$), and molybdenum chloride/triethyl aluminum/$O_2$ ($MoCl_5/AlEt_3/O_2$). Other suitable metal halide metathesis catalysts are known to those skilled in the art.

Typically, the metal alkyl activator for the metal oxide metathesis catalysts or the metal halide metathesis catalysts may include, or consist essentially of, any metal alkyl. Suitable metal alkyl compounds may include alkyl lithium, alkyl magnesium, alkyl aluminum, alkyl tin compounds, and mixtures thereof. In an embodiment, the metal alkyl compound may be an alkyl lithium compound. In another embodiment, the metal alkyl compound may be an alkyl magnesium compound. In another embodiment the metal alkyl compound may be an alkyl aluminum compound. In yet another embodiment, the metal alkyl compound may be an alkyl tin compound. Non-limiting examples of alkyl aluminum compounds, which may be used as the metal alkyl activator, may include trialkyl aluminum compounds and/or alkyl aluminum halide compounds. The alkyl groups on the metal alkyl may include any $C_1$ to $C_{10}$ hydrocarbyl group; or alternatively, a $C_1$ to a $C_5$ hydrocarbyl group. In various embodiments, the alkyl group for the metal alkyl can be a methyl group, ethyl group, n-propyl group, iso-propyl group, n-butyl group, sec-butyl group, or tert-butyl group; alternatively, a methyl group, ethyl group, n-butyl group, sec-butyl group, or tert-butyl group; alternatively, a methyl group; alternatively, an ethyl group; alternatively, an n-butyl group; alternatively, a sec-butyl group; or alternatively, a tert-butyl group. The choice of the alkyl group may depend on the activity desired. Examples of suitable trialkyl aluminum compound include trimethyl aluminum, triethyl aluminum, and tributyl aluminum. The halide of the alkyl aluminum halide compounds can be can be chloride, bromide, or iodide alternatively, bromide; or alternatively, iodide. Examples of suitable alkyl aluminum halides include ethyl aluminum dichloride, diethylaluminum chloride, and ethylaluminum sesquichloride. Suitable alkyl tin compounds include tetramethyl tin, tetraethyl tin, and tetrabutyl tin.

Metal carbene metathesis catalysts and/or catalyst systems (hereafter referred to as "metal carbene metathesis catalyst(s)") may be characterized by the presence of a metal-carbon double bond. As opposed to the metal oxide and the metal halide metathesis catalysts, the metal carbene metathesis catalysts are compounds which have a stable metal-carbon double bond or can form a metal-carbon double bond in situ from a metal precursor having a stable metal-carbon single bond.

The metal of suitable metal carbene metathesis catalysts may include, or consist essentially of, tungsten, tantalum, osmium, molybdenum, or ruthenium. In an embodiment, the metal carbene metathesis catalyst may be a tungsten carbene metathesis catalyst, a molybdenum carbene metathesis catalyst, or a ruthenium carbene metathesis catalyst, or a combination thereof. In some embodiments, the metal carbene metathesis catalyst may be a ruthenium carbene metathesis catalysts or molybdenum carbene metathesis catalyst. In an embodiment, the metal carbene metathesis catalyst may be a ruthenium carbene metathesis catalysts. In another embodiment, the metal carbene metathesis catalyst may be a molybdenum carbene metathesis catalyst. In some embodiments, the metal carbene metathesis catalyst may be a tungsten carbene metathesis catalyst. In another embodiment, the metal carbene metathesis catalyst may be an osmium carbene metathesis catalyst. In another embodiment, the metal carbene metathesis catalyst may be a ruthenium carbene metathesis catalyst. In another embodiment, the metal carbene metathesis catalyst may be a molybdenum carbene metathesis catalyst.

In an embodiment, the ruthenium carbene metathesis catalyst may have the structure $L^1L^2X_2Ru=CHR$ wherein $L^1$ and $L^2$ may be an organic ligand, X is a halide, and R represents hydrogen or a hydrocarbyl group. Further embodiments of the groups $L^1$, $L^2$, X, and R are independently described herein. Generally, the ruthenium carbene metathesis catalyst having the structure $L^1L^2X_2Ru=CHR$ can be described using any combination of $L^1$, $L^2$, X, or R, as described herein.

In an embodiment, $L^1$ and $L^2$ of the ruthenium carbene metathesis catalyst having the structure $L^1L^2X_2Ru=CHR$ can independently be $R'_3P$, an imidazolinylidene group, or an imidazolidinylidene group. In some embodiments, $L^1$ and $L^2$ are $R'_3P$; alternatively, $L^1$ is $R'_3P$ and $L^2$ is an imidazolinylidene group or an imidazolidinylidene group; alternatively, $L^1$ is $R'_3P$ and $L^2$ is an imidazolinylidene group; alternatively, $L^1$ is $R'_3P$ and $L^2$ is an imidazolidinylidene group; alternatively, $L^1$ and $L^2$ are imidazolinylidene groups; or alternatively, $L^1$ and $L^2$ are imidazolidinylidene groups.

In an embodiment, R' of $R'_3P$ can be a hydrocarbyl group. In some embodiments, each R' of $R'_3P$ can be the same; alternatively, each R' of $R'_3P$ can be different; or alternatively, one R' of $R'_3P$ can be different from the other two R's. In some embodiments, each R' of $R'_3P$ can be a $C_1$ to $C_{15}$ hydrocarbyl group; or alternatively, a $C_1$ to $C_{10}$ hydrocarbyl group. In other embodiments, each hydrocarbyl R' of $R'_3P$ can independently be an alkyl group or an aromatic group; alternatively, an alkyl group; or alternatively, an aromatic group. In an embodiment each alkyl R' of $R'_3P$ can independently be a methyl group, ethyl group, n-propyl group, isopropyl group, tert-butyl group, neo-pentyl group, cyclopentyl group, or cyclohexyl group. In some embodiments, one or more R's of $R'_3P$ can be a phenyl group; or alternatively a substituted phenyl group. In an embodiment, the substituents of the substituted phenyl group(s) within $R'_3P$ can be a $C_1$-$C_5$ organyl group(s); or alternatively, $C_1$-$C_5$ hydrocarbyl group(s). In some embodiments, $R'_3P$ can be a trialkyl phosphine or triphenyl phosphine; alternatively, trialkyl phosphine; or alternatively, triphenyl phosphine. In an embodiment, $R'_3P$ can be trimethyl phosphine, triethyl phosphine, triisopropyl phosphine, tri-tert-butyl phosphine, tri-neopentyl phosphine, tricyclopentyl phosphine, tricyclohexyl phosphine, or triphenyl phosphine; alternatively, triisopropyl phosphine, tri-tert-butyl phosphine, tri-neopentyl phosphine, tricyclopentyl phosphine, tricyclohexyl phosphine, or triphenyl phosphine; alternatively, tricyclopentyl phosphine, tricyclohexyl phosphine, or triphenyl phosphine; alternatively, tricyclopentyl phosphine or tricyclohexyl phosphine; alternatively, tricyclopentyl phosphine; alternatively, tricyclohexyl phosphine; or alternatively triphenyl phosphine.

In an embodiment, the imidazolinylidene group or imidazolidinylidene group can be a $C_3$ to $C_{80}$ imidazolinylidene group or imidazolidinylidene group; alternatively, a $C_3$ to $C_{50}$ imidazolinylidene group or imidazolidinylidene group; alternatively, a $C_5$ to $C_{40}$ imidazolinylidene group or imidazolidinylidene group. In some embodiments, the imidazolinylidene group may be a 1,3-disubstituted imidazolinylidene group. In some embodiments, the imidazolidinylidene group may be a 1,3-disubstituted imidazolidinylidene group. In an embodiment, each 1,3-substitutents of the 1,3-disubstituted imidazolinylidene group or 1,3-disubstituted imidazolidinylidene group can be a hydrocarbyl group. In an embodiment, the 1,3-substitutents of the 1,3-disubstituted imidazolinylidene group or 1,3-disubstituted imidazolidinylidene group can be a $C_1$ to $C_{30}$ hydrocarbyl group. In some embodiments, each 1,3-substitutent of the 1,3-disubstituted imidazolinylidene group or 1,3-disubstituted imidazolidinylidene group can independently be a $C_6$ to $C_{20}$ aromatic group or a $C_1$ to $C_{10}$ alkyl groups. In other embodiments, the 1,3-substitutents of the 1,3-disubstituted imidazolinylidene group or 1,3-disubstituted imidazolidinylidene group can be $C_6$ to $C_{20}$ aromatic groups; or alternatively, $C_1$ to $C_{10}$ alkyl groups. In an embodiment, the aromatic group(s) of the 1,3-disubstituted imidazolinylidene group or 1,3-disubstituted imidazolidinylidene group can be a substituted aromatic group. In some embodiments, the substituted aromatic group of the 1,3-disubstituted imidazolinylidene group or 1,3-disubstituted imidazolidinylidene group can be a 2-disubstituted phenyl group, a 2,6-disubstituted phenyl group, or, a 2,4,6-trisubstituted phenyl group; alternatively, a 2,6-disubstituted phenyl group; or alternatively, a 2,4,6-trisubstituted phenyl group. Suitable substituents for the substituted phenyl group(s) within the 1,3-disubstituted imidazolinylidene group or 1,3-disubstituted imidazolidinylidene group include any $C_1$ to $C_{10}$ hydrocarbyl group; or alternatively, any $C_1$ to $C_5$ hydrocarbyl group. In some embodiments, each hydrocarbyl group(s) of the substituted phenyl group(s) within the 1,3-disubstituted imidazolinylidene group or 1,3-disubstituted imidazolidinylidene group can independently be a methyl group, ethyl group, n-propyl group, iso-propyl group, n-butyl group, sec-butyl group, or tert-butyl group; alternatively, a methyl group, ethyl group, n-butyl group, sec-butyl group, or tert-butyl group; alternatively, a methyl group; alternatively, an ethyl group, alternatively, an isopropyl group; or alternatively, a tert-butyl group. In some embodiments, the 1,3-substitutents of the 1,3-disubstituted imidazolinylidene group or 1,3-disubstituted imidazolidinylidene group can be a 2,6-diisopropylphenyl group or a 2,4,6-trimethylphenyl group; alternatively, a 2,6-diisopropylphenyl group; or alternatively, a 2,4,6-trimethylphenyl group.

In various embodiments, each X of the ruthenium carbene metathesis catalyst having the structure $L^1L^2X_2Ru=CHR$ can independently be chloride, bromide, or iodide. In an embodiment, X can be chloride. In another embodiment, X can be bromide. In another embodiment, X can be iodide.

In an embodiment, R of the ruthenium carbene metathesis catalyst having the structure $L^1L^2X_2Ru=CHR$ can be hydrogen or a $C_1$ to $C_{20}$ hydrocarbyl group. In some embodiments, hydrocarbyl group R can be a methyl group ($—CH_3$), an ethyl group ($—CH_2CH_3$), an isopropyl group ($—CH(CH_3)_2$), a tert-butyl group ($—C(CH_3)_3$), a phenyl group ($—C_6H_5$), a 2-methyl-2-propene group ($—CH=C(CH_3)_2$), or a 2,2-diphenylethene group ($—CH=C(C_6H_5)_2$). In other embodiments, R can be a tert-butyl group ($—C(CH_3)_3$, a phenyl group ($—C_6H_5$), a 2-methyl-2-propene group ($—CH=C(CH_3)_2$), or a 2,2-diphenylethene group ($—CH=C(C_6H_5)_2$); alternatively, hydrogen; alternatively, a tert-butyl group ($—C(CH_3)_3$); alternatively, a phenyl group ($—C_6H_5$); alternatively, a tert-butyl group ($—C(CH_3)_3$); alternatively, a phenyl group ($—C_6H_5$); alternatively, a 2-methyl-2-propene group ($—CH=C(CH_3)_2$); or alternatively, a 2,2-diphenylethene group ($—CH=C(C_6H_5)_2$).

In some non-limiting embodiments, the ruthenium carbene metathesis catalyst can be di-chloro(phenylmethylene) bis(tricyclohexyl phosphine) ruthenium, dichloro(3-methyl-2-butenylidene) bis(tricyclohexyl phosphine) ruthenium, dichloro(3-methyl-2-butenylidene) bis(tricyclopentyl phosphine) ruthenium, 1,3-bis-(2,4,6-trimethylphenyl)-2-(imidazolidinylidene)(phenylmethylene)dichloro(tricyclo-hexyl phosphine) ruthenium, or 1,3-bis-(2,6-diisopropylphenyl)-2-(imidazolidinylidene)(phenylmethyl-ene)dichloro(tricyclohexyl phosphine) ruthenium. In some embodiments, the ruthenium metal carbene metathesis catalyst can be dichloro(phenylmethylene) bis(tricyclohexyl phosphine) ruthenium; alternatively, dichloro(3-methyl-2-butenylidene) bis(tricyclohexyl phosphine) ruthenium; alternatively, 1,3-bis-(2,4,6-trimethylphenyl)-2-(imidazolidinylidene)(phenylmethylene)dichloro(tricyclohexyl phosphine) ruthenium; or alternatively, 1,3-bis-(2,6-diisopropylphenyl)-2-(imidazolidinylidene)(phenyl-methylene)dichloro(tricyclohexyl phosphine) ruthenium.

In an embodiment, the molybdenum carbene metathesis catalyst can have the structure $Mo(=CHR)(NAr)(OR')_2$ wherein R is a hydrogen or hydrocarbyl group, Ar is a substituted aromatic ring, and R' is a hydrocarbyl group or a halogenated hydrocarbyl group. Further embodiments of the groups R, Ar and R' are independently described herein. Generally, the molybdenum carbene metathesis catalyst having the structure $Mo(=CHR)(NAr)(OR')_2$ can be described using any combination of R described herein, Ar described herein, and R' described herein.

In some embodiments, R of the molybdenum carbene metathesis catalyst having the structure $Mo(=CHR)(NAr)(OR')_2$ can be hydrogen or a $C_1$ to $C_{20}$ hydrocarbyl group; or alternatively, a $C_1$ to $C_{20}$ hydrocarbyl group. In some embodiments, the hydrocarbyl group R can be a methyl group ($—CH_3$), an ethyl group ($—CH_2CH_3$), an isopropyl group ($—CH(CH_3)_2$), a tert-butyl group ($—C(CH_3)_3$), a phenyl group ($—C_6H_5$), a 2-methyl-2-propene group ($—CH=C(CH_3)_2$), or a 2,2-diphenylethene group ($—CH=C(C_6H_5)_2$). In other embodiments R can be a tert-butyl group ($—C(CH_3)_3$), a phenyl group ($—C_6H_5$), a 2-methyl-2-propene group ($—CH=C(CH_3)_2$), or a 2,2-diphenylethene group ($—CH=C(C_6H_5)_2$); alternatively, a tert-butyl group ($—C(CH_3)_3$) or a phenyl group ($—C_6H_5$); alternatively, hydrogen; alternatively, a tent-butyl group ($—C(CH_3)_3$); alternatively, a phenyl group ($—C_6H_5$); alternatively, a 2-methyl-2-propene group ($—CH=C(CH_3)_2$); or alternatively, a 2,2-diphenylethene group ($—H=C(C_6H_5)_2$).

In an embodiment, the substituted aromatic ring, Ar, of the molybdenum carbene metathesis catalyst having the structure $Mo(=CHR)(NAr)(OR')_2$ can be a $C_6$ to $C_{30}$ aromatic group; alternatively, a $C_6$ to $C_{20}$ aromatic group. In some embodiments, the substituted aromatic ring, Ar, is a $C_6$ to $C_{20}$ hydrocarbyl group. In an embodiment, each substituent of the substituted aromatic ring, Ar, of the molybdenum carbene metathesis catalyst having the structure $Mo(=CHR)(NAr)(OR')_2$ can independently be a $C_1$ to $C_{10}$ hydrocarbyl group; or alternatively, a $C_1$ to $C_5$ hydrocarbyl group. In some embodiments, the substituted aromatic ring, Ar, of the molybdenum carbene metathesis catalyst having the structure $Mo(=CHR)(NAr)(OR')_2$ can be a 2-substituted phenyl group, a 2,6-disubstituted phenyl group, or alternatively, a 2,4,6-trisubstituted phenyl group. In an embodiment, each substituent of the substituted aromatic ring can independently be a methyl group ($—CH_3$), an ethyl group ($—CH_2CH_3$), an isopropyl group ($—CH(CH_3)_2$), a tert-butyl group ($—C(CH_3)_3$), or a neopentyl group ($—CH_2C(CH_3)_3$); alternatively, a methyl group ($—CH_3$), an isopropyl group ($—CH(CH_3)_2$), or a tert-butyl group ($—C(CH_3)_3$); alternatively a methyl group ($—CH_3$) or an isopropyl group ($—CH(CH_3)_2$). In some embodiments, each substituent of the substituted aromatic ring can independently be a methyl group ($—CH_3$); alternatively, an isopropyl group ($—CH(CH_3)_2$); or alternatively, a tert-butyl group ($—C(CH_3)_3$). In some non-limiting embodiments, the substituted aromatic ring, Ar, of the molybdenum carbene metathesis catalyst having the structure $Mo(=CHR)(NAr)(OR')_2$ can be a 2-tert-butylphenyl group, a 2,6-dimethylphenyl group, a 2,6-diisopropylphenyl group, or a 2,4,6-trimethyl phenyl group; alternatively, a 2-tert-butylphenyl group; alternatively, a 2,6-dimethylphenyl group; alternatively, a 2,6-diisopropylphenyl group; or alternatively, a 2,4,6-trimethyl phenyl group.

In an embodiment, each R' of the molybdenum carbene metathesis catalyst having the structure $Mo(=CHR)(NAr)(OR')_2$ can independently be a $C_1$ to $C_{10}$ organic group; or alternatively a $C_1$ to $C_5$ organic group. In some embodiments, the $C_1$ to $C_{10}$ or $C_1$ to $C_5$ organic group can be a hydrocarbylhalyl group (a group consisting of hydrogen, carbon, and halogen atoms); alternatively, a hydrocarbylfluoryl group (a group consisting of hydrogen, carbon, and fluorine atoms); or alternatively, a hydrocarbyl group. In an embodiment, the halogen atoms of the hydrocarbylhalyl group can be fluorine, chlorine, bromine, iodine or combinations thereof; alternatively fluorine; alternatively, chlorine; alternatively, bromine; or alternatively, iodine. In some embodiments, each R' of the molybdenum carbene metathesis catalyst having the structure $Mo(=CHR)(NAr)(OR')_2$ can independently be tert-butyl group ($—C(CH_3)_3$), or a hexafluoro-tert-butyl group ($—C(CF_3)_2(CH_3)$) group. In other embodiments, $(OR')_2$ can represent a single organic group wherein the two R' groups attached to the oxygen atoms are connected via a bond between any divalent, trivalent, or tetravalent atom with in the R' groups. In further embodiments, $(OR')_2$ can represent a single organic group wherein the two R' groups attached to the oxygen atoms are connected via a carbon-carbon bond between any carbon atom of the two R' groups.

In an embodiment, the molybdenum carbene metathesis catalyst can be $Mo(=CH—C(CH_3)_3)(N-2,6-diisopropylphenyl)(OC(CH_3)_3)$, $Mo(=CH—C(CH_3)_2(C_6H_5))(N-2,6-diisopropyl-phenyl)(OC(CH_3)_3)$, $Mo(=CH—C(CH_3)_3)(N-

2,6-diisopropylphenyl)(OC(CH$_3$)(CF$_3$)$_2$), or Mo(=CH—C(CH$_3$)$_2$(C$_6$H$_5$))(N-2,6-diisopropylphenyl)(OC(CH$_3$)(CF$_3$)$_2$). In other embodiments, the molybdenum metathesis catalyst can be Mo(=CH—C(CH$_3$)$_3$)(N-2,6-diisopropylphenyl)(OC(CH$_3$)$_3$); alternatively, Mo(=CH—C(CH$_3$)$_2$(C$_6$H$_5$))(N-2,6-diisopropylphenyl)(OC(CH$_3$)$_3$); alternatively, Mo(=CH—C(CH$_3$)$_3$)(N-2,6-diisopropylphenyl)(OC(CH$_3$)(CF$_3$)$_2$); or alternatively, Mo(=CH—C(CH$_3$)$_2$(C$_6$H$_5$))(N-2,6-diisopropyl-phenyl)(OC(CH$_3$)(CF$_3$)$_2$).

In some embodiments, the metal carbene metathesis catalyst can be tethered to a support. The metal carbene metathesis catalyst can be tethered to the support via any of the ligands which do not contain the metal-carbon double bond. In an embodiment the metal carbene catalyst support may be a polymer.

Minimally, the metathesis catalyst composition comprises the metathesis catalyst (and/or the metathesis catalyst system components). In an embodiment, the metathesis catalyst composition may consist essentially of the metathesis catalyst (or the metathesis catalyst system components). In an embodiment, the metathesis catalyst composition comprising the metathesis catalyst can further comprise a solvent or diluent. In some embodiments, the metathesis catalyst composition comprising the metathesis catalyst consists essentially of the metathesis catalyst (or the metathesis catalyst system components); or alternatively, consists essentially of the metathesis catalyst (or the metathesis catalyst system components) and a solvent or diluent. Solvents or diluents which may be utilized in the catalyst composition comprising the metathesis catalyst are described herein. In other embodiments, the metathesis catalyst composition comprising the metathesis catalyst (or the metathesis catalyst system components) is substantially devoid of solvent or diluent.

In an embodiment, the unsaturated ester composition comprising, or consisting essentially of, unsaturated ester molecules having internal carbon-carbon double bonds may be purified before being subjected to the metathesis reaction to form unsaturated esters having terminal carbon-carbon double bonds. Purification may help extend the life of the metathesis catalyst system and/or increase the number of turnovers by removing catalyst poisons that may be present in a unsaturated ester composition comprising, or consisting essentially of, unsaturated ester molecules having internal carbon-carbon double bond. These poisons include water, alcohols, oxygen, organic hydroperoxides, organic peroxides, ketones, and aldehydes, among other compounds. Some of the poisons, e.g. organic peroxides may be generated by the contact of the unsaturated ester composition with oxygen in air. Many of the metathesis catalysts may be less sensitive to these materials, e.g., less prone to deactivation when placed in contact with these groups. Accordingly, the purification performed by a supplier of a material used as a source composition may be sufficient. However, even in these cases, purification may provide a longer better process economics.

Purification may be performed by any number of techniques. For example, in an embodiment, purification may start with purging the unsaturated ester composition comprising, or consisting essentially of, unsaturated ester molecules having internal carbon-carbon double bonds with an inert gas which may remove oxygen and part of the water. Water may be removed by contacting the unsaturated ester composition comprising, or consisting essentially of, unsaturated ester molecules having internal carbon-carbon double bonds with an adsorbent. Similar, impurities which have polar groups may be removed by contacting the unsaturated ester composition comprising, or consisting essentially of, unsaturated ester molecules having internal carbon-carbon double bonds with an adsorbent. Adsorbents which may be used in the present techniques include, for example, aluminas, silicas, activated carbons, clays, magnesias, aluminosilicates, molecular sieves, titanosilicates, and combinations thereof. The unsaturated ester composition comprising, or consisting essentially of, unsaturated ester molecules having internal carbon-carbon double bonds with an adsorbent may be flowed over the adsorbent, e.g., in a drying bed, or may be mixed with the adsorbent and filtered. Once the adsorbent has been removed from the source composition, the source composition may be stored under an inert gas to prevent further poisons from developing. One of ordinary skill in the art will recognize that any number of other suitable techniques may be used for purification of the unsaturated ester composition comprising, or consisting essentially of, unsaturated ester molecules having internal carbon-carbon double bonds with an adsorbent.

The metathesis reaction conditions may include various factors, for example, the molar ratio of carbon-carbon double bonds to metathesis catalyst moieties, the temperature of the metathesis reaction, the ethylene partial pressure in the metathesis reaction, the duration of the metathesis reaction, and the presence or absence of a solvent. The factors are described independently herein and may be utilized in any combination to further describe the process to produce unsaturated ester compositions comprising unsaturated ester composition comprising, or consisting essentially of, unsaturated esters having an internal carbon-carbon double bond via metathesis.

The amount of metathesis catalyst utilized for the metathesis reaction between ethylene and the unsaturated ester composition comprising, or consisting essentially of, unsaturated esters having an internal carbon-carbon double bond may be expressed as a molar ratio of carbon-carbon double bonds in the unsaturated ester composition comprising, or consisting essentially of, unsaturated esters having internal carbon-carbon double bonds. In an embodiment, the molar ratio of the metathesis catalyst to the carbon-carbon double bonds may be less than 1:10, less than 1:50, or less than 1:100. Further, the molar ratio of carbon-carbon double bonds to metathesis catalyst may be greater than 500,000:1; alternatively, greater than 1,000,000:1; or alternatively, greater than 10,000,000:1.

Generally, a molar excess of ethylene, in relation to the number of moles of internal carbon-carbon bonds in the unsaturated ester composition comprising, or consisting essentially of, unsaturated esters having an internal carbon-carbon double bond, may be needed to have high conversion of the internal carbon-carbon double bonds to terminal carbon-carbon double bonds. The molar excess of ethylene may be ensured by maintaining a high partial pressure of ethylene in the reactor. In an embodiment, the partial pressure of ethylene may be greater than 10 psig; alternatively, greater than 50 psig; alternatively, greater than 100 psig; or alternatively greater than 150 psig. In some embodiments, the partial pressure of ethylene may range from 10 psig to 4000 psig; alternatively, range from 50 psig to 3000 psig; alternatively, range from 100 psig to 2000 psig; or alternatively, range from 150 psig to 1000 psig.

The temperature of metathesis reaction between ethylene and the unsaturated ester composition comprising, or consisting essentially of, unsaturated esters having an internal carbon-carbon double bond may influence by the desired conversion, the desired reaction time, and the amount of impurities and/or by products that can be tolerated, among other factors. In an embodiment, the temperature of the metathesis reaction between ethylene and the unsaturated ester composition comprising, or consisting essentially of, unsaturated esters having an internal carbon-carbon double bond may range from 0° C. to 120° C. In other embodiments, the temperature of the metathesis reaction between ethylene and the unsaturated ester composition comprising, or consisting essentially of, unsaturated esters having an internal carbon-carbon double bond may range from 5° C. to 100° C.; alternatively, range from 10° C. to 80° C.; alternatively, range from 15° C. to 70° C.; or alternatively, range from 20° C. to 60° C.

The time for the metathesis reaction between ethylene and the unsaturated ester composition comprising, or consisting essentially of, unsaturated esters having an internal carbon-carbon double bond may influence by the desired conversion, the reaction temperature, and the amount of impurities and/or by products that can be tolerated, among other factors. In an embodiment, the temperature of the metathesis reaction between ethylene and the unsaturated ester composition comprising, or consisting essentially of, unsaturated esters having an internal carbon-carbon double bond may range from 10 minutes to 48 hours. In other embodiments, the temperature of the metathesis reaction between ethylene and the unsaturated ester composition comprising, or consisting essentially of, unsaturated esters having an internal carbon-carbon double bond may range from 20 minutes to 36 hours; alternatively, 30 minutes to 24 hours; or alternatively, 40 minutes to 12 hours.

The metathesis reaction between ethylene and the unsaturated ester composition comprising, or consisting essentially of, unsaturated esters having an internal carbon-carbon double bond may be performed in a batch reactor or a continuous reactor. Non-limiting examples of continuous reactors may be utilized include continuous stirred tank reactors, continuous flow fixed bed reactors, slurry reactors, fluidized bed reactors, continuous plug flow reactors, and catalytic distillation reactors, among others. Non-limiting examples of batch reactors that may be utilized include autoclave reactors. Other types of batch and continuous reactors that can be used in embodiments of the present invention will be apparent to those of skill in the art and are to be considered within the scope of the present invention.

In some aspects, the metathesis reaction metathesis reaction between ethylene and the unsaturated ester composition comprising, or consisting essentially of, unsaturated esters having an internal carbon-carbon double bond may occur in the presence of a solvent. In other aspects, the reaction between the metathesis reaction metathesis reaction between ethylene and the unsaturated ester composition comprising, or consisting essentially of, unsaturated esters having an internal carbon-carbon double bond occurs in the substantial absence of a solvent. When the solvent is present, the solvent may be selected from aromatic hydrocarbons, aliphatic hydrocarbons, organic ethers, organic carbonates, organic esters, halogenated aliphatic hydrocarbons, aromatic hydrocarbons, halogenated aromatic hydrocarbons, and combinations thereof. Aliphatic hydrocarbons, which may be useful as a solvent, include $C_4$ to $C_{20}$ hydrocarbons, or alternatively, $C_5$ to $C_{10}$ hydrocarbons, and may be cyclic or acyclic and include linear or branched isomers, unless otherwise specified. Non-limiting examples of suitable acyclic aliphatic solvents include pentane, hexane, heptane, octane, and combinations thereof. Non-limiting examples of suitable cyclic aliphatic solvents include cyclohexane, methyl cyclohexane, and combinations thereof. Aromatic hydrocarbons, which may be useful as a solvent, include $C_6$ to $C_{20}$ aromatic hydrocarbons; or alternatively, $C_6$ to $C_{10}$ aromatic hydrocarbons. Non-limiting examples of suitable aromatic hydrocarbons include benzene, toluene, xylene (including ortho-xylene, meta-xylene, para-xylene, or mixtures thereof), and ethylbenzene, or combinations thereof. Organic ethers or organic carbonates, which may be useful as a solvent, include $C_2$ to $C_{20}$, organic ethers or organic carbonates; alternatively, $C_2$ to $C_{10}$ organic ethers or organic carbonates; or alternatively, $C_2$ to $C_5$ organic ethers or organic carbonates. Suitable ether solvents may be cyclic or acyclic. Non-limiting examples of suitable ethers which may be useful as a solvent include dimethyl ether, diethyl ether, methyl ethyl ether, monoethers or diethers of glycols (e.g., dimethyl glycol ether), furans, substituted furans, dihydrofuran, substituted dihydrofurans, tetrahydrofuran (THF), substituted tetrahydrofurans, tetrahydropyrans, substituted tetrahydropyrans, 1,3-dioxanes, substituted 1,3-dioxanes, 1,4-dioxanes, substituted 1,4-dioxanes, or mixtures thereof. In an embodiment, each substituent of a substituted furan, substituted dihydrofuran, substituted tetrahydrofuran, substituted tetrahydropyran, substituted 1,3-dioxane, or substituted 1,4-dioxane, can be a $C_1$ to $C_5$ alkyl group. Non-limiting examples of suitable organic carbonates, which may be utilized as a solvent, include ethylene carbonate, propylene carbonate, diethyl carbonate, diethyl carbonate, and combinations thereof. Halogenated aliphatic hydrocarbons, which may be useful as a solvent, include $C_1$ to $C_{15}$ halogenated aliphatic hydrocarbons; alternatively, $C_1$ to $C_{10}$ halogenated aliphatic hydrocarbons; or alternatively, $C_1$ to $C_5$ halogenated aliphatic hydrocarbons. Non-limiting examples of such halogenated aliphatic hydrocarbons, which may be utilized as a solvent, include carbon tetrachloride, chloroform, methylene chloride, dichloroethane, trichloroethane, and combinations thereof. Halogenated aromatic hydrocarbons, which may be useful as a solvent, include $C_6$ to $C_{20}$ halogenated aromatic hydrocarbons; or alternatively, $C_6$ to $C_{10}$ halogenated aromatic hydrocarbons. Non-limiting examples of suitable halogenated aromatic hydrocarbons include chlorobenzene, dichlorobenzene, and combinations thereof.

If a solvent is used for the metathesis reaction between ethylene and the unsaturated ester composition comprising, or consisting essentially of, unsaturated esters having an internal carbon-carbon double bond, the quantity of solvent can be any amount that facilitates the metathesis reaction. In some embodiments, the mass of the solvent is less than 30 times the mass of the unsaturated ester composition. In other embodiments, the mass of the solvent is less than 20 times the mass of the unsaturated ester composition; alternatively, less than 15 times the mass of the unsaturated ester composition; alternatively, less than 10 times the mass of the unsaturated ester composition; or alternatively, less than 5 times the mass of the unsaturated ester composition. In other embodiments, the mass of the solvent is from 2 times to 20 times the mass of the unsaturated ester composition; alternatively, from 3 times to 15 times the mass of the unsaturated ester composition; alternatively, 4 times to 15 times the mass of the unsaturated ester composition; or alternatively, from 5 times to 10 times the mass of the unsaturated ester composition.

The process to produce the unsaturated ester composition comprising, or consisting essentially of, unsaturated esters having an terminal carbon-carbon double bonds by the metathesis reaction may include steps to remove by products, impurities, and/or the optional solvent. An advantage of the present technique may lie in the potentially easy purification of the final products. Metathesis Scheme 1 provides an exemplary metathesis reaction between a single unsaturated ester molecule having internal carbon-carbon double bonds, which may be present in an unsaturated ester composition. It can be appreciated that the product mixture resulting from the metathesis reaction between ethylene and the unsaturated ester composition comprising, or consisting essentially of, unsaturated esters having an internal carbon-carbon double bond generally contains byproducts which have lower boiling points than the desired unsaturated esters having terminal carbon-carbon double bonds. It can also be appreciated that the unsaturated ester molecule having terminal carbon-carbon double bonds has a lower boiling point that the unconverted or partially converted unsaturated ester having internal carbon-carbon double bonds. For example, the materials having a boiling point lower that the unsaturated ester molecules having terminal carbon-carbon double bonds may be removed by flashing them off of the reaction mixture in a vacuum stripping process. The unconverted or partially converted unsaturated esters having an internal carbon-carbon double bond may then be separated from the unsaturated esters having terminal carbon-carbon double bonds via distillation and/or wiped film evaporation. Alternatively, the lower boiling by products and unconverted (or partially converted) unsaturated esters having an internal carbon-carbon double bonds may be separated from the desired unsaturated esters having an terminal carbon-carbon double bonds via distillation and/or wiped film evaporation. Other techniques may be used in addition to or place of vacuum stripping, including, for example, column chromatography, column distillation, and/or phase separation, among other techniques.

In an embodiment, the vacuum stripping process may be run under a vacuum of about 0.001 atmospheres (atm) to 0.5 atm, or under a vacuum of about 0.05 atm to 0.4 atm, or under a vacuum of 0.25 atm. In embodiments, the vacuum distillation may be run at a temperature of between about 15° C. to 150° C., at a temperature of 15° C. to a temperature of 100° C., or at a temperature of around 25° C. The time for the distillation depends on the molecular weights and vapor pressures of the components. If material having low boiling points are present (e.g., 1,3-propadiene resulting from the metathesis of two alkene groups separated by a methylene group) the vacuum distillation may only take a few minutes. In contrast, if there are lower vapor pressure components present (e.g., 1-decene) adequate separation may take several hours. In an embodiment, the vacuum distillation may be run for 5 minutes, 15 minutes, 1 hour, 2 hours, 6 hours, or longer. Alternatively or additionally, the unsaturated esters having an terminal carbon-carbon double bonds may be sparged with an inert gas to remove low boiling components, at a temperature between 25° C. and 250° C.; or, alternatively, between 50° C. and 200° C. The inert gas may be nitrogen, or any other suitable inert gas, such as argon.

Thermal Cracking of Unsaturated Natural Source Oils Having a Hydroxy Group

In an aspect, the unsaturated ester composition comprising, or consisting essentially of, unsaturated ester molecules having terminal carbon-carbon double bonds may be produced via thermal cracking. In a thermal cracking process, the source composition may be heated to a relatively high temperature under an inert atmosphere, potentially in the presence of a catalyst (e.g. a free radical initiator). Generally, the unsaturated esters having a terminal carbon-carbon double bonds (or the unsaturated esters compositions comprising or consisting essentially of, unsaturated esters having terminal carbon-carbon double bonds) may be produced by a) contacting the unsaturated ester molecules having internal carbon-carbon double bonds (or an unsaturated ester composition comprising, or consisting essentially of, unsaturated ester molecules having internal carbon-carbon double bonds) and heat, and b) forming unsaturated ester molecules having terminal carbon-carbon double bonds (or composition comprising, or consisting essentially of, unsaturated ester molecules having terminal carbon-carbon double bonds). Generally, the unsaturated ester molecules having terminal carbon-carbon double bonds (or composition comprising, or consisting essentially of, unsaturated ester molecules having terminal carbon-carbon double bonds) are formed at conditions capable of forming the unsaturated ester molecules having terminal carbon-carbon double bonds (or the unsaturated ester composition comprising, or consisting essentially of, unsaturated ester molecules having terminal carbon-carbon double bonds).

Generally, thermal cracking reaction works best with unsaturated ester composition comprising, or consisting essentially of, unsaturated ester molecules having a internal carbon-carbon double bond and a hydroxy group separated from the carbon-carbon double bond by a methylene group. One such unsaturated ester composition that may be utilized is castor oil. Thermal Cracking Scheme 1 provides a general thermal cracking reaction for one particular unsaturated ester having internal carbon-carbon bonds found within castor oil. One having ordinary skill in the art will appreciate that Thermal Cracking Scheme 1 is not limiting. The unsaturated ester compositions comprising, or consisting essentially of, unsaturated ester molecules having internal carbon-carbon double bonds described herein may contain additional unsaturated ester having internal carbon-carbon double bonds or may contain totally different unsaturated esters having internal carbon-carbon double bonds than what is shown in Thermal Cracking Scheme 1. Thermal Cracking Scheme 1 is merely a sample, non-limiting, representation of the thermal cracking reaction that may be utilized to produce a unsaturated ester molecule having terminal carbon-carbon double bonds. Additionally, one having ordinary skill in the art will appreciate that Thermal Cracking Scheme 1 only provides one of many expected by-products that would be produced by the thermal cracking reaction. Depending upon the actual composition of the unsaturated ester compositions comprising, or consisting essentially of, unsaturated ester molecules having internal carbon-carbon double bonds and the thermal cracking reaction conditions, other products, by-products, and impurities may be produced.

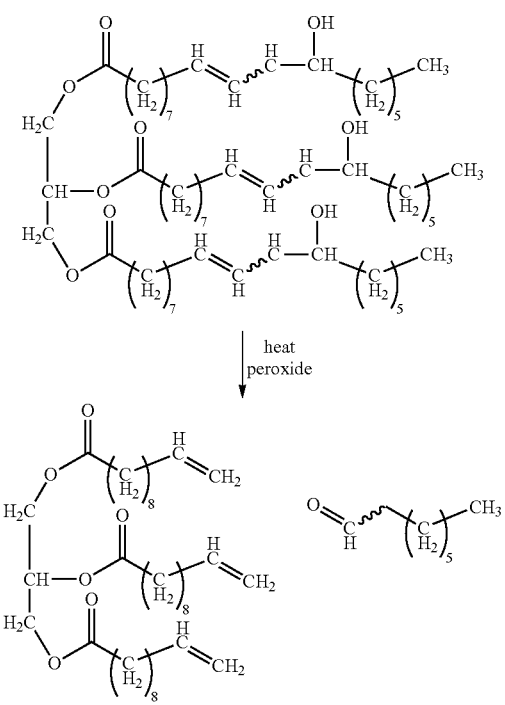

Thermal Cracking Scheme 1

The reaction may be run in a tubular reactor, a stirred tank reactor, a fixed bed reactor, a fluidized bed reactor, and a fractionation reactor, among others. The reactor may be packed to increase the surface area, for example, with stainless steel balls, milling pieces, or other materials. The packing material may also function as a catalyst, for example, alumina balls. The reaction may be carried out at a temperature of between about 250° C. to 700° C., or from 300° C. to 650° C., or from 400° C. to 600° C. One of ordinary skill in the art will recognize that different temperatures may lead to charring of the source composition, which may lower yields.

The free radical initiator may be any free radical initiator capable of forming free radicals under thermal conditions. For example, the free radical initiator may be selected from the general class compounds having a —N=N— group or a —O—O— group. Suitable classes of free radical initiators may include diazo compounds, dialkyl peroxides, hydroperoxides, and peroxy esters. For example, initiators that may be used in embodiments may include azobenzene, 2,2'-azobis(2-methylpropionitrile, 4,4'-azobis(4-cyanovaleric acid), 1,1'-azobis(cyclohexanecarbonitrile), 2,2'-azobis(2-methylpropane-), 2,2'-azobis(2-methylpropionamidine) dihydrochloride, methylpropionitrile, azodicarboxamide, tert-butyl hydroperoxide, di-tert-butyl peroxide, octylperbenzoate and benzoyl peroxide. In an embodiment, benzoyl peroxide may be used as the initiator.

The thermal cracking reaction may be run for about 5 minutes, 10 minutes, 30 minutes, 60 minutes, 2 hours, or longer. Generally, the yield of thermal cracking reactions may be low, e.g., about 30% to 50%. Particular types of source compositions, such as the castor bean oil discussed above (structure 4) may provide higher yields, as the hydroxyl group within one methylene group of the internal carbon-carbon double bond may assist the reaction. In this case, the yield may be about 50%. The low yields of this reaction may make purification desirable prior to forming thiol ester molecules or thiol ester compositions.

The process to produce the unsaturated ester composition comprising, or consisting essentially of, unsaturated esters having terminal carbon-carbon double bonds by a thermal cracking reaction may include steps to remove by-products, impurities, and/or the optional solvent. Thermal Cracking Reaction Scheme 1 provides an exemplary thermal cracking reaction between a single unsaturated ester molecule having internal carbon-carbon double bonds which may be present in an unsaturated ester composition. It can be appreciated that the product mixture resulting from the thermal cracking reaction produces by-products which have lower boiling points than the desired unsaturated esters having terminal carbon-carbon double bonds. It can also be appreciated that the unsaturated ester molecule having terminal carbon-carbon double bonds has a lower boiling point than the unconverted or partially converted unsaturated ester having internal carbon-carbon double bonds. For example, the materials having a boiling point lower than the unsaturated ester molecules having terminal carbon-carbon double bonds may be removed by flashing them off of the reaction mixture in a vacuum stripping process. The unconverted or partially converted unsaturated esters having an internal carbon-carbon double bonds may then be separated from the unsaturated esters having an terminal carbon-carbon double bonds via distillation and/or wiped film evaporation. Alternatively, the lower boiling by-products and unconverted (or partially converted) unsaturated esters having an internal carbon-carbon double bonds may be separated from the desired unsaturated esters having an terminal carbon-carbon double bonds via distillation and/or wiped film evaporation. Other techniques may be used in addition to or place of vacuum stripping, including, for example, column chromatography, column distillation, and/or phase separation, among other techniques.

In an embodiment, the vacuum stripping process may be run under a vacuum of about 0.001 atmospheres (atm) to 0.5 atm, or under a vacuum of about 0.05 atm to 0.4 atm, or under a vacuum of 0.25 atm. In embodiments, the vacuum distillation may be run at a temperature of between about 15° C. to 150° C., at a temperature of 15° C. to a temperature of 100° C., or at a temperature of around 25° C. The time for the distillation depends on the molecular weights and vapor pressures of the components. If material having low boiling points are present the vacuum distillation may only take a few minutes. In contrast, if there are lower vapor pressure components present adequate separation may take several hours. In embodiments, the vacuum distillation may be run for 5 minutes, 15 minutes, 1 hour, 2 hours, 6 hours, or longer. Alternatively or additionally, the terminal alkene composition may be sparged with an inert gas to remove material having a low boiling points, at a temperature between 25° C. and 250° C.; or, alternatively, between 50° C. and 200° C. The inert gas may be nitrogen, or any other suitable inert gas, such as argon.

Reaction of a Polyol with an Unsaturated Carboxylic Acid or an Unsaturated Carboxylic Acid Equivalent In an aspect, the unsaturated ester molecules having a terminal carbon-carbon double bonds (or the unsaturated esters compositions comprising or consisting essentially of, unsaturated esters having a terminal carbon-carbon double bonds) may be produced by a) contacting a polyol (or a composition comprising, consisting essentially of a polyol) and a carboxylic acid having a terminal carbon-carbon double bond and/or carboxylic acid derivative having a terminal carbon-carbon double bond (or composition comprising or consisting essentially of, a carboxylic acid having a terminal carbon-carbon double bond and/or a carboxylic acid derivative having a terminal carbon-carbon double bond) and b) forming unsaturated esters having a terminal carbon-carbon double bonds (or unsaturated ester composition comprising, or consisting essentially of, unsaturated ester molecules having terminal carbon-carbon double bonds). Generally, the unsaturated ester molecules having terminal carbon-carbon double bonds (or composition comprising, or consisting essentially of, unsaturated ester molecules having terminal carbon-carbon double bonds) are formed at conditions capable of forming the unsaturated ester molecules having terminal carbon-carbon double bonds (or the unsaturated ester composition comprising, or consisting essentially of, unsaturated ester molecules having terminal carbon-carbon double bonds). This process can be applied to any polyol, carboxylic acid having a terminal carbon-carbon double bond, or carboxylic acid derivative having a terminal carbon-carbon double bond described herein. The process for producing the unsaturated ester molecules having a terminal carbon-carbon double bonds (or the unsaturated esters compositions comprising or consisting essentially of, unsaturated esters having terminal carbon-carbon double bonds) can also include any additional process steps or process conditions described herein. Additionally, the process for producing the unsaturated ester molecules having a terminal carbon-carbon double bonds (or the unsaturated esters compositions comprising or consisting essentially of, unsaturated esters having terminal carbon-carbon double bonds) described herein.

The polyol that may be utilized in producing the unsaturated ester molecules having a terminal carbon-carbon double bonds (or the unsaturated esters compositions comprising, or consisting essentially of, unsaturated esters having terminal carbon-carbon double bonds) may be further described by its structural features. These structural features are independently described herein and may be utilized in any combination to describe the polyol.

In one aspect, the polyol used to produce the unsaturated ester molecules having a terminal carbon-carbon double bonds (or the unsaturated esters compositions comprising, or consisting essentially of, unsaturated esters having terminal carbon-carbon double bonds) may have 2 to 20 carbon atoms. In other embodiments, the polyol may have 2 to 12 carbon atoms; alternatively from 2 to 8 carbon atoms; alternatively from 2 to 5 carbon atoms. In further embodiments, the polyol may be a mixture of polyols having an average of 2 to 20 carbon atoms per polyol molecule; alternatively, an average of from 2 to 12 carbon atoms per polyol molecule; alternatively, an average of 2 to 8 carbon atoms; alternatively an average of 2 to 5 carbon atoms per polyol molecule.

In an embodiment, the polyol used to produce the unsaturated ester molecules having a terminal carbon-carbon double bonds (or the unsaturated esters compositions comprising or consisting essentially of, unsaturated esters having a terminal carbon-carbon double bonds) can have any number of hydroxy groups needed to produce the unsaturated esters compositions comprising or consisting essentially of, unsaturated esters having a terminal carbon-carbon double bonds as described herein. In some embodiments, the polyol may have 2 to 8 hydroxyl group; alternatively, 3 to 6 hydroxyl groups; alternatively, 2 to 4 hydroxyl groups; alternatively, 4 to 8 hydroxyl groups; alternatively, only 3 hydroxyl groups; alternatively, only 4 hydroxyl groups; alternatively, only 5 hydroxyl groups; or alternatively, only 6 hydroxyl groups. In an embodiment, mixtures of polyols may be used and the polyols may have an average at least 2 hydroxyl groups per polyol molecule; alternatively, at least 2.5 hydroxyl groups per polyol molecule; alternatively, 2.5 to 8 hydroxyl groups per polyol molecule; alternatively, an average of 2 to 6 hydroxyl groups per polyol molecule; alternatively, an average of 2.5 to 5 hydroxyl groups per polyol molecule; alternatively, an average of 2.5 to 4.5 hydroxyl group per polyol molecule; alternatively, an average of 2.5 to 3.5 hydroxyl group per polyol molecule; alternatively, an average of 3 to 4 hydroxyl group per polyol molecule; alternatively, an average of about 3 hydroxyl groups per polyol molecule; alternatively, an average of about 4 hydroxyl groups per polyol molecule; alternatively, an average of about 5 hydroxyl groups per polyol molecule; or alternatively an average of about 6 hydroxy groups per polyol molecule.

In an embodiment, the polyol or mixture of polyols used to produce the unsaturated ester molecules having a terminal carbon-carbon double bonds (or the unsaturated esters compositions comprising or consisting essentially of, unsaturated esters having a terminal carbon-carbon double bonds) has a molecular weight or average molecular weight less than 300. In other embodiments, the polyol or mixture of polyols have a molecular weight or average molecular weight less than 250; alternatively less than 200; alternatively, less than 150; or alternatively, less than 100.

In an embodiments, the polyol that formed the residue of the polyol is a diol, triol, a tetraol, pentaol, hexaol, or combination thereof; alternatively a diol, triol, tetraol or combination thereof; or alternatively, a triol, tetraol or combination thereof. In some embodiments, the polyol that formed the residue of the polyol is a diol; alternatively, a triol; alternatively, a tetraol; alternatively, a pentaol; or alternatively, a hexaol. Suitable polyols that may used to produce the unsaturated esters compositions comprising or consisting essentially of, unsaturated esters having a terminal carbon-carbon double bonds include ethane diol, propanediol, butanediol, pentanediol, hexanediol, cyclohexane diol, phenylethane diol, cyclohexanedimethanol, dimethyolpropane, benzenedimethanol, cyclohexanetriol, trihydroxybenzene, trimethyolethane, trimethylolpropane, trimethylolbutane, glycerol, pentaerythritol, sorbitol, or any combination thereof; alternatively, cyclohexane diol, trimethylol propane, glycerol, pentaerythritol, or combinations thereof; alternatively, glycerol, pentaerythritol, or combinations thereof. In some embodiments, the polyol used to produce the unsaturated esters compositions comprising or consisting essentially of, unsaturated esters having a terminal carbon-carbon double bonds include 1,2-ethanediol, 1,3-propanediol, 1,4-butanediol, 1,5-pentanediol, 1,6-hexanediol, dimethylolpropane, neopentyl glycol, 2-propyl-2-ethyl-1,3-propanediol, 1,2-propanediol, 1,2-butanediol, 1,3-butanediol, 1,4-butanediol, diethylene glycol, triethylene glycol, polyethylene glycol, dipropylene glycol, tripropylene glycol, polypropylene glycol, 1,1-cyclohexanedimethanol, 1,2-cyclohexanedimethanol, 1,3-cyclohexanedimethanol, 1,4-cyclohexanedimethanol, 1,3-dioxane-5,5-dimethanol, 1-phenyl-1,2-ethanediol, trimethylolpropane, trimethylolethane, trimethylolbutane, glycerol, 1,2,5-hexanetriol, pentaerythritol, ditrimethylolpropane, diglycerol, ditrimethylolethane, 1,3,5-trihydroxybenzene, 1,2-benzenedimethanol, 1,3-benzenedimethanol, 1,4-benzenedimethanol, 1-phenyl-1,2-ethanediol, sorbitol, or any combination thereof. In other embodiments, the polyol that may be used to produce the unsaturated esters compositions comprising or consisting essentially of, unsaturated esters having a terminal carbon-carbon double bonds may be trimethylolpropane, glycerol, pentaerythritol, or combinations thereof; alternatively, trimethylolpropane; alternatively, glycerol; alternatively, pentaerythritol; or alternatively sorbitol.

The unsaturated carboxylic acid having a terminal carbon-carbon double bond used to produce the unsaturated ester molecules having a terminal carbon-carbon double bonds (or the unsaturated esters compositions comprising or consisting essentially of, unsaturated esters having terminal carbon-carbon double bonds) via reaction with the polyol can be any unsaturated carboxylic acid having a terminal carbon-carbon double bond. Alternatively, the unsaturated carboxylic acid equivalent having a terminal carbon-carbon double bond may be any unsaturated carboxylic acid equivalent having a terminal carbon-carbon double bond. The unsaturated carboxylic acid or carboxylic acid equivalent having a terminal carbon-carbon double bond may be further described by their structural features. These structural features are independently described herein and may be utilized in any combination to describe the unsaturated carboxylic acid or unsaturated carboxylic acid equivalent having a terminal carbon-carbon double bond.

In an embodiment, the unsaturated carboxylic acid equivalent having terminal carbon-carbon double bond may be a simple ester of a carboxylic acid having a terminal carbon-carbon double bond. In some embodiments, the carboxylic acid equivalent is a methyl ester, ethyl ester, n-propyl ester, iso-propyl ester, n-butyl ester, or t-butyl ester of the carboxylic acid having a terminal carbon-carbon double bond. In other embodiments, the carboxylic acid equivalent is a methyl ester or ethyl ester of the carboxylic acid having a terminal carbon-carbon double bond. In some embodiments, the carboxylic acid equivalent is a methyl ester of a carboxylic acid having a terminal carbon-carbon double bond. In other embodiments, the carboxylic acid equivalent is a ethyl ester of a carboxylic acid having a terminal carbon-carbon double bond. In another embodiment, the carboxylic acid equivalent is an anhydride of a carboxylic acid having a terminal carbon-carbon double bond.

When discussing the structural features of the unsaturated carboxylic acid equivalent having a terminal carbon-carbon double bond, the structural features will be described as those of the parent carboxylic acid having a terminal carbon-carbon double bond. For example, an unsaturated carboxylic acid equivalent having a terminal carbon-carbon double bond and 7 carbon atoms refers to the same component forming the ester group with the polyol as a carboxylic acid having a terminal double bond and 7 carbon atoms.

The unsaturated carboxylic acid or unsaturated carboxylic acid equivalent having a terminal carbon-carbon double bond may be further described by its structural features. These structural features are independently described herein and may be utilized in any combination to describe the carboxylic acid or carboxylic acid equivalent having a terminal carbon-carbon double bond.

In an embodiment, the unsaturated carboxylic acid or unsaturated carboxylic equivalent having a terminal carbon-carbon double bond is linear. In some embodiments, the unsaturated carboxylic acid or unsaturated carboxylic equivalent having a terminal carbon-carbon double bond is branched. In further embodiments, the unsaturated carboxylic acid or unsaturated carboxylic equivalent having a terminal carbon-carbon double bond is substantially devoid of other functional groups. In further embodiments, the unsaturated carboxylic acid or unsaturated carboxylic equivalent having a terminal carbon-carbon double bond is devoid of other functional groups.

In an embodiment, the unsaturated carboxylic acid or unsaturated carboxylic equivalent having a terminal carbon-carbon double bond may have at least 4 carbon atoms; alternatively, at least 6 carbon atoms; or alternatively, at least 8 carbon atoms. In some embodiments, the unsaturated carboxylic acid or unsaturated carboxylic equivalent having a terminal carbon-carbon double bond may have from 4 to 20 carbon atoms; alternatively, from 6 to 18 carbon atoms; alternatively, from 8 to 14 carbon atoms; alternatively, from 10 to 11 carbon atoms; alternatively, only 10 carbon atoms; or alternatively, only 11 carbon atoms. In some embodiments, a mixture of unsaturated carboxylic acid having a terminal carbon-carbon double bond may be used; or alternatively, a mixture of unsaturated carboxylic acid equivalents having a terminal carbon-carbon double bond may be used. When mixtures of unsaturated carboxylic acid or unsaturated carboxylic equivalents having a terminal carbon-carbon double bond are used the unsaturated carboxylic acid or unsaturated carboxylic equivalent having a terminal carbon-carbon double bond may have an average of at least 6 carbon atoms; or alternatively, at least 8 carbon atoms; alternatively, alternatively, from 6 to 18 carbon atoms; alternatively, from 8 to 14 carbon atoms; alternatively, from 10 to 11 carbon atoms; alternatively, about 10 carbon atoms; or alternatively, about 11 carbon atoms.

Suitable unsaturated carboxylic acid having a terminal carbon-carbon double bond may be 3-butenoic acid, a 4-pentenoic acid, a 5-hexenoic acid, a 6-heptenoic acid, a 7-octenoic acid, a 8-nonenoic acid, a 9-decenoic acid, a 10-undecenoic acid, a 11-dodecenoic acid, a 12-tridecenoic acid, a 13-tetradecenoic acid, a 14-pentadecenoic acid, a 15-hexadecenoic acid, a 16-heptadecenoic acid, a 17-octadecenoic acid, a 18-nonadecenoic acid, a 19-eicosenoic acid, or any combination thereof. In some embodiments, the carboxylic acid residues having a thiol group located on the terminal carbon atom include a 5-hexenoic acid, a 6-heptenoic acid, a 7-octenoic acid, a 8-nonenoic acid, a 9-decenoic acid, a 10-undecenoic acid, a 11-dodecenoic acid, a 12-tridecenoic acid, a 13-tetradecenoic acid, a 14-pentadecenoic acid, a 15-hexadecenoic acid, a 16-heptadecenoic acid, a 17-octadecenoic acid, or any combination thereof; alternatively, a 7-octenoic acid, a 8-nonenoic acid, a 9-decenoic acid, a 10-undecenoic acid, a 11-dodecenoic acid, a 12-tridecenoic acid, a 13-tetradecenoic acid, or any combination thereof; or alternatively, 9-decenoic acid, a 10-undecenoic acid, or any combination thereof. In other embodiments, the carboxylic acid residues having a terminal carbon-carbon double bond may be a 5-hexenoic acid; alternatively, a 6-heptenoic acid; alternatively, a 7-octenoic acid; alternatively, a 8-nonenoic acid; alternatively, a 9-decenoic acid; alternatively, a 10-undecenoic acid; alternatively, a 11-dodecenoic acid; alternatively, a 12-tridecenoic acid; alternatively, a 13-tetradecenoic acid; alternatively, a 14-pentadecenoic acid; alternatively, a 15-hexadecenoic acid; alternatively, a 16-heptadecenoic acid; or alternatively, a 17-octadecenoic acid. Suitable unsaturated carboxylic acid equivalents having a terminal carbon-carbon double bond may be described as those based upon any unsaturated carboxylic acid equivalent having a terminal carbon-carbon double bond described herein (e.g. methyl 9-decanoate or methyl 10-undecenoate).

The equivalent ratio of unsaturated carboxylic acid or unsaturated carboxylic equivalent having a terminal carbon-carbon double bond to equivalents of polyol hydroxyl groups (hereinafter "unsaturated carboxylic acid group to polyol hydroxyl group equivalent ratio") utilized in the process to produce the unsaturated ester molecules having a terminal double bond (or the desired unsaturated ester composition comprising unsaturated ester molecules having terminal carbon-carbon double bonds) may be any unsaturated carboxylic acid group to polyol hydroxyl group equivalent ratio that produces the unsaturated ester molecules having a terminal carbon-carbon double bonds (or the desired unsaturated ester composition comprising unsaturated ester molecules having terminal carbon-carbon double bonds). In some embodiments, the unsaturated carboxylic acid group to polyol hydroxyl group equivalent ratio is greater than 1:1. In other embodiments, the unsaturated carboxylic acid group to polyol hydroxyl group molar ratio is greater than 1.1:1; alternatively, greater than 1.2:1. In other embodiments, the carboxylic acid group to polyol hydroxyl group molar ratio ranges from 1:1 to 2:1; alternatively, from 1.1:1 to 1.8, or alternatively, from 1.2:1 to 1.6:1.

In an embodiment, the reaction between the polyol and the unsaturated carboxylic acid or unsaturated carboxylic equivalent having a terminal carbon-carbon double bond is catalyzed. In some embodiments, the catalyst is a mineral acid, such as sulfuric or phosphoric acid. In other embodiments, the catalyst is an organic acid. Non-limiting examples of organic acids, which may be utilized as a catalyst, include methane sulfonic acid and toluene sulfonic acid. In other embodiments, the catalyst may be an organic base. One class of organic bases, which may be utilized to catalyst the reaction between the polyol and the unsaturated carboxylic acid or unsaturated carboxylic equivalent having a terminal carbon-carbon double bond, are metal alkoxides. Non-limiting example of suitable metal alkoxides include sodium methoxide, sodium ethoxide, potassium methoxide, potassium ethoxide, sodium t-butoxide, and potassium t-butoxide. Another class of organic catalysts, which may be utilized to catalyst the reaction between the polyol and the unsaturated carboxylic acid or unsaturated carboxylic equivalent having a terminal carbon-carbon double bond, is metal carboxylates such as sodium acetate of potassium acetate. In yet other embodiments, the catalyst may be organometallic catalyst. Examples of organic metallic catalyst, which may be utilized to catalyst the reaction between the polyol and the unsaturated carboxylic acid or unsaturated carboxylic equivalent having a terminal carbon-carbon double bond, are organotin catalyst such as dibutyltin oxide. Other suitable types of catalyst will be apparent to those of skill in the art and are to be considered within the scope of the present invention.

In an embodiment, the reaction between the polyol and the unsaturated carboxylic acid or carboxylic acid equivalent having a terminal carbon-carbon double bond occurs in the presence of a solvent. In some embodiments the reaction between the polyol and the unsaturated carboxylic acid or carboxylic acid equivalent having a terminal carbon-carbon double bond occurs in the substantial absence of a solvent. In an embodiment, wherein the reaction between the polyol and the unsaturated carboxylic acid or carboxylic acid equivalent having a terminal carbon-carbon double bond occurs in the presence of a solvent, the solvent may be selected from aromatic hydrocarbons, aliphatic hydrocarbons, organic ethers, halogenated aliphatic hydrocarbons, aromatic hydrocarbons, halogenated aromatic hydrocarbons, and combinations thereof. Aliphatic hydrocarbons, which may be useful as a solvent, include $C_4$ to $C_{20}$ hydrocarbons, or alternatively, $C_5$ to $C_{10}$ hydrocarbons, and may be cyclic or acyclic and include linear or branched isomers, unless otherwise specified. Non-limiting examples of suitable acyclic aliphatic solvents include pentane, hexane, heptane, octane, and combinations thereof. Non-limiting examples of suitable cyclic aliphatic solvents include cyclohexane, methyl cyclohexane, and combinations thereof. Aromatic hydrocarbons, which may be useful as a solvent, include $C_6$ to $C_{20}$ aromatic hydrocarbons; or alternatively, $C_6$ to $C_{10}$ aromatic hydrocarbons. Non-limiting examples of suitable aromatic hydrocarbons include benzene, toluene, xylene (including ortho-xylene, meta-xylene, para-xylene, or mixtures thereof), and ethylbenzene, or combinations thereof. Organic ethers which may be uses as a solvent include $C_2$ to $C_{20}$ organic ethers; alternatively, $C_2$ to $C_{10}$ organic ethers; or alternatively, $C_2$ to $C_5$ organic ethers. Suitable ether solvents may be cyclic or acyclic. Non-limiting examples of suitable ethers which may be useful as a solvent include dimethyl ether, diethyl ether, methyl ethyl ether, monoethers or diethers of glycols (e.g., dimethyl glycol ether), furans, substituted furans, dihydrofuran, substituted dihydrofurans, tetrahydrofuran (THF), substituted tetrahydrofurans, tetrahydropyrans, substituted tetrahydropyrans, 1,3-dioxanes, substituted 1,3-dioxanes, 1,4-dioxanes, substituted 1,4-dioxanes, or mixtures thereof. In an embodiment, each substituent of a substituted furan, substituted dihydrofuran, substituted tetrahydrofuran, substituted tetrahydropyran, substituted 1,3-dioxane, or substituted 1,4-dioxane, can be a $C_1$ to $C_5$ alkyl group. Halogenated aliphatic hydrocarbons, which may be useful as a solvent, include $C_1$ to $C_{15}$ halogenated aliphatic hydrocarbons; alternatively, $C_1$ to $C_{10}$ halogenated aliphatic hydrocarbons; or alternatively, $C_1$ to $C_5$ halogenated aliphatic hydrocarbons. Non-limiting examples of such halogenated aliphatic hydrocarbons, which may be utilized as a solvent, include carbon tetrachloride, chloroform, methylene chloride, dichloroethane, trichloroethane, and combinations thereof. Halogenated aromatic hydrocarbons, which may be useful as a solvent, include $C_6$ to $C_{20}$ halogenated aromatic hydrocarbons; or alternatively, $C_6$ to $C_{10}$ halogenated aromatic hydrocarbons. Non-limiting examples of suitable halogenated aromatic hydrocarbons include chlorobenzene, dichlorobenzene, and combinations thereof.

When a solvent is used for the reaction between the polyol and the unsaturated carboxylic acid or carboxylic acid equivalent having a terminal carbon-carbon double bond, the quantity of solvent can be any amount that facilitates the reaction. In some embodiments, the mass of the solvent is less than 30 times the mass of the unsaturated carboxylic acid or carboxylic acid equivalent having a terminal carbon-carbon double bond. In other embodiments, the mass of the solvent is less than 20 times the mass of the unsaturated carboxylic acid or carboxylic acid equivalent having a terminal carbon-carbon double bond; alternatively, less than 15 times the mass of the unsaturated carboxylic acid or carboxylic acid equivalent having a terminal carbon-carbon double bond; alternatively, less than 10 times the mass of the unsaturated carboxylic acid or carboxylic acid equivalent having a terminal carbon-carbon double bond; or alternatively, less than 5 times the mass of the unsaturated carboxylic acid or carboxylic acid equivalent having a terminal carbon-carbon double bond. In other embodiments, the mass of the solvent is from 2 times to 20 times the mass of the unsaturated carboxylic acid or carboxylic acid equivalent having a terminal carbon-carbon double bond; alternatively, from 3 times to 15 times the mass of the unsaturated carboxylic acid or carboxylic acid equivalent having a terminal carbon-carbon double bond; or alternatively, from 5 times to 10 times the mass of unsaturated carboxylic acid or carboxylic acid equivalent having a terminal carbon-carbon double bond.

The reaction of the polyol and the unsaturated carboxylic acid or unsaturated carboxylic equivalent having a terminal carbon-carbon double bond can occur in a batch reactor or a continuous reactor, as described herein.

The reaction between the polyol and unsaturated carboxylic acid or unsaturated carboxylic equivalent having a terminal carbon-carbon double bond can be performed at any temperature capable of forming the unsaturated ester molecules having terminal carbon-carbon double bonds (or the desired unsaturated ester composition comprising unsaturated ester molecules having terminal carbon-carbon double bonds). In some embodiments, the polyol and the unsaturated carboxylic acid or unsaturated carboxylic equivalent having a terminal carbon-carbon double bond can be reacted at a temperature greater than 80° C. In other embodiments, the polyol and the unsaturated carboxylic acid or unsaturated carboxylic equivalent having a terminal carbon-carbon double bond can be reacted at a temperature greater than 100° C.; alternatively, greater than 120° C.; or alternatively, greater than 140° C. In yet other embodiments, the polyol and the unsaturated carboxylic acid or unsaturated carboxylic equivalent having a terminal carbon-carbon double bond can be reacted at a temperature from 80° C. to 300° C.; alternatively, from 100° C. to 290° C.; alternatively, from 120° C. to 280° C.; or alternatively, from 140° C. to 260° C.

In an embodiment, the reaction between the polyol and the unsaturated carboxylic acid or unsaturated carboxylic equivalent having a terminal carbon-carbon double bond is performed under conditions which allow water (for carboxylic acid and carboxylic acids having terminal carbon-carbon double bonds) or a simple alcohols (for simple esters of the carboxylic acid having terminal carbon-carbon double bonds) to be removed from the reaction solution as reaction between the polyol and the unsaturated carboxylic acid or unsaturated carboxylic equivalent having a terminal carbon-carbon double bond progresses. One such method the may be utilized is reactive distillation. In some embodiments, the solvent, if utilized, is chosen so that it may assist in the removal of the water or simple alcohol by forming an azeotrope. Other techniques are known to those having ordinary skill in the art.

The time required for the reaction between the reaction between the polyol and the unsaturated carboxylic acid or unsaturated carboxylic equivalent having a terminal carbon-carbon double bond can be any time required to form the unsaturated ester molecules having terminal carbon-carbon double bonds (or the desired unsaturated ester composition comprising unsaturated ester molecules having terminal carbon-carbon double bonds). Generally, the reaction time is at least 5 minutes. In some embodiments, the reaction time is at least 15 minutes; alternatively, at least 30 minutes; or alternatively, at least 45 minutes. In some embodiments, the reaction time ranges from 5 minutes to 48 hours; alternatively, from 15 minutes to 36 hours; alternatively, from 30 minutes to 24 hours; or alternatively, from 45 minutes and 12 hours.

When a continuous reactor is used for the reaction between the polyol and the unsaturated carboxylic acid or unsaturated carboxylic equivalent having a terminal carbon-carbon double bond, a polyol weight space velocity may range from 0.1 to 5. Alternatively, the polyol weight hourly space velocity may range from 0.15 to 4; alternatively, from 0.2 to 3.5; or alternatively, from 0.25 to 3.

The reaction between the polyol and the unsaturated carboxylic acid or unsaturated carboxylic equivalent having a terminal carbon-carbon double bond can be performed at any reaction pressure that maintains the polyol and the thiol containing carboxylic acid and/or thiol containing carboxylic acid derivative in a liquid state. In some embodiments, the reaction between the polyol and the unsaturated carboxylic acid or unsaturated carboxylic equivalent having a terminal carbon-carbon double bond is performed at a pressure ranging from 0 psia to 2000 psia; from 0 psia to 1000 psia; alternatively, from 0 psia and 500 psia; or alternatively, 0 psia to 300 psia.

The process to produce unsaturated ester molecules having terminal carbon-carbon double bonds (or the unsaturated ester composition comprising, or consisting essentially of, unsaturated esters having an terminal carbon-carbon double bonds) by the reaction between the polyol and the unsaturated carboxylic acid or unsaturated carboxylic equivalent having a terminal carbon-carbon double bond may include steps to remove by products, impurities, and/or the optional solvent. Materials having low boiling point may be removed by flashing them off of the reaction mixture in a vacuum stripping process. Unreacted polyol, if present and unreacted unsaturated carboxylic acid or unsaturated carboxylic equivalent having a terminal carbon-carbon double bond may be separated from the unsaturated esters having terminal carbon-carbon double bonds via distillation and/or wiped film evaporation. Alternatively, the low boiling materials and unconverted polyol (if present) and unreacted unsaturated carboxylic acid or unsaturated carboxylic equivalent having a terminal carbon-carbon double bond may be separated from the desired unsaturated esters having an terminal carbon-carbon double bonds via distillation and/or wiped film evaporation. Other techniques may be used in addition to or place of vacuum stripping, including, for example, column chromatography, column distillation, and/or phase separation, among other techniques.

In an embodiment, the vacuum stripping process may be run under a vacuum of about 0.001 atmospheres (atm) to 0.5 atm, or under a vacuum of about 0.05 atm to 0.4 atm, or under a vacuum of 0.25 atm. In embodiments, the vacuum distillation may be run at a temperature of between about 15° C. to 150° C., at a temperature of 15° C. to a temperature of 100° C., or at a temperature of around 25° C. In an embodiment, the vacuum distillation may be run for 5 minutes, 15 minutes, 1 hour, 2 hours, 6 hours, or longer. Alternatively or additionally, the unsaturated esters having an terminal carbon-carbon double bonds may be sparged with an inert gas to remove low boiling components, at a temperature between 25° C. and 250° C.; or, alternatively, between 50° C. and 200° C. The inert gas may be nitrogen, or any other suitable inert gas, such as argon.

Polythiourethane Compositions

In an aspect, the thiol ester molecules described herein and the thiol ester compositions described herein may be utilized to produce polythiourethanes. The polythiourethanes can be described as a reaction product of any thiol ester molecule (or thiol ester composition) described herein and isocyanate molecule (or isocyanate composition) described herein. Generally, the polythiourethane of the present invention comprises multiple thiourethane groups having structure U1:

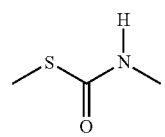

where the undesignated valancies represent the remainder of the structure of the polythiourethane including additional thiourethane groups having structure U1. The presence of the thiourethane group U1 can be determined using techniques known to those skilled in the art (for example Infrared Spectroscopy, Raman Spectroscopy, and or $^{13}$C NMR).

The polythiourethane of the present invention can be described as having a repeating unit PTU1:

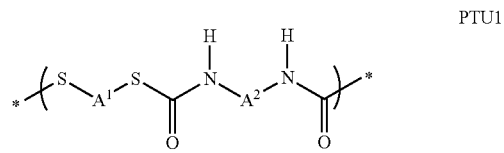

where the undesignated valancies represent the remainder of the structure of the polymer including additional repeating units PTU1. In embodiments, the backbone of the polythiourethane having repeating unit PTU1 is linear; or alternatively, the backbone of the polythiourethane having repeating unit PTU1 is crosslinked. When the backbone of the polythiourethane having repeating unit PTU1 is crosslinked, $A^1$ and/or $A^2$ further comprise additional repeating units PTU1. The repeating unit PTU1 of the polythiourethane is comprised of two different units: T1 and I2.

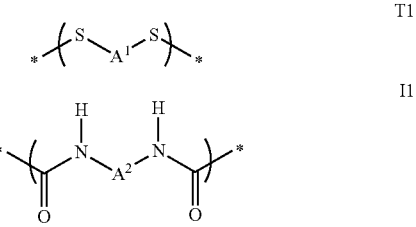

Generally, unit T1 of the polythiourethane is derived from a thiol ester molecule of a thiol ester composition and unit I1 of the polythiourethane is derived from an isocyanate of an isocyanate composition. Thus, $A^1$ represents the remainder of the thiol ester molecule (including ester groups, any other groups present in the thiol ester molecule, and optionally additional repeating units PTU1), and $A^2$ represents the remainder of the isocyanate molecule (including any other groups present in the isocyanate molecule and optionally additional repeating units PTU1). Because units T1 and I1 are derived from two different materials, the structures of these units are independent of each other. Therefore, the polythiourethanes having the repeating unit PTU1 can be comprised of any combination of units T1 and I1. Thus, the polythiourethane having the repeating unit PTU1 can be described as the reaction product of a thiol ester molecules and an isocyanate where unit T1 can be derived from any thiol ester described herein and unit I1 can be derived from any isocyanate described herein.

The polythiourethane of the present invention can alternatively be described as a reaction product of a thiol ester composition and an isocyanate composition. The thiol ester composition and the isocyanate are independent elements of the polythiourethane. Therefore, the polythiourethane can be described as a polythiourethane product of any combination of the thiol ester composition described herein and the isocyanate composition described herein. In aspects, the polythiourethane can be linear. In other aspects, the polythiourethane can be crosslinked. When the polythiourethane is crosslinked, either the thiol ester molecules have greater than 2 thiol groups per thiol ester molecule or the isocyanates have greater than 2 isocyanate groups per isocyanate molecule. Alternatively, when the polythiourethane is crosslinked the thiol ester molecules have greater than 2 thiol groups per thiol ester molecule and the isocyanates have greater than 2 isocyanate groups per isocyanate molecule.

Generally, the thiol ester composition comprises thiol ester molecules having at least 2 thiol groups and the isocyanate composition comprises isocyanate molecules having at least 2 isocyanate groups. Additional embodiments regarding the number or average number of thiol groups present in the thiol ester molecules of the thiol ester composition are described herein and are generally applicable to the description of the polythiourethane as a reaction product of a thiol ester composition and an isocyanate composition. Additional embodiments regarding the number or average number of isocyanate groups present in the isocyanate molecules of the isocyanate composition are described herein and are generally applicable to the description of the polythiourethane as a reaction product of a thiol ester composition and an isocyanate composition.

In embodiments, the thiol ester molecules composition utilized to produce the polythiourethane composition can comprise a hydroxy thiol ester molecules (hydroxy thiol ester composition); or alternatively, a crosslinked thiol ester molecules (crosslinked thiol ester composition). Additional aspects of the thiol ester molecules (e.g. average number of thiol groups per thiol ester molecule, thiol sulfur content etc. . . . ) are described herein and can be utilized to further describe the thiol esters of the thiol ester compositions. Besides the thiol ester molecules described herein, other suitable thiol ester compositions will be apparent to those persons having ordinary skill in the art, can be used, and are to be considered within the scope of the present invention.

Generally the isocyanates can comprise, singly or in any combination, any isocyanate described herein. In embodiments, the isocyanate can comprise aliphatic isocyanates, cycloaliphatic isocyanates, aromatic isocyanates, or mixtures thereof. In some embodiments, the isocyanate can comprise an aliphatic isocyanate; alternatively, a cycloaliphatic isocyanate; or alternatively, an aromatic isocyanate composition. Particular isocyanates having at least two isocyanate groups are described herein and can generally be utilized in the isocyanate compositions describing the polythiourethane as a reaction product of a thiol ester composition and an isocyanate composition. Additionally, other aspects of the isocyanates (e.g. number or average number of isocyanate groups per isocyanate molecule, etc. . . . ) are described herein and can be utilized to further describe the isocyanate.

Generally, the thiol ester composition and the isocyanate composition are independent elements of the polythiourethane described as the reaction product of a thiol ester composition and an isocyanate composition. Therefore, the polythiourethane can be described as the reaction product of any combination of the thiol ester composition described herein and the isocyanate composition described herein. In embodiments, the polythiourethane can be described as the reaction product of a thiol ester composition with isocyanate composition comprising an isocyanate having at least two isocyanate groups. In embodiments, the polythiourethane can be described as the reaction product of a hydroxy thiol ester composition and an isocyanate composition. Therefore, the polythiourethane composition can be described as the reaction product of any combination of the hydroxy thiol ester composition described herein and the isocyanate composition described herein.

In some embodiments, the polythiourethane can be described as the reaction product of a crosslinked thiol ester composition and an isocyanate composition. Therefore, the polythiourethane composition can be described as the reaction product of any combination of the crosslinked thiol ester composition described herein and the isocyanate composition described herein.

In some embodiments, the polythiourethanes of the present invention can be described as a product produced by any process described herein capable of producing the polythiourethane composition and can be further described as being produced using any embodiments of the processes described herein.

In embodiments, the polythiourethane of the present invention can be further described by its properties. In some embodiments, the polythiourethane described as the reaction product of a thiol ester composition and an isocyanate composition can have a glass transition temperature ranging from $-100°$ C. to $250°$ C. In other embodiments, the polythiourethane of the present invention has a glass transition temperature ranging from $-50°$ C. to $150°$ C.; or alternatively, ranging from $-50°$ C. to $100°$ C.

In an aspect, the polythiourethanes can have other desirable properties. For example, the polythiourethanes of the present invention can have desirable Young's modulus and elongations at break, which can be measured using ASTM D638-03. In embodiments, the polythiourethanes can have a Young's modulus greater than 0.1 MPa; or alternatively, ranging from 0.1 MPa to 7,000 MPa. In some embodiments, the polythiourethanes have a Young's modulus ranging from 2 to 6 MPa; alternatively, from 6 MPa to 60 MPa; alternatively, 60 MPa to 600 MPa; or alternatively, from 600 MPa to 4,500 MPa. In an aspect, the polythiourethanes can have an elongation at break less than 100 percent; or alternatively, greater than 100 percent. In an embodiment, the greater than 150 percent; alternatively, greater than 200 percent; alternatively, ranging from 100 percent to 900 percent, or alternatively, ranging from 200 to 700 percent. In some embodiments, the polythiourethanes can have an elongation at break less than 10 percent; or alternatively, ranging from 10 percent to 100 percent. In embodiments, the polythiourethanes can have any combination of the Young's modulus described herein and the elongation at break as described herein.

Process of Making Polythiourethane

In an aspect, a method of making the polythiourethane of the present invention comprises contacting a thiol ester composition and an isocyanate composition. In an embodiment of the present invention, the method of producing the polythiourethane composition comprises contacting the thiol ester composition and the isocyanate composition to produce a mixture and curing the mixture to produce the polythiourethane.

Generally, the thiol ester composition utilized to form the mixture can be any thiol ester composition described herein. In embodiments, the thiol ester composition can comprise the hydroxy thiol ester molecules (hydroxy thiol ester composition); or alternatively, the crosslinked thiol ester molecules (crosslinked thiol ester composition. Additional aspects of the thiol ester molecules (e.g. average number of thiol groups per thiol ester molecule, thiol sulfur content etc. . . . ) are described herein and can be utilized to further describe the thiol ester compositions. Other suitable thiol ester compositions will be apparent to those persons having ordinary skill in the art, can be used, and are to be considered within the scope of the present invention.

Generally, the isocyanate utilized to form the mixture can comprise, singly or in any combination, any isocyanate described herein. In an embodiment, the isocyanate composition can comprise aliphatic isocyanates, cycloaliphatic isocyanates, aromatic isocyanates, or mixtures thereof. In some embodiments, the isocyanate composition can comprise an aliphatic isocyanate; alternatively, a cycloaliphatic isocyanate; or alternatively, an aromatic isocyanate composition. Other isocyanate compositions are described herein and can generally be utilized to form the mixture comprising the thiol ester composition and the isocyanate composition. Additional aspects of the isocyanates (e.g. number or average number of isocyanate groups per isocyanate molecule etc. . . . ) are described herein and can be utilized to further describe the isocyanates.

Generally, the thiol ester composition and the isocyanate ester composition are independent elements of the mixture comprising a thiol ester composition and an isocyanate composition. Therefore, the mixture comprising a thiol ester composition and an isocyanate composition can comprise any thiol ester composition described herein and any isocyanate composition described herein. In embodiments, the mixture can comprise a thiol ester composition and an isocyanate composition comprising an isocyanate having at least two isocyanate groups. In embodiments, the mixture can comprise a thiol ester composition and an isocyanate composition comprising an aliphatic isocyanate having at least two isocyanate groups, a cycloaliphatic isocyanate having at least two isocyanate groups, an aromatic isocyanate having at least two isocyanate groups, or mixtures thereof. In some embodiments, the mixture can comprise a thiol ester composition and an isocyanate composition comprising an aliphatic isocyanate having at least two isocyanate groups; alternatively, a cycloaliphatic isocyanate having at least two isocyanate group; or alternatively, an aromatic isocyanate having at least two isocyanate groups. Particular aliphatic, cycloaliphatic, and aromatic isocyanates having at least two isocyanate groups are described herein and can generally be utilized in the isocyanate compositions describing the polythiourethane as a reaction product of a thiol ester composition and an isocyanate composition. Additionally, other aspects of the isocyanate materials (e.g. number or average number of isocyanate groups per isocyanate molecule, etc. . . . ) are described herein and can be utilized to further describe the isocyanate composition utilized in describing the polythiourethane as a reaction product of a thiol ester composition and an isocyanate composition.

Generally, the thiol ester composition and the isocyanate composition can be combined in any functional group equivalent ratio that can produce a polythiourethane. The functional group equivalent ratio relates the ratio of the number of functional groups in the thiol ester composition capable of reacting with an isocyanate of the isocyanate composition to form a thiourethane group to the number of isocyanate groups in the isocyanate composition. Generally, the functional group equivalent ratio is provided by the term "XH:NCO equivalent ratio" where XH represents the equivalents of thiol groups and the alcohol groups present in the thiol ester composition and NCO represent the equivalents of isocyanate groups present in the isocyanate composition. One skilled in the art will recognize which thiol ester composition comprises only thiol groups and which thiol ester composition comprises thiol groups and alcohol groups. In embodiments, the functional group equivalent ratio (XH:NCO) can be at least 0.5. In some embodiments, the XH:NCO equivalent ratio can range from 0.50 to 1.3; or alternatively, from 0.75 to 1.3. In some embodiments, the XH:NCO equivalent ratio can range from 0.75 to 0.95; alternatively, from 0.95 to 1.1; or alternatively, from 1.1 to 1.3.

In an aspect, the method of making the polythiourethane further comprises curing the mixture at a temperature ranging from 0° C. to 120° C. In embodiments; the mixture may be cured at a temperature ranging from 10° C. to 30° C.; alternatively, ranging from 50° C. to 80° C.; alternatively, at ambient temperature (room temperature); alternatively, at 65° C.; or alternatively, at 120° C. In some embodiments, the mixture may be cured at ambient temperature for a time ranging from one to 8 hours; alternatively, the mixture can be cured at 65° C. for a time ranging from 10 to 18 hours; or alternatively, the mixture may be cured at 120° C. for 3 hours. In other embodiments, the mixture may be cured at about ambient temperature for a time ranging from one to 8 hours and then cured at 65° C. for a time ranging from 10 to 18 hours; alternatively, the mixture may be cured at 65° C. for a time ranging from 10 to 18 hours and then cured at 95° C. for 24 hours; or alternatively, the mixture may be cured at 120° C. for 3 hours and then cured at 95° C. for 24 hours.

In an aspect, the mixture further comprises a catalyst. In embodiments, the catalyst may be contacted with the mixture comprising the thiol ester composition and the isocyanate composition. In other embodiments, the catalyst may be combined with the thiol ester composition prior to contacting the thiol ester composition with the isocyanate composition; or alternatively, may be combined with isocyanate composition prior to contacting the isocyanate composition with the thiol ester composition.

In embodiments, the catalyst may be selected from the group consisting of a tertiary amine, an organotin compound, an amine initiated polypropylene glycol, and combinations thereof. In some embodiments the catalyst may be an amine. In other embodiments, the catalyst may be an organotin compound. In some embodiment, the catalyst may be a mixture of an amine and an organotin compound. In some embodiments, the amine catalyst may be a primary amine; alternatively, a secondary amine; or alternatively, a tertiary amine. In other embodiments amine catalyst may be aliphatic amine; or alternatively, an aromatic amine. In other embodiments, the amine catalyst may be a polyetheramine; alternatively, a polyalkylene amine; or alternatively, a tertiary amine polyol (e.g.

Jeffol® A-480). In yet other embodiments, the amine catalyst may be a polyamine comprising at least two amine groups. In some amine catalyst embodiments, the catalyst may be 1,8-diazabicyclo[5,4,0]undec-7-ene [DBU—CAS#6674-22-2]; alternatively, 1,4-diazabicyclo[2.2.2]octane [DABCO—CAS#280-57-9]); or alternatively, triethylamine. In an organotin compound catalyst embodiment, the organotin compound can be dibutyltin dilaurate.

Generally, the catalyst is utilized when the mixture comprising the thiol ester composition and the isocyanate does not cure under the desired conditions. In embodiments, the catalyst can comprise less than 10 weight percent of the mixture. In other embodiments, the catalyst comprises from 0.01% to 9.0% by weight of the mixture; alternatively, from 0.1% to 7.0% by weight of the mixture; or alternatively, from 0.5% to 3.0% by weight of the mixture.

In aspects, the polythiourethane produced by the process described herein can be further described by the properties of the polythiourethanes described herein.

Epoxy Polymer

In an aspect, the thiol ester molecules and thiol ester compositions described herein can be utilized to form an epoxy polymer. The epoxy polymers can be described as a polymer produced from thiol ester molecules (or thiol ester composition) and epoxide molecules (or epoxide composition). Generally, the thiol ester molecules (or thiol ester composition) and the epoxide molecules (or epoxide composition) are independent elements of the epoxy polymer. Therefore, the epoxy polymer can be described as an epoxy polymer produced from any combination of the thiol ester molecules (or thiol ester compositions) described herein and the epoxide molecules (or epoxide compositions) described herein. In aspects, the epoxy polymer can be linear. In other aspects, the epoxy polymer can be crosslinked. When the epoxy polymer is crosslinked, either the thiol ester molecules have greater than 2 thiol groups per thiol ester molecule or the epoxide molecules have greater than 2 epoxide groups per epoxide molecule. Alternatively, when the epoxy polymer is crosslinked, the thiol ester molecules have greater than 2 thiol groups per thiol ester molecule and the epoxide molecules have greater than 2 epoxide groups per epoxide molecule.

Generally, the thiol ester molecules have at least 2 thiol groups and the epoxide molecules have at least 2 epoxide groups. Additional embodiments regarding the number or average number of thiol groups present in the thiol ester molecules of the thiol ester composition are described herein and are generally applicable to the description of the epoxy polymer as a reaction product of a thiol ester composition and an epoxide composition. Additional embodiments regarding the number or average number of epoxide groups present in the epoxide molecules of the epoxide composition are described herein and are generally applicable to the description of the epoxy polymer as a reaction product of a thiol ester composition and an epoxide composition.

In embodiments, the thiol ester composition utilized to produce the epoxy polymer composition can comprise a hydroxy thiol ester (hydroxy thiol ester composition); or alternatively, a crosslinked thiol ester (crosslinked thiol ester composition). Additional aspects of the thiol ester molecules (e.g. average number of thiol groups per thiol ester molecule, thiol sulfur content etc. . . . ) are described herein and can be utilized to further describe the thiol ester molecules of the thiol ester compositions. Besides the thiol ester compositions described herein, other suitable thiol ester compositions will be apparent to those persons having ordinary skill in the art, can be used, and are to be considered within the scope of the present invention.

Generally the epoxide composition can comprise, singly or in any combination, any epoxide described herein. In an embodiment, the epoxide is a polyol glycidyl ether. In some embodiments, the polyol glycidyl ether may be an aliphatic polyol glycidyl ethers; alternatively, a cycloaliphatic polyol glycidyl ethers; alternatively, an aromatic glycidyl ethers; alternatively, a bisphenol glycidyl ethers; or alternatively, a novolak polyglycidyl ethers. In other embodiments, the epoxide may be a trimethylolethane triglycidyl ether; alternatively, a pentaerythritol tetraglycidyl ether; alternatively, a dipentaerythritol tetraglycidyl ether; alternatively, a sorbitol tetraglycidyl ether; alternatively, a sorbitol hexaglycidyl ether; alternatively, a bisphenol A diglycidyl ether; alternatively, a bisphenol F diglycidyl ether; alternatively, a formaldehyde-phenol novolak polyglycidyl ether; alternatively, a formaldehyde-cresol novolak polyglycidyl ether; or alternatively, a formaldehyde-catechol novolak polyglycidyl ether. Other epoxide are described herein and can generally be utilized to describe the epoxy polymers produced from the thiol ester composition and the epoxide composition. Additionally, other aspects of the epoxides (e.g. the number or average number of epoxide groups per epoxide molecule, etc.) are described herein and can be utilized to further describe the epoxide composition.

Generally, the thiol ester composition and the epoxide composition are independent elements of the epoxy polymer. Therefore, the epoxy polymer can be described as a polymer produced from any combination of the thiol ester composition described herein and the epoxide composition described herein.

In embodiments, the epoxy polymer can be described as a epoxy polymer produced by contacting any thiol ester composition comprising thiol ester molecules having at least two thiol group described herein with any epoxide composition comprising epoxide molecules having at least two epoxide groups; or alternatively, a polyol glycidyl ether composition comprising a polyol glycidyl ether having at least two epoxide groups. In some embodiments, the epoxy polymer can be described as a polymer produced by contacting the thiol ester composition with the epoxide composition comprising a bisphenol diglycidyl ether; or alternatively, a novolak polyglycidyl ether. In other embodiments, the polymer can be described as a polymer produced by contacting the thiol ester composition with the epoxide composition comprising a bisphenol A diglycidyl ether, a bisphenol F diglycidyl ether, a formaldehyde-phenol novolak polyglycidyl ether, a formaldehyde-cresol novolak polyglycidyl ether, a formaldehyde-catechol novolak polyglycidyl ether, or any combination thereof. In yet other embodiments, the epoxy polymer can be described as a polymer produced by contacting the thiol ester composition with an epoxide composition comprising a bisphenol A diglycidyl ether; alternatively, a bisphenol F diglycidyl ether; alternatively, a formaldehyde-phenol novolak polyglycidyl ether; alternatively, a formaldehyde-cresol novolak polyglycidyl ether; or alternatively, a formaldehyde-catechol novolak polyglycidyl ether.

One skilled in the art will readily recognize other possible combinations of thiol ester compositions and epoxide compositions based upon the present application.

In an aspect, the thiol ester composition and the epoxide composition are contacted at a mercaptan to epoxide molar ratio ranging from 0.8 to 1.15. In other embodiments, the thiol ester composition and the epoxide composition are contacted at a mercaptan to epoxide molar ratio ranging from 0.9 to 1.10; or alternatively, from 0.95 to 1.05. In further embodiments, the thiol ester composition and the epoxide composition are contacted at a mercaptan to epoxide molar ratio of about 1.

When the thiol ester molecules comprise a hydroxyl group both the mercaptan group and the hydroxyl group can react with the epoxide group. One of ordinary skill in the art realizes that, in this situation, both the mercaptan group and the hydroxyl group can react with the epoxide group, but generally, recognizes that the thiol group is more reactive than the hydroxyl group towards the epoxy group. Thus, the epoxy polymer can be formed by contacting the thiol ester composition and the epoxide composition in a molar ratio based upon the mercaptan to epoxide molar ratio or based upon the mercaptan plus hydroxyl to epoxide molar ratio (i.e. SH+OH: epoxide molar ratio or XH:epoxide molar ratio). In some embodiments when the thiol ester composition further comprises a hydroxyl group, the thiol ester composition and the epoxide composition are contacted at a mercaptan to epoxide molar ratio ranging from 0.8 to 1.15; alternatively, from 0.9 to 1.10; or alternatively, from 0.95 to 1.05. In other embodiments when the thiol ester composition further comprises a hydroxyl group, the thiol ester composition and the epoxide composition are contacted at a mercaptan plus hydroxyl to epoxide molar ratio ranging from 0.6 to 1.20; alternatively, from 0.8 to 1.15; alternatively, from 0.9 to 1.10; or alternatively, from 0.95 to 1.05.

In embodiments, the epoxy polymer of the present invention can be described as a epoxy polymer produced by any process described herein capable of producing the epoxy polymer and can be further described as being produced using any embodiments of the processes described herein.

The epoxy polymer has physical properties that are advantageous in many applications. For example, in embodiments, the epoxy polymer can have a glass transition temperature, Tg, ranging between −100° C. and 250° C. In some aspects, the glass transition temperature ranges from −50° C. to 200° C.; alternatively, from 0° C. to 150° C.; alternatively, from 50° C. to 100° C.; or alternatively, from −50° C. to 50° C. In some aspects, the glass transition temperature ranges from −50° C. to 0° C.; alternatively, from 0° C. to 50° C.; alternatively, from 50° C. to 100° C.; alternatively, from 100° C. to 150° C.; or alternatively, from 150° C. to 200° C.

Besides the glass transition temperature, the epoxy polymer of the present invention can have other desirable properties. For example, the epoxy polymer of the present invention can have desirable Young's modulus, tensile strength, and elongations at break, which can be measured using ASTM D638-03. In embodiments, the epoxy polymer can have a stiffness (Young's modulus) greater than 10 psi; or alternatively, ranging from 10 psi to 1,000,000 psi. In some embodiments, the epoxy polymer has a Young's modulus ranging from 600 to 300,000 psi; alternatively, from 700 to 20,000 psi; or alternatively, 20,000 to 200,000 psi. In an aspect, the epoxy polymer can have a Young's modulus ranging from 10 psi to 4,000 psi. In some embodiments, the epoxy polymer has a Young's modulus ranging from 90,000 to 600,000 psi. In embodiments, the epoxy polymer can have a tensile strength (as measured using ASTM D638-03) greater than 10 psi; or alternatively, ranging from 10 psi to 8,000 psi. In some embodiments, the epoxy polymer has a tensile strength ranging from 300 to 6,000 psi; or alternatively, from 300 to 1,000 psi. In some embodiments, the epoxy polymer can have a tensile strength ranging from 1,000 to 5,000 psi; or alternatively, ranging from 4,000 to 7,500 psi. In an aspect, the epoxy polymer can have an elongation at break (as measured using ASTM D638-03) less than 100 percent; or alternatively, greater than 100 percent. In embodiments, the epoxy polymer can have an elongation at break less than 10 percent; or alternatively, ranging from 10 percent to 100 percent. In embodiments, the epoxy polymer can have any combination of the Young's modulus, tensile strength, and elongation at break described herein.

The epoxy polymers described herein can be used in various applications. For example, the epoxy polymers can be used as adhesives or as sealants. The physical properties of the epoxy polymers can be customized to suit a particular use. As an example, if the desired application for the epoxy polymers is as a sealant, the polymer composition can be prepared so that the epoxy polymer has an elongation at break value in a desired range that makes the epoxy polymer suitable for use as a sealant.

Process of Making the Epoxy Polymer Composition

In an aspect, a method of making epoxy polymer of the present invention comprises contacting a thiol ester composition and an epoxide composition. In an embodiment, the method of producing the epoxy comprises contacting the thiol ester composition and the epoxide composition to produce a mixture and curing the mixture to produce the epoxy polymer. In some embodiments, the thiol ester composition and/or the epoxide composition contain a solvent. In other embodiments, heat is needed to cure epoxy polymer produced from the thiol ester composition and the epoxide composition. In an embodiment, including a solvent with the thiol ester composition and/or the epoxide composition lowers the temperature needed to cure the epoxy polymer or can even allow the epoxy polymer to cure at ambient temperature.

Generally, the thiol ester composition utilized to form the mixture can be any thiol ester composition described herein. In embodiments, the thiol ester composition can be a hydroxy thiol ester composition; or alternatively, a crosslinked thiol ester composition. Additional aspects of the thiol ester molecule (e.g. average number of thiol groups per thiol ester molecule, thiol sulfur content, etc. . . . ) are described herein and can be utilized to further describe the thiol ester molecules. Other suitable thiol molecules will be apparent to those persons having ordinary skill in the art, can be used, and are to be considered within the scope of the present invention.

Generally, the epoxide composition utilized to form the mixture can comprise, singly or in any combination, any epoxide described herein. In an embodiment, the epoxide is a polyol glycidyl ether. In an aspect, the polyol glycidyl ether may be aliphatic polyol glycidyl ethers; alternatively, cycloaliphatic polyol glycidyl ethers; alternatively, aromatic glycidyl ethers; alternatively, bisphenol glycidyl ethers; or alternatively, novolak glycidyl ethers. In embodiments, the epoxide may be a trimethylolethane triglycidyl ether; alternatively, a pentaerythritol tetraglycidyl ether; alternatively, a dipentaerythritol tetraglycidyl ether; alternatively, a sorbitol tetraglycidyl ether; alternatively, a sorbitol hexaglycidyl ether; alternatively, a bisphenol A diglycidyl ether; alternatively, a bisphenol F diglycidyl ether; alternatively, a formaldehyde-phenol novolak polyglycidyl ether; alternatively, a formaldehyde-cresol novolak polyglycidyl ether; or alternatively, a formaldehyde-catechol novolak polyglycidyl ether. Other epoxides are described herein and can generally be utilized to describe the epoxy polymers produced from the thiol ester composition and the epoxide composition. Additional aspects of the epoxides (e.g. number or average number of epoxide groups per epoxide molecule, etc.) are described herein and can be utilized to further describe epoxides of the epoxide compositions.

Generally, the thiol ester composition and the epoxide composition are independent elements in the method of making the epoxy polymers. Therefore, the epoxy polymer can be made by forming a mixture comprising any combination of any thiol ester composition described herein and any epoxide composition described herein.

In embodiments, the epoxy polymer can be produced by forming a mixture comprising the thiol ester composition with the epoxide composition comprising an epoxide having at least two epoxide groups; or alternatively, a polyol glycidyl ether composition comprising a polyol glycidyl ether having at least two epoxide groups. In some embodiments, the epoxy polymer can be produced by forming a mixture comprising the thiol ester composition with the epoxide composition comprising bisphenol diglycidyl ether or novolak polyglycidyl ether. In other embodiments, the epoxy polymer can be produced by forming a mixture comprising the thiol ester composition with the epoxide composition comprising bisphenol A diglycidyl ether, bisphenol F diglycidyl ether, formaldehyde-phenol novolak polyglycidyl ether, formaldehyde-cresol novolak polyglycidyl ether, formaldehyde-catechol novolak polyglycidyl ether, or any combination thereof. In yet other embodiments, the epoxy polymer can be produced by forming a mixture comprising the thiol ester composition with the epoxide composition comprising bisphenol A diglycidyl ether; alternatively, bisphenol F diglycidyl ether; alternatively, formaldehyde-phenol novolak polyglycidyl ether; alternatively, formaldehyde-cresol novolak polyglycidyl ether; or alternatively, formaldehyde-catechol novolak polyglycidyl ether.

In an aspect, the mixture further comprises a catalyst. In embodiments, the catalyst may be contacted with the mixture comprising the thiol ester composition and the epoxide composition. In other embodiments, the catalyst may be added to the thiol ester composition prior to contacting the thiol ester composition with the epoxide composition. In yet other embodiments, the catalyst may be a component of the thiol ester composition.

In some embodiments, the catalyst may be an amine. In some embodiments, the amine catalyst may be a primary amine; alternatively, a secondary amine; or alternatively, a tertiary amine. In other embodiments the amine catalyst may be aliphatic amine; or alternatively, an aromatic amine. In other embodiments, the amine catalyst may be a polyetheramine; or alternatively, a polyalkylene amine In yet other embodiments, the amine catalyst may be a polyamine comprising at least two amine groups. In some amine catalyst embodiments, the catalyst can be 1,8-diazabicyclo[5,4,0]undec-7-ene [DBU—CAS#6674-22-2]; alternatively, 1,4-diazabicyclo[2.2.2]octane [DABCO—CAS#280-57-9]); or alternatively, triethylamine. Alternatively, a phenolic catalyst can be utilized. Generally, the class of phenolic catalysts comprise materials having at least one hydroxy group attached to a carbon atom of a benzene ring. Non-limiting examples of phenolic catalysts, include phenol, resorcinol catechol, 1,4-benzenediol, resorcinol monobenzoate, and their substituted derivatives. Persons of ordinary skill in the art will readily know other suitable phenolic catalysts that can be used in the present invention.

In some applications it can be advantageous catalyze the formation of the epoxy polymer by the application of ultraviolet radiation (ultraviolet light). In an embodiment, the catalyst can be a compound that produces a Lewis acid when exposed to (irradiated with) ultraviolet radiation (light). Generally, these ultraviolet initiation catalysts comprise a catalytic-effective amount of at least one ionic salt of an organometallic complex cation selected from elements of Periodic Table Groups IVB, VB, VIIB, VIIB, and VIII. In an embodiment, the ionic salts having the formula:

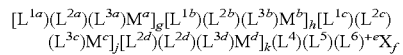

wherein $M^a$, $M^b$, $M^c$, and $M^d$ represent metal atoms that can be the same or different selected from the elements of periodic Groups IVB, VB, VIIB, VIIB, and VIII; L represents the attendant ligands; e is an integer having a value of 1, 2, or 3, which is the residual electrical charge of the complex cation; X is a halogen-containing complex anion of a metal or metalloid; f is an integer of 1 to 3 and represents the number of complex anions required to neutralize the charge e on the complex cation; and g, h, j, and k independently are 0 or 1, with at least one of them being equal to 1. The photoinitiator can be a mononuclear, binuclear, trinuclear or tetranuclear complex compound comprising the metallic atoms and the attendant ligands, L. The ligands can be any compound having an accessible unsaturated group, e.g., an ethylenic group, an acetylenic group, or an aromatic group, which have π-electrons regardless of the total molecular weight of the compound. Applicable compounds are further described in U.S. Pat. No. 5,089,536 (which is incorporated herein by reference) and the references therein. Useful compounds include, but are not limited to, cyclopentadienyl iron (II) hexafluoroantimonate, cyclopentadienyl iron (II) hexafluorophosphonate, cyclopentadienyl iron (II) hexafluoroarsenate, cumenecyclopentadienyl iron(II) hexafluorophosphate, xylenecyclopentadienyl iron(II)-tris(trifluoromethylsulfonyl) methide and the like. Other suitable types of catalysts useful in the present invention will be apparent to those of ordinary skill in the art and are to be considered within the scope of the present invention.

Generally, the catalyst is utilized when the mixture comprising the thiol ester composition and the epoxide does not cure under the desired conditions. In embodiments, the catalyst can comprise less than 10 weight percent of the mixture. In other embodiments, the catalyst comprises from 1 to 10 percent by weight of the mixture. Alternatively, when the catalyst is combined with the thiol ester composition prior to contacting the thiol ester composition with the epoxide composition, the catalyst can comprise less than 20 percent by weight of the thiol ester composition. In other embodiments, the catalyst can comprise from 1 to 20 percent by weight of the thiol ester composition. The amount of the ultraviolet initiation catalysts range generally from 0.05 to 10.0 parts by weight; alternatively, from 0.075 to 7.0 parts by weight; alternatively, from 0.1 to 4.0 parts by weight; or alternatively, from 1.0 to 2.5 parts by weight. The amount of the ultraviolet initiation catalysts range is based upon 100 parts by weight of the epoxy resin.

In an aspect, the method of making the epoxy polymer comprises curing the mixture at a temperature ranging from 0° C. to 100° C. In embodiments; the mixture is cured at a temperature ranging from 5° C. to 80° C.; alternatively, ranging from 10° C. to 60° C.; or alternatively, ranging from 10° C. to 40° C. In some embodiments, the mixture can be cured at about ambient temperature. Other suitable curing profiles are described in the Example section herein.

In an aspect, the thiol ester composition and the epoxide composition are contacted at a mercaptan to epoxide molar ratio ranging from 0.8 to 1.15. In other embodiments, the thiol ester composition and the epoxide composition are contacted at a mercaptan to epoxide molar ratio ranging from 0.9 to 1.10; or alternatively, from 0.95 to 1.05. In further embodiments, the thiol ester composition and the epoxide composition are contacted at a mercaptan to epoxide molar ratio of about 1.

When the thiol ester composition further comprises a hydroxyl group both the mercaptan group and the hydroxyl group can react with the epoxide group. One of ordinary skill in the art realizes that, in this situation, both the mercaptan group and the hydroxyl group can react with the epoxide group, but generally, recognizes that the thiol group is more reactive than the hydroxyl group towards epoxides. Thus, the epoxy polymer can be formed by contacting the thiol ester composition and the epoxide composition in a molar ratio based upon the mercaptan to epoxide molar ratio or based upon the mercaptan plus hydroxyl to epoxide molar ratio (i.e. SH+OH:epoxide molar ratio or XH:epoxide molar ratio). In some embodiments when the thiol ester composition further comprises a hydroxyl group, the thiol ester composition and the epoxide composition are contacted at a mercaptan to epoxide molar ratio ranging from 0.8 to 1.15; alternatively, from 0.9 to 1.10; or alternatively, from 0.95 to 1.05. In other embodiments when the thiol ester composition further comprises a hydroxyl group, the thiol ester composition and the epoxide composition are contacted at a mercaptan plus hydroxyl to epoxide molar ratio ranging from 0.6 to 1.20; alternatively, from 0.8 to 1.15; alternatively, from 0.9 to 1.10; or alternatively, from 0.95 to 1.05.

Generally, the solvent is utilized when the mixture comprising the thiol ester composition and the epoxide does not cure under the desired conditions. In embodiments, the solvent has similar polarity and viscosity properties to those of the thiol ester compositions. In an aspect, the solvents have relatively low vapor pressures. In some embodiments, the solvents have vapor pressures greater than 1 mm Hg at 20° C. In some embodiments, the solvent is selected from the group consisting of alcohols, esters, ethers, ketones, aromatic hydrocarbons, hydrocarbons, and combinations thereof. In an embodiment the solvent is an alcohol; alternatively, an ester; alternatively, an ether; alternatively, an aromatic hydrocarbon; or alternatively, a hydrocarbon. The alcohol solvent can be any alcohol having a vapor pressure greater than 1 mm Hg at 20° C., such as methanol, ethanol, 1-propanol, 2-propanol (isopropanol), 1-butanol, 2-butanol, 2-methyl-1-propanol (isobutyl alcohol), 2-methyl-2-proanol (tert-butanol), 1-pentanol, 2-pentanol, or combinations thereof. The ester solvent can be any ester having a vapor pressure greater than 1 mm Hg at 20° C., such as methyl acetate, ethyl acetate, n-propyl acetate, isopropyl acetate, n-butyl acetate, or combinations thereof. The ether solvent can be any ether having a vapor pressures greater than 1 mm Hg at 20° C., such as dimethyl ether, methyl ethyl ether, diethyl ether, diisopropyl ether, dibutyl ether, or combinations thereof. The ketone solvent can be any ketone having a vapor pressures greater than 1 mm Hg at 20° C., such as acetone, 2-butanone (methyl ethyl ketone), 3-methyl-2-butanone, 2-pentanone, 3-pentanone, 4-methyl-2-pentanone (methyl isobutyl ketone), or combinations thereof. The aromatic solvent can be any aromatic hydrocarbon having a vapor pressures greater than 1 mm Hg at 20° C., such as toluene, xylene (ortho, meta, para or mixtures thereof), or combinations thereof. The hydrocarbon solvent can be any hydrocarbon having a vapor pressure greater than 1 mm Hg at 20° C., such as pentane, hexane(s), cyclohexane, heptane(s), octane, or combinations thereof. In some embodiments, the solvent can contain two or more functional groups, e.g. butoxy ethanol, diacetone alcohol, or cellosolve acetate, among others. In an aspect, the solvent can be n-butanol, butoxy ethanol, diacetone alcohol, or combinations thereof. In some embodiments, the solvent is selected from the group consisting of n-butanol, n-butyl acetate, xylene, MIBK (methyl isobutyl ketone), acetone, n-butyl acetate, butoxy ethanol, diacetone alcohol, MIBK/toluene, cellosolve acetate, and combinations thereof. Other suitable solvents will be apparent to those of skill in the art and are to be considered within the scope of the present invention.

Feedstocks

Unsaturated Ester Composition Comprising Unsaturated Ester Having Internal Carbon-Carbon Double Bonds The unsaturated ester molecules having internal carbon-carbon double bonds may be described using a number of different methods. For example, the unsaturated ester having internal carbon-carbon double bonds may be described by the number of ester groups and the number of internal carbon-carbon double bonds that are in each unsaturated ester molecule. Suitable unsaturated esters having internal carbon-carbon double bonds may include at least one internal carbon-carbon double bond. However, the number of ester groups and internal carbon-carbon double bonds contained within the unsaturated esters are independent elements and may be varied independently of each other. Thus, the unsaturated esters having internal carbon-carbon double bonds may have any combination of the number of ester groups and the number of internal carbon-carbon double bonds as described separately herein. Suitable unsaturated esters may also contain additional functional groups such as hydroxyl, aldehyde, ketone, epoxy, ether, aromatic groups, and combinations thereof. For example, the castor oil has hydroxyl groups in addition to internal carbon-carbon double bonds and ester groups. Alternatively, the unsaturated ester having internal carbon-carbon double bonds may be substantially devoid of functional groups other than the ester groups and the internal carbon-carbon double bonds. Other suitable unsaturated esters will be apparent to those of skill in the art and are to be considered within the scope of the present techniques.

The unsaturated ester molecules having internal carbon-carbon double bonds may have more have at least 2 ester groups, 3 ester groups or 4 ester groups. In some embodiments, Further, the unsaturated ester molecules may have from 2 to 8 ester groups, from 2 to 7 ester groups or from 3 to 5 ester groups. In embodiments, the unsaturated ester may include from 3 to 4 ester groups.

The unsaturated ester having internal carbon-carbon double bonds may be a mixture of unsaturated ester molecules having internal carbon-carbon double bonds. In this situation, the number of ester groups is best described as an average number of ester groups per unsaturated ester molecule. In an embodiment, the unsaturated esters having internal carbon-carbon double bonds may have an average of at least 2 ester groups per unsaturated ester molecule; alternatively, an average of at least 2.5 ester groups per unsaturated ester molecule; or alternatively an average of at least 3 ester groups per unsaturated ester molecule. In some embodiments, the unsaturated esters having internal carbon-carbon double bonds may have an average of from 1.5 to 8 ester groups per unsaturated ester molecule; alternatively, an average of from 2 to 7 ester groups per unsaturated ester molecule alternatively, an average of from 2.5 to 5 ester groups per unsaturated ester molecule; or alternatively, an average of from 3 to 4 ester groups per unsaturated ester molecule. In embodiments, the unsaturated esters having internal carbon-carbon double bonds may have an average of about 3 ester groups per unsaturated ester molecule; or alternatively an average of about 4 ester groups per unsaturated ester molecule.

The unsaturated esters having internal carbon-carbon double bonds have at least 2 internal carbon-carbon double bonds; alternatively, at least 3 internal carbon-carbon double bonds; or alternatively, at least 4 internal carbon-carbon double bonds. Further, the unsaturated ester having internal carbon-carbon double bonds may have 2 to 9 internal carbon-carbon double bonds; alternatively, 2 to 4 internal carbon-carbon double bonds; alternatively, 3 to 8 internal carbon-carbon double bonds; or alternatively, 4 to 8 internal carbon-carbon double bonds.

The unsaturated ester molecules having internal carbon-carbon double bonds may be a mixture of unsaturated ester molecules having internal carbon-carbon double bonds. In this situation, the number of internal carbon-carbon double bonds is best described as an average number of ester groups per unsaturated ester molecule. In an embodiment, the unsaturated esters having internal carbon-carbon double bonds may have an average of at least of at least 2 internal carbon-carbon double bonds per unsaturated ester molecule; alternatively, an average of at least 2.5 internal carbon-carbon double bonds per unsaturated ester molecule; or alternatively, an average of at least 3 internal carbon-carbon double bonds per unsaturated ester molecule. In some embodiments, the unsaturated esters having internal carbon-carbon double bonds may have average of from 1.5 to 9 internal carbon-carbon double bonds per unsaturated ester molecule; alternatively, an average of from 3 to 8 internal carbon-carbon double bonds per unsaturated ester molecule; alternatively, an average of from 2 to 4 internal carbon-carbon double bonds per unsaturated ester molecule; or alternatively, an average of from 4 to 8 internal carbon-carbon double bonds per unsaturated ester molecule.

In addition to the number of ester groups and the number of non-terminal alkene groups present in the unsaturated ester molecules, the disposition of the non-terminal alkene groups in unsaturated ester molecules having 2 or more non-terminal alkene groups may be a consideration. For example, where the unsaturated ester molecules having internal carbon-carbon double bonds have 2 or more internal carbon-carbon double bonds, the non-terminal alkene groups may be adjacent and, thus, conjugated. In another example, the internal carbon-carbon double bonds may be separated from each other by only one carbon atom. When two internal carbon-carbon double bonds are separated by a carbon atom having two hydrogen atoms attached to it, e.g. a methylene group, these internal carbon-carbon double bonds may be termed as methylene interrupted double bonds. In other molecules, the internal carbon-carbon double bonds alkene groups may isolated, e.g. the internal carbon-carbon double bonds are separated from each other by 2 or more carbon atoms. Finally, the non-terminal alkene groups may be conjugated with a carbonyl group.

Alternatively, the unsaturated ester molecules having internal carbon-carbon double bonds of the unsaturated ester composition may be described as having ester linkages comprising a residue of a polyol and a carboxylic acid residues having an internal carbon-carbon double bond. Additional features of the residue of the polyol and the carboxylic acid residues having an internal carbon-carbon double bond are independently described herein and may be utilized in any combination to describe the unsaturated ester molecules having ester linkages comprising a residue of a polyol and a carboxylic acid residues having an internal carbon-carbon double bond.

It will be appreciated that the unsaturated esters having ester linkages comprising a residue of a polyol and carboxylic acid residues having an internal carbon-carbon double bond may be a mixture of many different compounds. Consequently, particular features of the unsaturated esters having ester linkages comprising a residue of a polyol and carboxylic acid residues having an internal carbon-carbon double bond may be described as an average per unsaturated ester molecule.

The residue of the polyol and the carboxylic acid residue having an internal carbon-carbon double bond are independent elements of unsaturated ester molecules having ester linkages comprising a residue of a polyol and carboxylic acid residues having an internal carbon-carbon double bond. Consequently, the features of the residue of the polyol and the carboxylic acid having an internal carbon-carbon double bond are independently described herein and may be used in any combination to describe the unsaturated ester molecules having ester linkages comprising a residue of a polyol and carboxylic acid residues having an internal carbon-carbon double bond.

The carboxylic acid residue having an internal carbon-carbon double bond may be further described by its structural features. These structural features are independently described herein and may be utilized in any combination to describe the carboxylic acid residue having an internal carbon-carbon double bond.

In an embodiment, the carboxylic acid residue having an one carbon-carbon double bond may have one, two, three, or more internal carbon-carbon double bonds; alternatively, only one internal carbon-carbon double bonds; alternatively, only two internal carbon-carbon double bonds; or alternatively, only three internal carbon-carbon double bonds. In will be appreciated, that since the unsaturated ester molecules comprise multiple carboxylic acid residues having internal carbon-carbon double bonds, the unsaturated ester molecules having internal carbon-carbon double bonds may contain some of carboxylic acid residues having different number of internal carbon-carbon double bonds. For example, an unsaturated ester composition comprising unsaturated ester molecules having ester linkages comprising a residue of a triol (e.g. glycerol or trimethylol propane) and three carboxylic acid residues having an internal carbon-carbon double bonds may have one carboxylic acid residue having only one internal carbon-carbon double bonds, one carboxylic acid residue having only two internal carbon-carbon double bonds, and one carboxylic acid residue having only three internal carbon-carbon double bonds.

In an embodiment, each internal carbon-carbon double bond of the carboxylic acid residue having an internal carbon-carbon double bond is a di-substituted internal carbon-carbon double bond. In some embodiments, the internal carbon-carbon double bond closest to the carbonyl group of the carboxylic acid residue having an internal carbon-carbon double bond is a di-substituted internal carbon-carbon double bond. In an embodiment, the carboxylic acid residue having an internal carbon-carbon double bond is linear. In another embodiment, the carboxylic acid residue having an internal carbon-carbon double bond is linear is branched.

In an embodiment, the carboxylic acid residue having an internal carbon-carbon double bond may have at least 4 carbon atoms; alternatively, at least 6 carbon atoms; or alternatively, at least 8 carbon atoms. In some embodiments, the carboxylic acid residue having at least one internal carbon-carbon double bond may have from 4 to 20 carbon atoms; alternatively, from 6 to 18 carbon atoms; alternatively, from 8 to 14 carbon atoms; alternatively, from 10 to 11 carbon atoms; alternatively, only 10 carbon atoms; or alternatively, only 11 carbon atoms. In some embodiments, the carboxylic acid equivalent having an internal carbon-carbon double bond may be a mixture of carboxylic acid residues having an internal carbon-carbon double bond. In such embodiments, the carboxylic acid residues having an internal carbon-carbon double bond may have an average of at least 6 carbon atoms; or alternatively, at least 8 carbon atoms; alternatively, alternatively, from 6 to 18 carbon atoms; alternatively, from 8 to 14 carbon atoms; alternatively, from 10 to 11 carbon atoms; alternatively, about 10 carbon atoms; or alternatively, about 11 carbon atoms.

In further embodiments, the carboxylic acid residue having an internal carbon-carbon double bond can further comprise a hydroxyl group. In some embodiments, the carbon atom bearing the hydroxyl group is separated from the internal carbon-carbon double bond by a methylene group (—$CH_2$—). In other embodiments, the carboxylic acid residue having at least one internal carbon-carbon double bond is devoid of other functional groups.

The residue of the polyol may be further described by its structural features. These structural features are independently described herein and may be utilized in any combination to describe the residue of the polyol of the unsaturated ester molecules having ester linkages comprising, or consisting essentially of a residue of a polyol and carboxylic acid residues having an one internal carbon-carbon double bond.

In an embodiment, residue of the polyol may have 2 to 20 carbon atoms. In some embodiments, the residue of the polyol may have 2 to 12 carbon atoms; alternatively, 2 to 8 carbon atoms; or alternatively, 2 to 5 carbon atoms. In other embodiments, the residue of the polyol may be a residue of a mixture of polyols. In such an instance, the residue of the polyol may have an average of 2 to 20 carbon atoms per polyol residue; alternatively, an average of 2 to 12 carbon atoms per polyol residue; alternatively, an average of 2 to 8 carbon atoms per polyol residue; or alternatively, an average of 2 to 5 carbon atoms per polyol residue.

In some embodiment, the residue of the polyol may have had 2 to 8 hydroxyl group; alternatively, 3 to 6 hydroxyl groups; alternatively, 2 to 4 hydroxyl groups; alternatively, 4 to 8 hydroxyl groups; alternatively, only 2 hydroxyl groups; alternatively, only 3 hydroxyl groups; alternatively, only 4 hydroxyl groups; alternatively, only 5 hydroxyl groups; or alternatively, only 6 hydroxyl groups. In other embodiments, the residue of the polyol may be a residue of a mixture of polyols. In such an instance, the residue of the polyol may have an average of 2 to 20 carbon atoms per polyol molecule; alternatively, an average of 2 to 12 carbon atoms per polyol molecule; alternatively, an average of 2 to 8 carbon atoms per polyol molecule; or alternatively, an average of 2 to 5 carbon atoms per polyol molecule. Further, the residues of the polyols may have had an average of at least 2.5 hydroxyl groups per polyol molecule; alternatively, 2.5 to 8 hydroxyl groups per polyol molecule; alternatively, an average of 2 to 6 hydroxyl groups per polyol molecule; alternatively, an average of 2.5 to 5 hydroxyl groups per polyol molecule; alternatively, an average of 2.5 to 4.5 hydroxyl group per polyol molecule; alternatively, an average of 2.5 to 3.5 hydroxyl group per polyol molecule; alternatively, an average of 3 to 4 hydroxyl group per polyol molecule; alternatively, an average of about 3 hydroxyl groups per polyol molecule; alternatively, an average of about 4 hydroxyl groups per polyol molecule; alternatively, an average of about 5 hydroxyl groups per polyol molecule; or alternatively an average of about 6 hydroxy groups per polyol molecule.

In an embodiment, the polyol or mixture of polyols used to produce the unsaturated esters compositions comprising or consisting essentially of, unsaturated esters having a terminal carbon-carbon double bonds has a molecular weight or average molecular weight less than 300. In other embodiments, the polyol or mixture of polyols have a molecular weight or average molecular weight less than 250; alternatively less than 200; alternatively, less than 150; or alternatively, less than 100.

In an embodiment, the polyol that formed the residue of the polyol is a diol, triol, a tetraol, pentaol, hexaol, or combination thereof; alternatively a diol, triol, tetraol or combination thereof; or alternatively, a triol, tetraol or combination thereof. In some embodiments, the polyol that formed the residue of the polyol is a diol; alternatively, a triol; alternatively, a tetraol; alternatively, a pentaol; or alternatively, a hexaol. Suitable polyols that may form the residue of the polyol include ethane diol, propanediol, butanediol, pentanediol, hexanediol, cyclohexane diol, phenylethane diol, cyclohexanedimethanol, dimethylolpropane, benzenedimethanol, cyclohexanetriol, trihydroxybenzene, trimethylolethane, trimethylolpropane, trimethylolbutane, glycerol, pentaerythritol, sorbitol, or any combination thereof; alternatively, cyclohexane diol, trimethylol propane, glycerol, pentaerythritol, or combinations thereof; alternatively, glycerol, pentaerythritol, or combinations thereof. In some embodiments, the polyol that may form the residue of the polyol include 1,2-ethanediol, 1,3-propanediol, 1,4-butanediol, 1,5-pentanediol, 1,6-hexanediol, dimethylolpropane, neopentyl glycol, 2-propyl-2-ethyl-1,3-propanediol, 1,2-propanediol, 1,2-butanediol, 1,3-butanediol, 1,4-butanediol, diethylene glycol, triethylene glycol, polyethylene glycol, dipropylene glycol, tripropylene glycol, polypropylene glycol, 1,1-cyclohexanedimethanol, 1,2-cyclohexanedimethanol, 1,3-cyclohexanedimethanol, 1,4-cyclohexanedimethanol, 1,3-dioxane-5,5-dimethanol, 1-phenyl-1,2-ethanediol, trimethylolpropane, trimethylolethane, trimethylolbutane, glycerol, 1,2,5-hexanetriol, pentaerythritol, ditrimethylolpropane, diglycerol, ditrimethylolethane, 1,3,5-trihydroxybenzene, 1,2-benzenedimethanol, 1,3-benzenedimethanol, 1,4-benzenedimethanol, 1-phenyl-1,2-ethanediol, sorbitol, or any combination thereof. In other embodiments, the polyol that may be used as the polyol residue may be trimethylolpropane, glycerol, pentaerythritol, or combinations thereof; alternatively, trimethylolpropane; alternatively, glycerol; alternatively, pentaerythritol; or alternatively sorbitol.

It should be appreciated that not all of the hydroxyl groups of the polyol that form the residue of the polyol of the thiol ester molecule having ester linkages must form ester linkages. In some instances some of the hydroxyl groups may not form ester linkages and may remain as hydroxyl group. In an embodiment, the thiol ester molecules having ester linkages that may comprise a residue of a polyol and carboxylic acid residues having a thiol group are substantially devoid of hydroxy groups derived from the polyol. In other embodiments, substantially, all of the hydroxyl groups of the polyol that forms the residue of a polyol form linkages with a carboxylic acid having internal carbon-carbon double bonds.

It will be appreciated that not all of the ester linkages comprising the residue of the polyol may comprise carboxylic acid residues having an internal carbon-carbon double bond. For example, some of the ester linkages may comprise a residue of the polyol and saturated carboxylic acid group. In such an instance, the unsaturated ester molecules having ester linkages comprising a residue of a polyol and carboxylic acid residues having an internal carbon-carbon double bond may be further defined by the average ratio of carboxylic acid residues having an internal carbon-carbon double bond to saturated carboxylic acid residues. In an embodiment, average ratio of carboxylic acid residues having an internal carbon-carbon double bond to saturated carboxylic acid residues may be greater than 5:1; alternatively, less than 7:1; or alternatively, less than 10:1. In other embodiments, the unsaturated ester molecules having ester linkages comprising any residue of a polyol described herein and any carboxylic acid residue having an internal carbon-carbon double bond described herein may have an average of greater than 75, 80, 85, or 90 percent of hydroxyl units of the polyol forming the residue of the polyol residue having an ester linkage with any carboxylic acid having an internal carbon-carbon double bond described herein.

In an embodiment, the unsaturated ester molecules, whether described as having particular functional groups or as unsaturated ester molecules having ester linkages comprising a residue of a polyol and a carboxylic acid residues having an internal carbon-carbon double bond, may have an average ratio of carboxylic acid residues having an internal carbon-carbon double bond to ester groups in the thiol ester molecules less than 1.15:1; alternatively, less than 1.1:1; or alternatively, less than 1.05:1. In some embodiments, the unsaturated ester molecules, whether described as having particular functional groups or as unsaturated ester molecules having ester linkages comprising a residue of a polyol and a carboxylic acid residues having an internal carbon-carbon double bond, may have an average ratio carboxylic acid residues having an internal carbon-carbon double bond to ester groups in the thiol ester molecules ranges from 0.75:1 to 1.15:1; alternatively, ranges from 0.85:1 to 1.1:1; or alternatively, ranges from 0.90:1 to 1.05:1. In other embodiments, the unsaturated ester molecules, whether described as having particular functional groups or as unsaturated ester molecules having ester linkages comprising a residue of a polyol and a carboxylic acid residues having an internal carbon-carbon double bond, may have an average ratio of carboxylic acid residues having an internal carbon-carbon double bond to ester groups in the thiol ester molecules of about 1:1.

Unsaturated Natural Source Oil

In an aspect, the unsaturated ester having internal carbon-carbon double bonds may be an unsaturated natural source oil. For example, the unsaturated natural source oil may be tallow, olive, peanut, castor bean, sunflower, sesame, poppy, seed, palm, almond seed, hazelnut, rapeseed, soybean, corn, safflower, canola, cottonseed, camelina, flaxseed, or walnut oil. From these choices, any one or any combinations of unsaturated natural source oils may be selected on the basis of the desired properties, cost or supply. For example, the natural source oil may be selected from the group consisting of soybean, rapeseed, canola, or corn oil. Castor bean oil may be selected due to a large available supply in some parts of the world. Soybean oil may be selected due to a low cost and/or abundant supply. Finally, other oils may be selected to provide appropriate properties in the final composition. In some embodiments, the unsaturated natural source oil may be soybean, corn, castor bean, safflower, canola, cottonseed, camelina, flaxseed, or walnut oil. In other embodiments, the unsaturated natural source oil may be, soybean oil, corn oil, canola oil, or castor bean oil. In further embodiments, the unsaturated natural source oil can be soybean oil; alternatively corn oil; alternatively castor bean oil; or alternatively, canola oil. For example, from the choices listed above, certain unsaturated natural source oils may be selected to minimize the number of methylene interrupted double bonds, which may result in greater amounts of undesirable side products. For, example some genetically modified soybeans may comprise triglycerides having reduced quantities of chain groups having methylene interrupted double bonds (e.g. a linoleic group) and or saturated chain groups. The unsaturated natural source oil may be a triglyceride derived from either naturally occurring or genetically modified nut, vegetable, plant, or animal sources.

Isocyanates and Isocyanate Compositions

Generally, the isocyanate composition comprises an isocyanate having at least one isocyanate group. In an embodiment, the isocyanate composition is comprised of isocyanates having multiple isocyanate groups. In some embodiments, the isocyanate has at least two isocyanate groups; alternatively, at least three isocyanate groups; or alternatively, at least 4 isocyanate groups. In other embodiments, the isocyanate has from 2 to 8 isocyanate groups; alternatively, from 2 to 6; alternatively from 2 to 4 isocyanate groups. In yet other embodiments, the isocyanate has only 2 isocyanate groups; alternatively, only 3 isocyanate groups; or alternatively, only 4 isocyanate groups. In an aspect, the isocyanate composition comprises a mixture of isocyanates. When the isocyanate composition comprises a mixture of isocyanates, the isocyanates can have an average of at least 1.5 isocyanate groups per isocyanate molecule; alternatively, an average of at least 2 isocyanate groups per isocyanate molecule; alternatively, an average of at least 2.5 isocyanate groups per isocyanate molecule; or alternatively, an average of at least 3 isocyanate groups per isocyanate molecule. In embodiments, the isocyanates can have an average of from 1.5 to 12 isocyanate groups per isocyanate molecule; alternatively, an average of from 1.5 to 9 isocyanate groups per isocyanate molecule; alternatively, an average of from 2 to 7 isocyanate groups per isocyanate molecule; alternatively, an average of from 2 to 5 isocyanate groups per isocyanate molecule; or alternatively, an average of from 2 to 4 isocyanate groups per isocyanate molecule.

In an embodiment, the isocyanate composition can comprise aliphatic isocyanates, cycloaliphatic isocyanates, aromatic isocyanates, or any combination thereof. In some embodiments, the isocyanate composition comprises aliphatic isocyanates; alternatively, cycloaliphatic isocyanates; or alternatively, aromatic isocyanates.

In an embodiment, the aliphatic isocyanates of the isocyanate composition can comprise ethylene diisocyanate, 1,3-trimethylene diisocyanate, 1,4-tetramethylene diisocyanate, 1,6-hexamethylene diisocyanate, 1,7-heptamethylene isocyanate, 1,8-octamethylene diisocyanate, 1,9-nonamethylene diisocyanate, 1,10-decamethylene diisocyanate, 1,11-undecamethylene diisocyanate, 1,12-dodeca-methylene diisocyanate, 2,2'-dimethylpentane diisocyanate, 2,2,4-trimethyl-1,6-hexamethylene diisocyanate, 2,4,4-trimethylhexamethylene diisocyanate, 1,6,11-undecane triisocyanate, 1,3,6-hexa-methylene triisocyanate, 1,8-diisocyanato-4-(isocyanatomethyl)octane, 2,5,7-trimethyl-1,8-diisocyanato-5-(isocyanatomethyl)octane, or any combination thereof. In some embodiments, the aliphatic isocyanates of the isocyanate composition can comprise ethylene diisocyanate, 1,3-trimethylene diisocyanate, 1,4-tetramethylene diisocyanate, 1,6-hexamethylene diisocyanate, 1,12-dodecamethylene diisocyanate, 2,2,4-trimethyl-1,6-hexamethylene diisocyanate, 2,4,4-trimethylhexamethylene diisocyanate, 1,6,11-undecane triisocyanate, 1,3,6-hexamethylene triisocyanate, or any combination thereof. In other embodiments, the aliphatic isocyanates of the isocyanate composition can comprise 1,4-tetra-methylene diisocyanate, 1,6-hexamethylene, or any combination thereof. In yet other embodiments, the aliphatic isocyanate of the isocyanate composition comprises 1,6-hexa-methylene.

In embodiments, the cycloaliphatic isocyanates of the isocyanate composition can comprise 1-isocyanato-2-isocyanatomethyl cyclopentane, 1,3-cyclohexane diisocyanate, 1,4-cyclohexane diisocyanate, 2,4-methylcyclohexane diisocyanate, 2,6-methylcyclohexane diisocyanate, 1,2-dimethylcyclohexane diisocyanate, 1,4-dimethylcyclohexane diisocyanate, isophorone diisocyanate (IPDI), 1-isocyanato-1-methyl-4(3)-isocyanatomethyl cyclohexane, 1,3-bis-(isocyanato-methyl) cyclohexane, 1,4-bis(isocyanatomethyl)cyclohexane, 2,4'-dicyclohexylmethane diisocyanate, 4,4'-dicyclohexylmethane diisocyanate (hydrogenated MDI, HMDI), 2,2'-dimethyldicyclohexylmethane diisocyanate, 4,4'-bis(3-methylcyclohexyl)methane diisocyanate, or any combination thereof. In some embodiments, the cyclic aliphatic isocyanates of the isocyanate composition can comprise 1,3-cyclohexane diisocyanate, 1,4-cyclohexane diisocyanate, 2,4-methylcyclohexane diisocyanate, 2,6-methylcyclohexane diisocyanate, 1,2-dimethylcyclohexane diisocyanate, 1,4-dimethylcyclohexane diisocyanate, isophorone diisocyanate, 2,4'-dicyclohexylmethane diisocyanate, 4,4'-dicyclohexylmethane diisocyanate, or any combination thereof. In other embodiments, the cyclic aliphatic isocyanate of the isocyanate composition comprises 1,3-cyclohexane diisocyanate; alternatively, 1,4-cyclohexane diisocyanate; alternatively, 2,4-methylcyclohexane diisocyanate; alternatively, 2,6-methylcyclohexane diisocyanate; alternatively, isophorone diisocyanate; alternatively, 2,4'-dicyclohexylmethane diisocyanate; or alternatively, 4,4'-dicyclohexylmethane diisocyanate.

In embodiments, the aromatic isocyanates of the isocyanate composition can comprise 1,3-phenylene diisocyanate, 1,4-phenylene diisocyanate, 2,4-tolylene diisocyanate (TDI), 2,5-toluene diisocyanate 2,6-tolylene diisocyanate, tolylene-α,4-diisocyante, 1,3-xylylene diisocyanate, 1,4-xylylene diisocyanate, diethylphenylene diisocyanate, diisopropylphenylene diisocyanate, trimethylbenzene triisocyanate, α,α,α',α'-tetramethyl-1,3-xylylene diisocyanate, α,α,α',α'-tetramethyl-1,4-xylylene diisocyanate, mesitylene triisocyanate, benzene triisocyanate, 1,5-diisocyanato naphthalene, methylnaphthalene diisocyanate, bis(isocyanatomethyl) naphthalene, biphenyl diisocyanate, 2,4'-diphenylmethane diisocyanate, 4,4'-diphenylmethane diisocyanate (MDI), polymeric 4,4'-diphenyl-methane diisocyanate (polymeric MDI, PMDI), 3,3'-dimethyl-diphenylmethane-4,4'-diisocyanate, bibenzyl-4,4'-diisocyanate, bis(isocyanatophenyl)ethylene, triphenylmethane triisocyanate, bis(isocyanatoethyl) benzene, bis-(isocyanatopropyl)benzene, bis(isocyanatobutyl) benzene, naphthalene triisocyanate, diphenylmethane-2,4,4'-triisocyanate, 3-methyldiphenylmethane-4,6,4'-triisocyanate, 4-methyldiphenyl-methane-3,5,2',4',6'-pentaisocyanate, tetrahydronaphthylene diisocyanate, or any combination thereof. In some embodiments, the aromatic isocyanates of the isocyanate composition can comprise 1,3-phenylene diisocyanate, 1,4-phenylene diisocyanate, 2,4-tolylene diisocyanate, 2,6-tolylene diisocyanate, 1,3-xylylene diisocyanate, 1,4-xylylene diisocyanate, trimethylbenzene triisocyanate, benzene triisocyanate, biphenyl diisocyanate, 2,4'-diphenylmethane diisocyanate, 4,4'-diphenylmethane diisocyanate, polymeric 4,4'-diphenylmethane diisocyanate, 3,3'-dimethyl-diphenylmethane-4,4'-diisocyanate, bibenzyl-4,4'-diisocyanate, triphenylmethane triisocyanate, polymeric MDI, naphthalene triisocyanate, or any combination thereof. In other embodiments, the aliphatic isocyanates of the isocyanate composition comprises 1,3-phenylene diisocyanate, 1,4-phenylene diisocyanate, 2,4-tolylene diisocyanate, 2,6-tolylene diisocyanate, 1,3-xylylene diisocyanate, 1,4-xylylene diisocyanate, 2,4'-diphenylmethane diisocyanate, 4,4'-diphenylmethane diisocyanate, polymeric 4,4'-diphenylmethane diisocyanate, 3,3'-dimethyl-diphenylmethane-4,4'-diisocyanate, polymeric 4,4'-diphenylmethane diisocyanate, or any combination thereof. In yet other embodiments, the aliphatic isocyanates of the isocyanate composition comprises 2,4-tolylene diisocyanate; alternatively, 2,6-tolylene diisocyanate; alternatively, 2,4- and 2,6-tolylene diisocyanate; alternatively, 4,4'-diphenylmethane diisocyanate; alternatively, polymeric 4,4'-diphenylmethane diisocyanate; or alternatively, mixtures of 2,4'-diphenylmethane diisocyanate and 4,4'-diphenylmethane diisocyanate.

Epoxide Compositions

Generally, the epoxide composition comprises an epoxide having at least 1 epoxide group. In an embodiment, the epoxide composition can comprise an epoxide having at least 2 epoxide groups; alternatively, at least three epoxide groups. In some embodiments, the epoxide composition comprises a mixture of epoxide molecules. When the epoxide composition comprises a mixture of epoxide molecules, the epoxide molecules can have an average of at least 1.5 epoxide groups per epoxide molecule; alternatively, an average of at least 2 epoxide groups per epoxide molecule; alternatively, an average of at least 2.5 epoxide groups per epoxide molecule; or alternatively, an average of at least 3 epoxide groups per epoxide molecule. In other embodiments, the epoxide molecules can have an average of from 1.5 to 16 epoxide groups per epoxide molecule; alternatively, an average of from 1.5 to 12 epoxide groups per epoxide molecule; alternatively, an average of from 1.5 to 9 epoxide groups per epoxide molecule; alternatively, an average of from 2 to 7 epoxide groups per epoxide molecule; alternatively, an average of from 2 to 5 epoxide groups per epoxide molecule; or alternatively, an average of from 2 to 4 epoxide groups per epoxide molecule.

Generally, the epoxide may be comprised of molecules having multiple groups having structure E1:

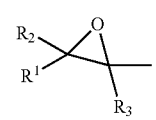

E1 where each $R^1$, $R^2$, and $R^3$ can be H, an organyl group, or a hydrocarbyl group and the undesignated valency represents the remainder of the structure of the epoxide molecule. In embodiments, each $R^1$, $R^2$, and $R^3$ can be H or a $C_1$ to $C_{20}$ organyl group; alternatively, H or a $C_1$ to $C_{10}$ organyl group; or alternatively, H or a $C_1$ to $C_5$ organyl group. In other embodiments, each R', $R^2$, and $R^3$ can be H or a $C_1$ to $C_{20}$ hydrocarbyl group; alternatively, H or a $C_1$ to $C_{10}$ hydrocarbyl group; or alternatively, H or a $C_1$ to $C_5$ hydrocarbyl group. In yet other embodiments, R', $R^2$, and $R^3$ are H, or $R^1$ and $R^2$ are H and $R^3$ is a methyl group, or a combination thereof. In yet other embodiments, R', $R^2$, and $R^3$ are H; or alternatively, $R^1$ and $R^2$ are H and $R^3$ is a methyl group. When an epoxide molecule comprises two or more E1 groups, the additional E1 can be located within $R^1$, $R^2$, $R^3$ or the undesignated epoxide valency. In an embodiment when the epoxide molecule comprises two or more E2 groups, R', $R^2$, and $R^3$ can be any group described herein and the additional E2 group(s) are located in the undesignated epoxide valency.

In embodiments, the epoxide composition comprises an epoxide having at least 2 epoxide groups having structure E1. In embodiments, the epoxide composition can comprise an epoxide having at least 3 epoxide groups having structure E1. In some embodiments, the epoxide composition comprises a mixture of epoxide molecules having structure E1. When the epoxide composition comprises a mixture of epoxide molecules, the epoxide molecules can have an average of at least 1.5 epoxide groups having structure E1 per epoxide molecule; alternatively, an average of at least 2 epoxide groups having structure E1 per epoxide molecule; alternatively, an average of at least 2.5 epoxide groups having structure E1 per epoxide molecule; or alternatively, an average of at least 3 epoxide groups having structure E1 per epoxide molecule. In embodiments, the epoxide molecules can have an average of from 1.5 to 16 epoxide groups having structure E1 per epoxide molecule; alternatively, an average of from 1.5 to 12 epoxide groups having structure E1 per epoxide molecule; alternatively, an average of from 1.5 to 9 epoxide groups having structure E1 per epoxide molecule; alternatively, an average of from 2 to 7 epoxide groups having structure E1 per epoxide molecule; alternatively, an average of from 2 to 5 epoxide groups having structure E1 per epoxide molecule; or alternatively, an average of from 2 to 4 epoxide groups having structure E1 per epoxide molecule.

A class of epoxides that can be utilized in the epoxide composition is a polyol glycidylether. Generally, the polyol glycidylether composition may be comprised of molecules having multiple glycidylether groups having structure E2:

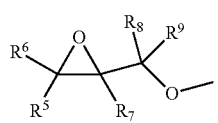

E2 where each $R^5$, $R^6$, $R^7$, $R^8$, and $R^9$ can be H, an organyl group, or a hydrocarbyl group and the undesignated valency represents the remainder of the structure of the polyol glycidylether molecule. In embodiments, each $R^5$, $R^6$, $R^7$, $R^8$, and $R^9$ can be H or a $C_1$ to $C_{20}$ organyl group; alternatively, H or a $C_1$ to $C_{10}$ organyl group; or alternatively, H or a $C_1$ to $C_5$ organyl group. In other embodiments, each $R^5$, $R^6$, $R^7$, $R^8$, and $R^9$ can be H or a $C_1$ to $C_{20}$ hydrocarbyl group; alternatively, H or a $C_1$ to $C_{10}$ hydrocarbyl group; or alternatively, H or a $C_1$ to $C_5$ hydrocarbyl group. In yet other embodiments, $R^5$, $R^6$, $R^8$, and $R^9$ are H and $R^7$ is a methyl group; or alternatively, $R^5$, $R^6$, $R^7$, $R^8$, and $R^9$ are H. In an embodiment when the epoxide molecule comprises two or more E2 groups, $R^5$, $R^6$, $R^7$, $R^8$, and $R^9$ can be any group described herein and the additional E2 group(s) are located in the undesignated epoxide valency.

In embodiments, the epoxide composition comprises a glycidylether molecule having at least 2 glycidylether groups having structure E2. In embodiments, the glycidylether composition can comprise a glycidylether having at least 3 glycidylether groups having structure E2. In some embodiments, the glycidylether composition comprises a mixture of glycidylether molecules having structure E2. When the glycidylether composition comprises a mixture of glycidylether molecules, the glycidylether molecules can have an average of at least 1.5 glycidylether groups having structure E2 per glycidylether molecule; alternatively, an average of at least 2 glycidylether groups having structure E2 per glycidylether molecule; alternatively, an average of at least 2.5 glycidylether groups having structure E2 per glycidylether molecule; or alternatively, an average of at least 3 glycidylether groups having structure E2 per glycidylether molecule. In embodiments, the glycidylether molecules can have an average of from 1.5 to 16 glycidylether groups having structure E2 per glycidylether molecule; alternatively, an average of from 1.5 to 12 glycidylether groups having structure E2 per glycidylether molecule; alternatively, an average of from 1.5 to 9 glycidylether groups having structure E2 per glycidylether molecule; alternatively, an average of from 2 to 7 glycidylether groups having structure E2 per glycidylether molecule; alternatively, an average of from 2 to 5 glycidylether groups having structure E2 per glycidylether molecule; or alternatively, an average of from 2 to 4 glycidylether groups having structure E2 per glycidylether molecule.

In embodiments, the polyol glycidylether can be described as a glycidylether product of contacting a polyhydric alcohol (or polyol) with an epichlorohydrin (herein referred to as "poly glycidylether product"). While this description appears to imply that the polyol glycidylether is prepared by contacting a polyol with an epichlorohydrin, this is not the intent of the description. The intent of the description is to describe the polyol glycidylether. The polyol glycidylether product can be prepared using any method apparent to those persons having ordinary skill in the art. For example, the poly glycidylether product can be prepared by contacting a polyol with an epihalohydrin (chloro, bromo or iodo) or by contacting a metal salt of a polyol with an epihalohydrin (chloro, bromo, or iodo) among other methods. The polyol component can be any aliphatic, cycloaliphatic, or aromatic polyol.

In embodiments, the polyol of the polyol glycidylether product comprises at least 2 alcohol groups (or alternatively called hydroxy groups); alternatively, at least 3 alcohol groups; or alternatively, at least 4 alcohol groups. In some embodiments, the polyol can comprise a mixture of alcohols having an average of at least 1.5 alcohol groups per alcohol molecule; alternatively, an average of at least 2 alcohol groups per alcohol molecule; alternatively, an average of at least 2.5 alcohol groups per alcohol molecule; alternatively, an average of at least 3 alcohol groups per alcohol molecule; alternatively, an average of from 1.5 to 16 alcohol groups per alcohol molecule; alternatively, an average of from 1.5 to 12 alcohol groups per alcohol molecule; alternatively, an average of from 1.5 to 9 alcohol groups per alcohol molecule; alternatively, an average of from 2 to 7 alcohol groups per alcohol molecule; alternatively, an average of from 2 to 5 alcohol groups per alcohol molecule; or alternatively, an average of from 2 to 4 alcohol groups per alcohol molecule.

In an aspect, the polyol of the polyol glycidylether product can be an aliphatic polyol. In embodiments, the aliphatic polyol of the polyol glycidylether product can comprise ethylene glycol, diethylene glycol, triethylene glycol, tetraethylene glycol, tripropylene glycol, polyethylene glycols with a molecular weight of from 106 to 8500, polyethylene glycols with a molecular weight of from 400 to 2000, 1,2-propanediol, 1,3-propanediol, 1,2-butanediol, 1,3-butanediol, 1,4-butanediol, 1,5-pentanediol, neopentyl glycol, 1,2-hexanediol, 1,6-hexanediol, 1,2-octanediol, 1,8-octanediol, 1,2-decanediol, 1,10-decanediol, glycerol, 2,2-dimethylolpropane, trimethylolethane, trimethylolpropane, pentaerythritol, dipentaerythritol, sorbitol, 1,2,4-butanetriol, 2,2,4-trimethyl-1,3-pentanediol, or combinations thereof. In some embodiments, the aliphatic polyol of the polyol glycidylether product can comprise ethylene glycol, diethylene glycol, triethylene glycol, tetraethylene glycol; alternatively, tripropylene glycol; alternatively, ethylene glycol; alternatively, diethylene glycol; alternatively, triethylene glycol; alternatively, tetraethylene glycol; alternatively, polyethylene glycols with a molecular weight of from 106 to 8500; alternatively, polyethylene glycols with a molecular weight of from 400 to 2000; alternatively, 1,2-propanediol, 1,3-propanediol, or mixtures thereof; alternatively, 1,2-butanediol, 1,3-butanediol, 1,4-butanediol, or mixtures thereof; alternatively, 1,5-pentanediol, neopentyl glycol, or mixtures, thereof; alternatively, 1,2-hexanediol, or 1,6-hexanediol; alternatively, 1,2-octanediol, or 1,8-octanediol; alternatively, 1,2-decanediol, or 1,10-decanediol; alternatively, glycerol; alternatively, 2,2-dimethylolpropane; alternatively, trimethylolethane; alternatively, trimethylolpropane; alternatively, pentaerythritol; alternatively, dipentaerythritol; alternatively, sorbitol; alternatively, 1,2,4-butanetriol; or alternatively, 2,2,4-trimethyl-1,3-pentanediol. In other embodiments, the aliphatic polyol can comprise an ethoxylate, a propoxylate, or a mixed ethoxylate/propoxylate of an aliphatic polyol or mixture of aliphatic polyols. In yet other embodiments, the polyol comprises a polyol ethoxylate product containing from 2 to 400 mol of ethylene oxide per mole of polyol.

In an aspect, the polyol of the polyol glycidylether product can be a cyclic aliphatic polyol. In embodiments, the cyclic aliphatic polyol of the polyol glycidylether product can comprise 1,2-cyclo-pentanediol, 1,3-cyclopentanediol, 1,2-cyclohexanediol, 1,3-cyclohexanediol, 1,4-cyclohexanediol, 1,2-cyclohexanedimethanol, 1,4-cyclohexanedimethanol, bis(4-hydroxycyclohexyl)methane, 2,2-bis(4-hydroxy-cyclohexyl)propane, or any combination thereof. In some embodiments, the cyclic polyol of the polyol glycidylether product can comprise 1,2-cyclopentanediol, 1,3-cyclopentanediol, or mixtures thereof; alternatively, 1,2-cyclohexanediol, 1,3-cyclohexanediol, 1,4-cyclohexanediol, or mixtures thereof; alternatively, 1,2-cyclopentanediol; alternatively, 1,3-cyclopentanediol; alternatively, 1,2-cyclohexanediol; alternatively, 1,3-cyclohexanediol; alternatively, 1,4-cyclohexanediol; alternatively, 1,2-cyclohexanedimethanol; or alternatively, 1,4-cyclohexanedimethanol; or alternatively, bis(4-hydroxycyclohexyl)methane; or alternatively, 2,2-bis(4-hydroxy-cyclohexyl)propane.

In an aspect, the polyol of the polyol glycidylether product can be an aromatic polyol. In embodiments, the aromatic polyol of the polyol glycidylether product can comprise 1-phenyl-1,2-ethanediol, 1,2-benzenediol (pyrocatechol), 1,3-benzenediol (resorcinol), 1,4-benzenediol, methyl catechol, methyl resorcinol, 1,2,4-benzenetriol, 2-hydroxybenzylalcohol, 3-hydroxybenzylalcohol, 4-hydroxybenzylalcohol, 3,5-dihydroxybenzylalcohol, 1,2-benzenedimethanol, 1,3-benzene-di-methanol, 1,4-benzene-dimethanol, 2-(2-hydroxyphenyl)ethanol, 2-(3-hydroxy-phenyl)-ethanol, 2-(4-hydroxyphenyl)-ethanol, 2-phenyl-1,2-propanediol or mixtures thereof. In some embodiments, the aromatic polyol of the polyol glycidylether product can comprise 1-phenyl-1,2-ethanediol; alternatively, 1,2-benzenediol (catechol, pyrocatechol); alternatively, 1,3-benzenediol (resorcinol); alternatively, 1,4-benzenediol; alternatively, methyl catechol; alternatively, methyl resorcinol; alternatively, 1,2,4-benzenetriol; alternatively, 2-hydroxybenzylalcohol; alternatively, 3-hydroxybenzylalcohol; alternatively, 4-hydroxybenzylalcohol; alternatively, 3,5-dihydroxybenzylalcohol; alternatively, 1,2-benzenedimethanol; alternatively, 1,3-benzene-di-methanol; alternatively, 1,4-benzenedimethanol; alternatively, 2-(2-hydroxyphenyl)ethanol; alternatively, 2-(3-hydroxy-phenyl)ethanol; alternatively, 2-(4-hydroxyphenyl)ethanol; or alternatively, 2-phenyl-1,2-propanediol.

In an aspect, the aromatic polyol of the polyol glycidylether product can be a bisphenol. In embodiments, the bisphenol can be bisphenol A (2,2-di(4-hydroxy-phenyl)propane), bisphenol AP (4,4'-(1-phenyl-ethylidene)bisphenol), bisphenol F (bis(4-hydroxy-phenyl)methane), bisphenol M (4,4'-(1,3-phenylidene-diisopropylidene)bisphenol), bisphenol P (4,4'-(1,4-phenylidene-diisopropylidene)-bisphenol), bisphenol S (4,4'-dihydroxydiphenylsulfone), bisphenol Z (4,4'-cyclohexylidene-bisphenol), or any combination thereof. In some embodiments, the bisphenol can be bisphenol A; alternatively, bisphenol AP; alternatively, bisphenol F; alternatively, bisphenol M; alternatively, bisphenol P; alternatively, bisphenol S; or alternatively, bisphenol Z.

In an aspect, the aromatic polyol of the polyol glycidylether product can be a novolak resin. Novolak resins are a broad class of resins that are produced by the condensation reaction of a phenolic compound with an aldehyde. Novolak resins are manufactured using a wide range of phenolic compounds and aldehyde combinations and can be produced in a wide range of molecular weights. Within this specification, the term "novolak resin" generally refers to the oligomerized or polymerized product of the aldehyde and phenolic compound and does not connote any indication of the degree of oligomerization, molecular weight, and/or the physical form (e.g. solid, liquid etc. . . . ) of the novolak resin.

In embodiments, the aldehyde used to produce the novolak resin can be formaldehyde. In embodiments, the phenolic compound used to produce the novolak resin can be any phenolic compound capable of undergoing a condensation reaction with an aldehyde. In some non-limiting embodiments, the phenolic compound can be phenol, a substituted phenol, catechol (pyrocatechol), a substituted catechol, resorcinol, a substituted resorcinol, 1,4-benzenediol, a substituted 1,4-benzene diol, 1,2,4-benzenetriol, bisphenol A, Bisphenol AP, bisphenol F, bisphenol M, bisphenol P, bisphenol S, bisphenol Z, or any combination thereof. In some embodiments, the phenolic compound can comprise phenol; alternatively, a substituted phenol; alternatively, catechol; alternatively, a substituted catechol; alternatively, resorcinol; alternatively, a substituted resorcinol; alternatively, 1,4-benzenediol; alternatively, a substituted 1,4-benzenediol; alternatively, 1,2,4-benzenetriol; alternatively, bisphenol A; alternatively, Bisphenol AP; alternatively, bisphenol F; alternatively, bisphenol M; alternatively, bisphenol P; alternatively, bisphenol S; or alternatively, bisphenol Z.

Within the substituted phenolic compound portion of the novolak resin, the substitute(s) can be any organyl group, a hydrocarbyl group, a halide atom, or any combination thereof. In some embodiments, the phenolic compound substituent(s) can be a $C_1$ to $C_{20}$ organyl group, a $C_1$ to $C_{20}$ hydrocarbyl group, a halide atom, or any combination thereof; alternatively, a $C_1$ to $C_{10}$ organyl group, a $C_1$ to $C_{10}$ hydrocarbyl group, a halide atom, or any combination thereof; or alternatively, a $C_1$ to $C_5$ organyl group, a $C_1$ to $C_5$ hydrocarbyl group, a halide atom, or any combination thereof.

Generally, a particular novolak resin can be indicated by prefacing the novolak resin with the aldehyde and/or phenolic compound utilized to produce the novolak resin. Thus, in embodiments, the novolak resin of the polyol glycidylether product can comprise a formaldehyde-phenol novolak resin, a formaldehyde-substituted phenol novolak resin, a formaldehyde-catechol novolak resin, a formaldehyde-substituted catechol novolak resin, a formaldehyde-resorcinol novolak resin, a formaldehyde-substituted resorcinol novolak resin, a formaldehyde-1,4-benzenediol novolak resin, a formaldehyde-substituted 1,4-benzenediol novolak resin, a formaldehyde-1,2,4-benzenetriol novolak resin, a formaldehyde-bisphenol A novolak resin, a formaldehyde-bisphenol AP novolak resin, a formaldehyde-bisphenol F novolak resin, a formaldehyde-bisphenol M novolak resin, a formaldehyde-bisphenol P novolak resin, a formaldehyde-bisphenol S novolak resin, a formaldehyde-bisphenol Z novolak resin, or any combination thereof. In other embodiments, the novolak resin of the polyol glycidylether product can comprise a formaldehyde-phenol novolak resin; alternatively, a formaldehyde-substituted phenol novolak resin; alternatively, formaldehyde-catechol novolak resin; alternatively, a formaldehyde-substituted catechol novolak resin; alternatively, a formaldehyde-resorcinol novolak resin; alternatively, a formaldehyde-substituted resorcinol novolak resin; alternatively, a formaldehyde-1,4-benzenediol novolak resin; alternatively, a formaldehyde-substituted 1,4-benzene diol novolak resin; alternatively, a formaldehyde-1,2,4-benzenetriol novolak resin; alternatively, a formaldehyde-bisphenol A novolak resin; alternatively, a formaldehyde-bisphenol AP novolak resin; alternatively, a formaldehyde-bisphenol F novolak resin; alternatively, a formaldehyde-bisphenol M novolak resin; alternatively, a formaldehyde-bisphenol P novolak resin; alternatively, a formaldehyde-bisphenol S novolak resin; or alternatively, a formaldehyde-bisphenol Z novolak resin.

In embodiments, aliphatic polyol glycidyl ethers that can be utilized within the epoxide composition can include, singly or in any combination thereof, ethylene glycol diglycidyl ether, diethylene glycol diglycidyl ether, triethylene glycol diglycidyl ether, tetraethylene glycol diglycidyl ether, tripropylene glycol diglycidyl ether, diglycidyl ethers of polyethylene glycols with a molecular weight of from 106 to 8500, diglycidyl ethers of polyethylene glycols with a molecular weight of from 400 to 2000, 1,2-propanediol diglycidyl ether, 1,3-propanediol diglycidyl ether, 1,2-butanediol diglycidyl ether, 1,3-butanediol diglycidyl ether, 1,4-butanediol diglycidyl ether, 1,5-pentanediol diglycidyl ether, neopentyl glycol diglycidyl ether, 1,2-hexanediol diglycidyl ether, 1,6-hexanediol diglycidyl ether, 1,2-cyclohexanediol diglycidyl ether, 1,4-cyclohexanediol diglycidyl ether, 1,2-octanediol diglycidyl ether, 1,8-octanediol diglycidyl ether, 1,2-decanediol diglycidyl ether, 1,10-decanediol diglycidyl ether, glycerol triglycidyl ether, 2,2-dimethylolpropane diglycidyl ether, trimethylolethane triglycidyl ether, trimethylolpropane diglycidyl ether, pentaerythritol tetraglycidyl ether, dipentaerythritol tetraglycidyl ether, dipentaerythritol hexaglycidyl ether, sorbitol tetraglycidyl ether, sorbitol hexaglycidyl ether, 1,2,4-butanetriol triglycidyl ether, 2,2,4-trimethyl-1,3-pentanediol triglycidyl ether, or combinations thereof. In some embodiments, aliphatic polyol glycidyl ethers that can be utilized within the epoxide composition can comprise ethylene glycol diglycidyl ether, diethylene glycol diglycidyl ether, triethylene glycol diglycidyl ether, tetraethylene glycol diglycidyl ether; alternatively, tripropylene glycol diglycidyl ether; alternatively, ethylene glycol diglycidyl ether; alternatively, diethylene glycol diglycidyl ether; alternatively, triethylene glycol diglycidyl ether; alternatively, tetraethylene glycol diglycidyl ether; alternatively, diglycidyl ethers of polyethylene glycols with a molecular weight of from 106 to 8500; alternatively, diglycidyl ethers of polyethylene glycols with a molecular weight of from 400 to 2000; alternatively, 1,2-propanediol diglycidyl ether, 1,3-propanediol diglycidyl ether, or mixtures thereof; alternatively, 1,2-butanediol diglycidyl ether, 1,3-butanediol diglycidyl ether, 1,4-butanediol diglycidyl ether, or mixtures thereof; alternatively, 1,5-pentanediol diglycidyl ether, neopentyl glycol diglycidyl ether, or mixtures, thereof; alternatively, 1,2-cyclohexanediol diglycidyl ether, 1,4-cyclohexanediol diglycidyl ether, or mixtures thereof; alternatively, 1,2-hexanediol diglycidyl ether or 1,6-hexanediol diglycidyl ether; alternatively, 1,2-octanediol diglycidyl ether or 1,8-octanediol diglycidyl ether; alternatively, 1,2-decanediol diglycidyl ether or 1,10-decanediol diglycidyl ether; alternatively, glycerol triglycidyl ether; alternatively, 2,2-dimethylolpropane diglycidyl ether; alternatively, trimethylolethane triglycidyl ether; alternatively, trimethylolpropane triglycidyl ether; alternatively, pentaerythritol tetraglycidyl ether; alternatively, dipentaerythritol hexaglycidyl; alternatively, dipentaerythritol tetraglycidyl ether; alternatively, sorbitol tetraglycidyl ether; sorbitol hexaglycidyl ether; alternatively, 1,2,4-butanetriol triglycidyl ether; or alternatively, 2,2,4-trimethyl-1,3-pentanediol diglycidyl ether. In other embodiments, aliphatic polyol glycidyl ethers that can be utilized within the epoxide composition can comprise a polyglycidyl ether of an ethoxylate, a propoxylate, or a polyglycidyl ether of a mixed ethoxylate/propoxylate of a polyol or mixture of a polyols. In yet other embodiments, aliphatic polyol glycidyl ethers that can be utilized within the epoxide composition can comprise a polyglycidyl ether of a polyol ethoxylate product containing from 2 to 400 mol of ethylene oxide per mole of polyol.

In embodiments, cyclic polyol glycidyl ethers that can be utilized within the epoxide composition can include, singly or in any combination thereof, 1,2-cyclopentanediol diglycidyl ether, 1,3-cyclopentanediol diglycidyl ether, 1,2-cyclohexanediol diglycidyl ether, 1,3-cyclohexanediol diglycidyl ether, 1,4-cyclohexanediol diglycidyl ether, 1,2-cyclohexanedimethanol diglycidyl ether, 1,4-cyclohexanedimethanol diglycidyl ether, bis(4-hydroxycyclohexyl)methane diglycidyl ether, 2,2-bis(4-hydroxy-cyclo-hexyl)-propane diglycidyl ether, or any combination thereof. In some embodiments, aliphatic polyol glycidyl ethers that can be utilized within the epoxide composition can comprise 1,2-cyclopentanediol diglycidyl ether, 1,3-cyclopentanediol diglycidyl ether, or mixtures thereof; alternatively, 1,2-cyclohexanediol diglycidyl ether, 1,3-cyclohexanediol diglycidyl ether, 1,4-cyclohexanediol diglycidyl ether, or mixtures thereof; alternatively, 1,2-cyclopentanediol diglycidyl ether; alternatively, 1,3-cyclopentanediol diglycidyl ether; alternatively, 1,2-cyclohexanediol diglycidyl ether; alternatively, 1,3-cyclohexanediol diglycidyl ether; alternatively, 1,4-cyclohexanediol diglycidyl ether; alternatively, 1,2-cyclohexanedimethanol diglycidyl ether; alternatively, 1,4-cyclohexanedimethanol diglycidyl ether; alternatively, bis(4-hydroxycyclohexyl) methane diglycidyl ether; or alternatively, 2,2-bis(4-hydroxy-cyclo-hexyl)-propane diglycidyl ether.

In embodiments, aromatic polyol glycidyl ethers that can be utilized within the epoxide composition can include, singly or in any combination thereof, 1-phenyl-1,2-ethanediol diglycidyl ether, 1,2-benzenediol diglycidyl ether (pyrocatechol diglycidyl ether), 1,3-benzenediol diglycidyl ether (resorcinol diglycidyl ether), 1,4-benzenediol diglycidyl ether, methyl catechol diglycidyl ether, methyl resorcinol diglycidyl ether, 1,2,4-benzenetriol triglycidyl ether, 2-hydroxybenzylalcohol diglycidyl ether, 3-hydroxybenzylalcohol diglycidyl ether, 4-hydroxybenzylalcohol diglycidyl ether, 3,5-dihydroxybenzylalcohol diglycidyl ether, 1,2-benzenedimethanol diglycidyl ether, 1,3-benzene-dimethanol diglycidyl ether, 1,4-benzene-dimethanol diglycidyl ether, 2-(2-hydroxyphenyl)ethanol diglycidyl ether, 2-(3-hydroxy-phenyl)-ethanol diglycidyl ether, 2-(4-hydroxy-phenyl)ethanol diglycidyl ether, or 2-phenyl-1,2-propanediol diglycidyl ether. In embodiments, aromatic polyol glycidyl ethers that can be utilized within the epoxide composition can be 1-phenyl-1,2-ethanediol diglycidyl ether; alternatively, 1,2-benzenediol diglycidyl ether; alternatively, 1,3-benzenediol diglycidyl ether; alternatively, 1,4-benzenediol diglycidyl ether; alternatively, methyl catechol diglycidyl ether; alternatively, methyl resorcinol diglycidyl ether; alternatively, 1,2,4-benzenetriol triglycidyl ether; alternatively, 2-hydroxybenzylalcohol diglycidyl ether; alternatively, 3-hydroxybenzylalcohol diglycidyl ether; alternatively, 4-hydroxybenzylalcohol diglycidyl ether; alternatively, 3,5-dihydroxybenzylalcohol diglycidyl ether; alternatively, 1,2-benzenedimethanol diglycidyl ether; alternatively, 1,3-benzenedimethanol diglycidyl ether; alternatively, 1,4-benzenedimethanol diglycidyl ether; alternatively, 2-(2-hydroxyphenyl)ethanol diglycidyl ether; alternatively, 2-(3-hydroxy-phenyl)ethanol diglycidyl ether; alternatively, 2-(4-hydroxyphenyl)ethanol diglycidyl ether; or alternatively, 2-phenyl-1,2-propanediol diglycidyl ether.

In embodiments, the glycidyl ether that can be utilized within the epoxide composition can be a novolak polyglycidyl ether (a glycidylether product of a novolak resin). In embodiments, the novolak polyglycidyl ethers that can be utilized within the epoxide composition can include a formaldehyde-phenol novolak polyglycidyl ether, a formaldehyde-substituted phenol novolak polyglycidyl ether, a formaldehyde-catechol novolak polyglycidyl ether, a formaldehyde-substituted catechol novolak polyglycidyl ether, a formaldehyde-resorcinol novolak polyglycidyl ether, a formaldehyde-substituted resorcinol novolak polyglycidyl ether, a formaldehyde-1,4-benzenediol novolak polyglycidyl ether, a formaldehyde-substituted 1,4-benzene diol novolak polyglycidyl ether, a formaldehyde-1,2,4-benzenetriol novolak polyglycidyl ether, a formaldehyde-bisphenol A novolak polyglycidyl ether, a formaldehyde-bisphenol AP novolak polyglycidyl ether, a formaldehyde-bisphenol F novolak polyglycidyl ether, a formaldehyde-bisphenol M novolak polyglycidyl ether, a formaldehyde-bisphenol P novolak polyglycidyl ether, a formaldehyde-bisphenol S novolak polyglycidyl ether, a formaldehyde-bisphenol Z novolak polyglycidyl ether, or any combination thereof. In other embodiments, the novolak polyglycidyl ether of the polyol glycidylether product can comprise a formaldehyde-phenol novolak polyglycidyl ether; alternatively, a formaldehyde-substituted phenol novolak polyglycidyl ether; alternatively, formaldehyde-catechol novolak polyglycidyl ether; alternatively, a formaldehyde-substituted catechol novolak polyglycidyl ether; alternatively, a formaldehyde-resorcinol novolak polyglycidyl ether; alternatively, a formaldehyde-substituted resorcinol novolak polyglycidyl ether; alternatively, a formaldehyde-1,4-benzenediol novolak polyglycidyl ether; alternatively, a formaldehyde-substituted 1,4-benzene diol novolak polyglycidyl ether; alternatively, a formaldehyde-1,2,4-benzenetriol novolak polyglycidyl ether; alternatively, a formaldehyde-bisphenol A novolak polyglycidyl ether; alternatively, a formaldehyde-bisphenol AP novolak polyglycidyl ether; alternatively, a formaldehyde-bisphenol F novolak polyglycidyl ether; alternatively, a formaldehyde-bisphenol M novolak polyglycidyl ether; alternatively, a formaldehyde-bisphenol P novolak polyglycidyl ether; alternatively, a formaldehyde-bisphenol S novolak polyglycidyl ether; or alternatively, a formaldehyde-bisphenol Z novolak polyglycidyl ether.

The following examples are included to demonstrate specific embodiments of the invention. Those of skill in the art should appreciate that the techniques disclosed in the examples represent techniques discovered to function well in the practice of the invention. However, in light of the present disclosure, those of skill in the art should will appreciate the changes that can be made in the specific disclosed embodiments and still obtain similar results that do not depart from the spirit and scope of the invention

EXAMPLES

Runs 1-11 describe the production of esters having multiple terminal double bonds using various methods. Runs 1-4 describe the production of the esters having multiple terminal double bonds via the esterification of polyols with carboxylic acids having terminal double bonds. Runs 5-9 describe the production of the esters having multiple terminal double bonds via the transesterification with the mono-alcohol esters of carboxylic acids having terminal double bonds with polyols. Runs 10-11 describes the production of the esters having multiple terminal double bonds via metathesis of esters having internal double bonds with ethylene.

Runs 12-17 describe the production of esters having multiple thiol groups from the ester having multiple terminal double bonds produced in Runs 5, 6, 7, and 8.

Methyl 1—Decenoate Transesterification with Polyols

Run 1

Toluene (120 mL), methyl 10-decenoate (166.15 g), trimethylolpropane (34.16 g), and sodium acetate (0.418 g) were charged to a 500-mL round-bottomed flask equipped with a heating mantel, thermocouple, magnetic stirrer, and dean stark trap. The reaction mixture was heated to reflux (130° C.-192° C.). Reflux was continued for 5.5 hours. After this time period, the conversion of polyol alcohol groups to 10-decenoate esters as measured by GC peak area was 20%. The solution was cooled and sodium methoxide was added to the round-bottomed flask and the reaction mixture heated to reflux (140° C.-165° C.) for 2 hours. After this time period the GC area conversion had increased to 56%.

Runs 2-4

Methyl 10-decenoate, the polyol, and dibuyltin oxide were charged to a 500 mL round-bottomed flask equipped with a heating mantle, thermocouple, magnetic stirrer, and Dean-Stark trap. The reaction mixture was heated to reflux and maintained at reflux to allow the reaction to proceed. Table 1 provides reaction information for Experiments 2-4.

The reaction mixture was then vacuum-distilled to remove most of the unreacted methyl 10-undecenoate. The product was the subjected to wiped film evaporation (at <2 mmHg and 155° C. using a ~60 mL/min feed rate) to remove residual methyl 10-decenoate. Table 2 provides the distillation information for Experiments 2-4.

All heating stages of the reaction and product isolation were conducted under a nitrogen atmosphere or under vacuum (with the vacuum bleed valve attached to nitrogen).

Runs 5-9

The polyol, 10-decenoic acid, and the catalyst oxide were charged to a 500 mL round-bottomed flask equipped with a heating mantle, thermocouple, magnetic stirrer, and Dean-Stark trap. The reaction mixture was heated to refluxing and maintained at reflux to allow the reaction to proceed. Table 3 provides reaction information for Experiments 5-9.

The reaction mixture was then vacuum distilled to remove most of the unreacted 10-undecenoic acid. The product was subjected to wiped film evaporation (at <2 mmHg and 155° C. using a ~60 mL/min feed rate) to remove residual 10-decenoic acid. Table 4 provides the distillation information for Experiments 5-9. Within Tables 1, 2, 3 and 4, GC conversion provides the percentage of polyol hydroxyl groups that were converted to 10-decenoate esters as determined by GC area.

All heating stages of the reaction and product isolation were conducted under a nitrogen atmosphere or under vacuum (with the vacuum bleed valve attached to nitrogen).

TABLE 1

Reaction of Polyols with Methyl 10-Undecenoate

| Run | Ester (mass) | Polyol (mass) | Ester/Polyol Equiv. Ratio | Catalyst (mass) | Temp. Range (° C.) | Time (hours) | GC Conversion (Area %) |
|---|---|---|---|---|---|---|---|
| 2 | Methyl 10-undecenoate (204.26 g) | Trimethylolpropane (45.38 g) | 1.02 | Dibutyltin oxide (0.131 g) | 198-259 | 10 | 80.3 |
| 3 | Methyl 10-undecenoate (186.69 g) | Trimethylolpropane (33.81 g) | 1.25 | Dibutyltin oxide (0.371 g) | 180-249 | 5.5 | 90.5 |
| 4 | Methyl 10-undecenoate (193.56 g) | Pentaerythritol (26.58 g) | 1.25 | Dibutyltin oxide (0.398 g) | 186-252 | 4 | 92.9 |

TABLE 2

Distillation of Product Produced from the Reaction of Reaction of Polyols with Methyl 10-Undecenoate

| | Vacuum Distillation | | | | Wiped Film Evaporation | |
|---|---|---|---|---|---|---|
| Run | Temp. Range (° C.) | Pressure. Range (mmHg) | Time (hours) | GC Conversion (Area %) | GC Conversion (Area %) | Residual Methyl 10-Undecenoate |
| 2* | 179-189 | 47-9 | — | 80.0 | 80.0 | 0.3621 |
| 3 | 108-138 | 11-0 | 3 | 90.6 | 91.0 | 0.079 |
| 4 | 107-159 | 15-9 | 1 | 96.3 | 96.4 | 0.144 |

*Wiped Film Evaporation not performed on this experiment. Product yield, purity, and residual methyl undecenoate values are those after vacuum distillation.

TABLE 3

Reaction of Polyols with 10-Undecenoic Acid

| Run | Ester (mass) | Polyol(mass) | Acid/Polyol Equiv. Ratio | Catalyst (mass) | Temp. Range (° C.) | Time (hours) | GC Conversion (Area %) |
|---|---|---|---|---|---|---|---|
| 5 | 10-undecenoic Acid (167.25 g) | Trimethylolpropane (32.51 g) | 1.25 | Dibutyltin oxide (0.373 g) | 160-215 | 5.5 | 96.6 |
| 6 | 10-undecenoic Acid (178.39 g) | Glycerol (24.3 g) | 1.22 | Dibutyltin oxide (0.398 g) | 178-240 | 2.5 | — |
| 7 | 10-undecenoic Acid (152.47 g) | Unoxol ™ diol (49.51 g) | 1.21 | Dibutyltin oxide (0.359 g) | 152-238 | 4.5 | 98.1 |
| 8 | 10-undecenoic Acid (191.85 g) | Pentaerythritol (28.32 g) | 1.25 | Dibutyltin oxide (0.415 g) | 162-220 | 3.0 | 98.6 |
| 9 | 10-undecenoic Acid (191.89 g) | Pentaerythritol (28.49 g) | 1.24 | CYCAT (1.840 g) | 151-175 | 4.0 | 98.1 |

TABLE 4

Distillation of Product Produced from the Reaction of Polyols with 10-Undecenoic Acid.

| | Vacuum Distillation | | | | Wiped Film Evaporation | | |
|---|---|---|---|---|---|---|---|
| Run | Temp. Range (° C.) | Pressure. Range (mmHg) | Time (hours) | GC Conversion (Area %) | GC Conversion (Area %) | Residual Undecenoic Acid | Product $M_n$ |
| 5 | 161-243 | 6-4 | 3.5 | 99.0 | 98.8 | 0.0874 | 632.96 |
| 6 | 222-240 | 2-1 | 3.5 | 99.5 | 99.6 | 0.1434 | 590.88 |
| 7 | 179-238 | 2 | 2.75 | 98.7 | 98.7 | 0.2922 | 476.74 |
| 8 | 160-220 | 3 | 3 | 99.7 | 99.7 | 0.8249 | 801.2 |
| 9 | 175-225 | 9-2 | 4 | 98.2 | 98.0 | 0 | — |

Production of Glycerol Tris(9-Decenoate) via Metathesis of Soy Bean Oil

Run 10

Soy bean oil is treated with alumina to reduce the peroxide content to less than 10 milliequivalents peroxide per kg of soybean oil. The soybean oil is then degassed by bubbling nitrogen through the alumina treated soybean oil for 30 minutes. The treated soybean oil is then stored in container under a nitrogen atmosphere until it is used.

To a clean 500 ml stainless steel autoclave equipped with a magnetic stirring apparatus, heating apparatus, and a gas inlet valve is added 250 mL of the alumina treated and degassed soybean oil. To the magnetic stirrer impeller is attached a seal glass tube containing 35 milligrams of tricyclohexylphosphine)benzylideneruthenium chloride dissolved in 5 ml of toluene. The autoclave is closed, evacuated, and placed under 60 psig nitrogen pressure for 1 minute. The autoclave is then evacuated, and placed under 80 psig nitrogen for 1 minute two additional times. The autoclave is then evacuated and pressurized to 400 psig ethylene. The ethylene supply is then left open for the reaction. Stirring is initiated to break the glass tube containing the tricyclohexylphosphine)benzylideneruthenium chloride. The autoclave is heated to 30° C., and maintained for 10 hours.

The autoclave is allowed to cool and the contents passed through and alumina column to remove the tricyclohexylphosphine)benzylideneruthenium chloride. The product is then subjected to wiped film evaporation to separate the glycerol tris(9-decenoate) from the by-products. The product is obtained having greater than 70 percent yield. Methanolysis of the product is performed on the product. The product is found to contain greater than 90 percent 9-decenoate residues.

Production of Glycerol Tris(9-Decenoate) via Metathesis of Castor Bean Oil

Run 11

Castor bean oil is treated with alumina to reduce the peroxide content to less than 10 milliequivalents peroxide per kg of castor bean oil. The castor bean oil is then degassed by bubbling nitrogen through the alumina treated castor bean oil for 30 minutes. The treated castor bean oil is then stored in container under a nitrogen atmosphere until it is used.

To a clean 500 ml stainless steel autoclave equipped with a magnetic stirring apparatus, heating apparatus, and a gas inlet valve is added 250 mL of the alumina treated and degassed castor bean oil. To the magnetic stirrer impeller is attached a seal glass tube containing 35 milligrams of 1,3-bis-(2,4,6-trimethylphenyl)-2-(imidazolidinylidene)(phenylmethylene)dichloro(tricyclohexyl phosphine) ruthenium dissolved in 5 ml of toluene. The autoclave is closed, evacuated, and placed under 60 psig nitrogen pressure for 1 minute. The autoclave is then evacuated, and placed under 80 psig nitrogen for 1 minute two additional times. The autoclave is then evacuated and pressurized to 400 psig ethylene. The ethylene supply is then left open for the reaction. Stirring is initiated to break the glass tube containing the tricyclohexylphosphine)benzylideneruthenium chloride. The autoclave is heated to 30° C., and maintained for 10 hours.

The autoclave is allowed to cool and the contents passed through and alumina column to remove the tricyclohexylphosphine)benzylideneruthenium chloride. The product is then subjected to wiped film evaporation to separate the glycerol tris(9-decenoate) from the by-products. The product is obtained having greater than 70 percent yield. Methanolysis of the product is performed on the product. The product is found to contain greater than 90 percent 9-decenoate residues.

Preparation of Terminal Thiols

Runs 12-17 —General Procedure

The esters having multiple terminal thiol groups were prepared by charging trimethylolpropane tris(10-undecenoate) produced in Run 5, pentaerythritol tetrakis(10-undecenoate) produced in Run 8, Unoxol™ bis(10-undecenoate) produced in Run 7, or glycerol tris(10-undecenoate) produced in Run 6 to a clean 1.5 L stainless steel (316) reactor via a ¼ inch top port. Tributyl phosphite (TBP) was then added to the stainless steel reactor by syringe through a top port (to remove residual elemental sulfur in the subsequently charged $H_2S$). The stainless steal reactor was sealed and the headspace pressured and de-pressured with dry $N_2$ (3 times) to remove oxygen. Liquid $H_2S$, was then added to the reactor by pressuring the desired weight of from a pressurized cylinder of $H_{2S}$ placed on a balance. Once the $H_2S$ charge was completed, the reactor mixture was warmed using heating/cooling coils attached to a circulating bath and stirred at 800 rpm utilizing a turbine-type mixer. Stirring was continued for one hour to allow the TBP to react with the elemental sulfur.

The contents of the stainless steel reactor were then heated to 40° C. using heating/cooling coils attached to a circulating bath. Once the reaction temperature was attained, the reaction was initiated by supplying power to a low pressure (100 Watts) mercury-vapor UV light (inside a synthetic quartz lamp well) submerged within the reaction mixture inside the stainless steel reactor. The reaction was continued for two hours. The UV lamp was then turned off and the excess $H_{2S}$ is vented to a high pressure flare system. The headspace is swept with $N_2$ at 40 SCFH (standard cubic feet per hour) for ~30 minutes to remove residual $H_2S$.

Liquid products (those produced from trimethylolpropane tris(10-undecenoate) and glycerol tris(10-undecenoate) were drained to a clean container and the tributyl phosphite was removed from the product by passing the product through a wiped film evaporator at 135° C. and <2 mmHg.

Partially solid products (those produced from pentaerythritol tetrakis(10-undecenoate) and Unoxol™ bis(10-undecenoate)), were removed from the stainless steel reactor by charging the reactor with 1.1 L of tetrahydrofuran and stirring to dissolve the product. The reactor contents were then discharged into a 1 L round bottomed flask. The tetrahydrofuran was removed from the product by rotary evaporation (at 110 mmHg and 44° C.). The tributyl phosphite was then removed from the product by passing the product through a wiped film evaporator at 135° C. and <2 mmHg.

The final products were characterized by methanolysis/GC (to determine conversion of the double bonds), FTIR (to observe the consumption of the olefinic peak), iodine titration (to determine the % mercaptan sulfur value), and $^1H$ and $^{13}C$ NMR analysis.

Table 5 provides the information regarding the charges to the stainless steel reactor for Runs 12-17. Table 6 provides the results of the analytical tests performed on the products produced in Runs 12-17.

TABLE 5

Reaction of Unsaturated Esters having Multiple Carbon-Carbon Double Bonds with Hydrogen Sulfide.

| Run | Olefin of Run (mass in g) | Tributyl-phosphite mass (g) | $H_2S$ mass (g) | Olefin/$H_2S$ Molar Ratio | Reaction Temperature (° C.) | Reaction Pressure (psig) |
|---|---|---|---|---|---|---|
| 12 | trimethylolpropane tris(10-undecenoate) of Run 5 (41.00) | 1.2 | 660 | 100.7 | 34.3-35.9 | 420-434 |
| 13 | pentaerythritol tetrakis(10-undecenoate) of Run 8, (44.35) | 1.4 | 760 | 101.0 | 32.9-35.7 | 457-458 |
| 14 | Unoxol ™ bis(10-undecenoate) of Run 7 (52.10) | 1.4 | 760 | 103.3 | 31.5-33.6 | 430-454 |

TABLE 5-continued

Reaction of Unsaturated Esters having Multiple Carbon-Carbon Double Bonds with Hydrogen Sulfide.

| Run | Olefin of Run (mass in g) | Tributyl-phosphite mass (g) | $H_2S$ mass (g) | Olefin/$H_2S$ Molar Ratio | Reaction Temperature (° C.) | Reaction Pressure (psig) |
|---|---|---|---|---|---|---|
| 15 | glycerol tris(10-undecenoate) of Run 6 (43.09) | 1.4 | 760 | 102.3 | 32.3-32.9 | 433-446 |
| 16 | Unoxol ™ bis(10-undecenoate) of Run 7 (53.0)) | 2.2 | 760 | 101.6 | 37.0-37.4 | 426-433 |
| 17 | pentaerythritol tetrakis(10-undecenoate) of Run 8 (44.50) | 2.2 | 760 | 100.6 | 37.3 0 37.7 | 432-442 |

TABLE 6

Yield and Properties of Thiol Esters Having Terminal Thiol Groups.

| Run | Product Weight | Conversion[‡] | Purity[1] | Mercaptan Sulfur | Equivalent Weight[3] |
|---|---|---|---|---|---|
| 12 | 43.00 | 98.7 | 95.79 | 11.55 | 250.5 |
| 13 | 35.53 | 88.44 | 100 | 12.05 | 265.6 |
| 14 | 47.70 | 65.1 | 94.1 | — | 423.4 |
| 15 | 36.46 | 87.22 | 90.5 | 10.34 | 265.8 |
| 16 | 47.22 | 97.87 | 90.1 | 10.60 | 281.6 |
| 17 | 39.35 | 99.2 | 90.8 | 12.42 | 236.8 |

[‡]Based upon Methanolysis. This value represent the percentage of undecenoate units converted to thioundecanoate units.
[1]Based upon Methanolysis of product.
[3]Calculated from the molecular weight of the starting terminal olefinic ester and the conversion Polythiourethane Production Polythiourethanes were produced using pentaerythritol tetrakis(11-mercapto undecanoate) (TMU) as the polyhydric material and hexamethylene diisocyanate trimer (Basonat® HI 290B). This polythiourethane was compared to the polythiourethanes produced from mercaptanized epoxidized soybean oil (MHSO) produced according to the methods disclosed in U.S. patent application Ser. No. 11/060,675 filed on Feb. 17, 2005, which is entitled "Thiol Ester Compositions and Processes for Making and Using Same" and Basonat® HI 290B, mercaptanized castor oil (MCO) produced according to the methods disclosed in U.S. patent application Ser. No. 11/060,675 filed on Feb. 17, 2005, which is entitled "Thiol Ester Compositions and Processes for Making and Using Same" and Basonat® HI 290B, and castor oil and Basonat® HI 290B.

The polyhydric materials pentaerythritol tetrakis(11-mercapto undecanoate), mercaptanized epoxidized soybean oil, mercaptanized castor oil, and castor oil, along with the polyisocyanate (Basonat® HI 290B—hexamethylene diisocyanate trimer) and solvent (butyl acetate) were dried using standard procedures to a moisture level of less than 500 ppm.

Runs 18-21—General Preparations

Glassware and syringes utilized to prepare the polythiourethanes were pre-dried in an oven at >110° C. for at least 2 hours and then allowed to cool under a dry nitrogen purge just before use.

The polythiourethanes were produced using a catalyst solution containing dibutyl tin dilaurate (DBTDL) and Addocat® PP, in dried butyl acetate. The catalyst solution utilized was never more than three days old. Generally, the catalyst solution was prepared by weighing into a oven-dried bottle placed on a 3-place balance, DBTDL, Addocat PP, and the catalyst solvent (butyl acetate). The bottle was then purged with nitrogen, capped with a rubber septum, and swirled to dissolve the catalyst. In one instance the catalyst solution was prepared using 0.5833 grams DBTDL, 1.1667 grams Addocat PP catalyst, and 33.25 g of anhydrous butyl acetate.

Runs 18-21—Polythiourethane Formulation Preparation—General Procedure

An Erlenmeyer flask was placed on a 3- or 4-place balance. The polyhydric material was weighed into the flask followed by the solvent, butyl acetate. The headspace of the flask was purged with nitrogen, sealed with a rubber septum, and swirled until complete dissolution had occurred. The flask was periodically opened to relieve built-up pressure. Once dissolution had occurred, the catalyst was added to the flask using a pipette. The solution was then swirled to mix the solution. The flask was then purged with nitrogen and sealed with a rubber septum. Table 7 provides the formulation data for the polythiourethane formulations.

Runs 18-21—Polythiourethane Coating Formation and Testing—General Procedure

Once the polythiourethane formulation solution was well mixed, test panels were prepared by pipetting aliquots of the formulation mixture onto a test panels and drawing down the formulation with a 5 mil WFT drawdown bar. Once drawn down the test panels were placed in a vented drying cabinet.

A Byk dry time panel was prepared on a glass panel and the Byk dry time recorder started immediately after the formulation solution was drawn down. The Byk dry time was determined by ASTM Method D 5895-03, "Standard Test Methods for Evaluating Drying or Curing During Film Formation of Organic Coatings Using Mechanical Recorders," Test Method A—Straight Line Drying Time.

Additional test panels were prepared by pipetting aliquots of the formulation mixture onto a test panels and drawing down the formulation with a 5 mil WFT drawdown bar. These test panels were allowed to cure at ambient temperature for ten minutes and then placed in a 130° C. oven for 3 hours. The test panels were then allowed to cool overnight before testing.

MEK resistance was tested by wetting a small area on the coated test panel with methyl ethyl ketone. A cotton swab was rubbed, back and forth, across the methyl ethyl ketone wetted area of the coating by holding the swab tip firmly but lightly against the coating. Each back and forth stroke is called a double rub. The number of strokes was counted until resistance was felt during the rub (due to solvent softening or removal of the coating), or until 50 double rubs was reached (whichever comes first). The rubbing was then stopped and the methyl ethyl ketone removed from the coated test panel by gently rubbing with a Kimwipe®. The test area was then visually inspected to determine if any visible changes (physical damage, whitening, and/or softening) had occurred to the coating and noted. If the coating was damaged in under 50 strokes, another fresh test was prepared using fewer strokes to get a more accurate number of strokes the coating could withstand before sustaining visible damage. If no visible changes were observed the procedure was repeated for an additional 50 double rubs or until the coating appeared to be affected. The procedure was repeated until the coating was affected or 200 double rubs (in total). The highest number of double rubs the coating is able to withstand before suffering visible damage is reported Table 7 provides the polythiourethane coating test data.

TABLE 7

Polythiourethane Formulation and Coating Test Data

Polythiourethane Formulation

| Thiol, grams | TMU, 25.46 | MHSO, 32.05 | MCO, 24.86 |
|---|---|---|---|
| Basonat ® HI 290B, grams | 29.62 | 41.8 | 36.46 |
| Butyl Acetate | 9.78 | 65.82 | 20.72 |
| Dibutyltin Diluarate, mL | 0.016 | 0.016 | 0.016 |
| Addocat PP (20% solution in Butyl Acetate), mL | 0.140 | 0.200 | 0.160 |

Polythiourethane Coating Test data

| Cure Temperature, ° C. | 150 | 150 | 150 |
|---|---|---|---|
| Cure Time, minutes | 180 | 180 | 180 |
| Set to Touch, minutes | 6 | 5 | 90 |
| Tack-Free Time, minutes | 10 | 15 | 175 |
| Dry-Through Time, minutes | 65 | >180 | >180 |
| MEK Resistance, # Double Rubs | >200 | >200 | >200 |
| Peroz Hardness, post cure swings | 264 | 311 | 227 |
| Peroz Harness, 24 hours, swings | 286 | 314 | 304 |
| 20 degree gloss, % | 92.6 | 86.9 | 86.4 |
| 60 degree gloss, % | 99.7 | 98.7 | 99.1 |
| 85 degree gloss, % | 97.7 | 97.1 | 97.7 |
| Forward Impact, inch-lb | >188 | >188 | >188 |
| Reverse Impact, in-lb | >188 | 100 | >188 |
| Crosshatch Rating | 5 | 5 | 5 |
| Pencil Hardness Rating | 5 H | F | HB |
| Nandrel Bend, Inches | <1/8 | <1/8 | <1/8 |

Thiol Ene Coating Formulations

A thiol-ene coating formulation was produced using the trimethylolpropane tris(11-mercapto undecanoate) of Run 12 and compared to thiol-ene coating formulation produced without trimethylolpropane tris(11-mercapto undecanoate). The coating formulations were coated on Bonderite-treated CRS test panels and evaluated for their chemical resistance.

Runs 22-27 —General Preparations

Glassware utilized to prepare the thiol-ene coatings were pre-dried in an oven at >110° C. for at least 2 hours and then allowed to cool under a dry nitrogen purge just before use. The Bonderite 1000-treated CRS test panels were used as received.

A nitrogen atmosphere was maintained over the materials place into the sample preparation bottle by purging the headspace of the bottle with nitrogen after the addition of each component.

Runs 22-27 —Thiol Ene Formulation Preparation—General Procedure

A bottle was place on a 3-place or 4-place balance. Into the bottle was weighed the polymercaptan and the photoinitiator. The photoinitiator was charged using a lab area equipped with red light, to avoid exposing the photoinitiators to harmful ambient lighting conditions before passing through the UV cure line. After the photoinitiator was added into the bottle, the solution was swirled or stirred using a small magnetic stir bar to mix the components. Into the solution, was weighed the polyene, 1,3,5-triallyl-1,3,5-triazine-2,4,6(1H,3H,5H)-trione. The solution was then swirled to create a single phase solution and the headspace of the bottle was then purged with nitrogen. The bottle was then stored in a dark place when not used to prepare the coating panels.

Runs 22-27 —Thiol Ene Coated Test Panel Preparation and Testing—General Procedure Coating test panels were prepared by pipetting aliquots of the formulation mixture onto a test panels and drawing down the formulation with a 2 mil WFT drawdown bar. The cure speed was then tested by passing the test panel through a Fusion UV Cure line at ambient temperature.

A test panel was passed through the Fusion UV cure line ten times at a line speed of 53 feet per minute and the MEK resistance was tested. The UV radiation incident on the test panels, per pass, was determined by passing a portable UV measuring device through the Fusion UV cure line at a 53 fpm cure line speed. The measured incident radiation per pass was approximately 154 mJ/cm$^2$ (average of three independent values.

The initial cure of the coatings was measured by development of resistance to MEK using the following procedure.

A small area on the coated test panel was wetted with methyl ethyl ketone. A cotton swab was rubbed, back and forth, across the methyl ethyl ketone wetted area of the coating by holding the swab tip firmly but lightly against the coating. Each back and forth stroke is called a double rub. The number of strokes was counted until resistance was felt during the rub (due to solvent softening or removal of the coating), or until 50 double rubs was reached (whichever comes first). The rubbing was then stopped and the methyl ethyl ketone removed from the coated test panel by gently rubbing with a Kimwipe®. The test area was then visually inspected to determine if any visible changes (physical damage, whitening, and/or softening) had occurred to the coating and noted. If the coating was damaged in under 50 strokes, another fresh test was prepared using fewer strokes to get a more accurate number of strokes the coating could withstand before sustaining visible damage. If no visible changes were observed the procedure was repeated for an additional 50 double rubs or until the coating appeared to be affected. The procedure was repeated until the coating was affected or 200 double rubs (in total). The highest number of double rubs the coating is able to withstand before suffering visible damage is reported.

Table 8 provides the formulation data and test data for the thiol-ene coating compositions.

TABLE 8

Preparation and testing of Thiol-Ene Coating Test Panels[†]

| Materials | 22 | 23 | 24 | 25 | 26 | 27 |
|---|---|---|---|---|---|---|
| Trimethylolpropane tris(2-mercaptoacetate), grams | | | 9.00 | 9.00 | 18.01 | 7.28 |
| Mercaptanized Soybean Oil (grams) | 18.00 | 18.00 | 9.00 | 9.00 | | |
| Trimethylolpropane tris(11-mercaptoundecanoate) (grams) | | | | | | 8.84 |

TABLE 8-continued

Preparation and testing of Thiol-Ene Coating Test Panels[†]

| Materials | 22 | 23 | 24 | 25 | 26 | 27 |
|---|---|---|---|---|---|---|
| 1,3,5-triallyl-1,3,5-triazine-2,4,6(1H,3H,5H)-trione (grams) | 4.49 | 4.49 | 8.24 | 8.24 | 12.66 | 7.89 |
| Darocur 1173 (grams) | 0.3369 | | 0.3957 | | 0.4650 | 0.3364 |
| Darocur 4265 (grams) | | 0.6840 | | 0.7983 | | 0.1519 |
| Calc'd Initiator level (wt %) | 1.5% | 3.0% | 1.5% | 3.0% | 1.5% | 2.0% |
| Surface Feel (after 10 passes at 54 fpm) | tacky | tacky | sl tacky | sl tacky | cured | cured |
| MEK double Rubs | 16 | 18 | 30 | 40 | >200 | 200 |

[†]Curing was performed at 22-25° C. and at ambient relative humidity.

This example shows that the trimethylolpropane tris(11-mercaptoundecanoate) of the invention provides a more effective cure than Mercaptanized Soybean Oil in a blend with trimethylolpropane tris(mercaptoacetate), even when the new trimethylolpropane tris(11-mercaptoundecanoate) is more than half by weight of the resin blend (i.e. with the acetate). The blend is required for miscibility purposes since phase separation prevented cure in the case of the pure trimethylolpropane tris(11-mercaptoundecanoate). The ratios were calculated to provide a 1.0 to 1.05 ratio of the mercaptan over the triester (ene) reactant on an equivalent basis.

Epoxy Resin Production

An epoxy resin was produced using pentaerythritol tetrakis (11-mercapto undecanoate) of Run 17 and D.E.R™ 331™ Liquid Epoxy Resin (an epoxy resin reaction product formed from epichlorohydrin and Bisphenol A).

Runs 28 —Epoxy Resin Preparation and Testing

The pentaerythritol tetrakis(11-mercapto undecanoate) of Run 17 was liquefied by warming the bottle with hot tap water. The pentaerythritol tetrakis(11-mercapto undecanoate), 30.04 grams was transferred to a plastic cup. To the plastic cup was added Versamine® EH 30 0.844 grams. The pentaerythritol tetrakis(11-mercapto undecanoate) and Versamine® EH 30 were then mixed together using a flat wooded stick. To the plastic cup was added D.E.R™ 331™ Liquid Epoxy Resin, 28.47 grams. The contents of the cup were then mixed using a flat wooden stick for 3 minutes.

A portion of the cup contents were poured into a Teflon-lined tensile bar mold. The mold was then placed in an oven set at 120° C. for three hours, removed from the oven, allowed to cool, and the cured epoxy resin bar remove from the mold. The epoxy resin bar was then tested for Shore Hardness according to ASTM Method D2240-05 "Standard Test Method for Rubber Property —Durometer Hardness." The epoxy resin had a Shore A Hardness of 58. Dynamic Scanning calorimetry over a range of –60 to 120° C. with a ramp rate of 10° C./min showed a well-defined glass transition temperature at 8.70° C. (inflection point).

To the remainder of the cup mixture was added additional Versamine® EH 30, 0.291 grams. The gel time at ambient temperature (approx. 24° C.) was then determined using a Byk gel timer, which automatically records the time at a point where free rotation of a sample clip in the gelling mixture stops due to the mixture becoming no longer liquid. The epoxy resin had an ambient temperature gel time of approximately 5 hours and the cured cup sample was transparent and homogeneous in appearance with a tough, rubbery character.

What is claimed is:

1. A thiol ester composition comprising thiol ester molecules, the thiol ester molecules having ester linkages comprising:
   a) a residue of glycerol; and
   b) carboxylic acid residues having;
      i) 10 or 11 carbon atoms; and
      ii) a terminal α-hydroxy thiol group; and
   wherein the average ratio of carboxylic acid residues having a terminal α-hydroxy thiol group to hydroxyl groups of glycerol is greater than 0.70:1.

2. The thiol ester composition of claim 1, wherein the carboxylic acid residues having a terminal α-hydroxy thiol group have only 10 carbon atoms.

3. The thiol ester composition of claim 1, wherein the thiol ester molecules have an average thiol sulfur content of 9 to 16 weight percent.

4. A method of producing a thiol ester composition comprising thiol ester molecules, the thiol ester molecules having ester linkages comprising a residue of glycerol and carboxylic acid residues having 10 or 11 carbon atoms and a terminal α-hydroxy thiol group, the method comprising:
   a) contacting ethylene and a natural source oil with a metathesis catalyst composition;
   b) forming unsaturated esters molecules having terminal carbon-carbon double bonds at metathesis conditions capable of forming the unsaturated ester molecules having terminal carbon-carbon double bonds;
   c) contacting the unsaturated ester molecules having terminal carbon-carbon double bonds and an oxygen containing compound;
   d) forming epoxide ester molecules having terminal epoxide groups at conditions capable of forming epoxide ester molecules having terminal epoxide groups;
   e) contacting the epoxide ester composition and hydrogen sulfide; and
   f) forming the thiol ester composition comprising the thiol ester molecules at conditions capable of forming the thiol ester molecules,
   wherein the average ratio of carboxylic acid residues having a terminal α-hydroxy thiol group to hydroxyl groups of glycerol is greater than 0.70:1.

5. The method of claim 4, wherein the metathesis catalyst composition comprises a ruthenium carbene metathesis catalyst or a molybdenum carbene metathesis catalyst.

6. The method of claim 4, wherein the metathesis catalyst comprises dichloro(phenylmethylene) bis(tricyclohexylphosphine) ruthenium or 1,3-bis-(2,4,6-trimethylphenyl)-2-(imidazolidinylidene)(phenylmethylene) dichloro (tricyclohexylphosphine) ruthenium.

7. The method of claim 4, wherein the metathesis conditions include an ethylene partial pressure ranging from 50 to 3000 psig and a temperature ranging from 5° C. to 100° C.

8. The method of claim 4, wherein the natural source oil comprises a tallow oil, an olive oil, a peanut oil, a castor bean oil, a sunflower oil, a sesame oil, a poppy seed oil, a palm oil, an almond seed oil, a hazelnut oil, a rapeseed oil, a canola oil, a soybean oil, a corn oil, a safflower oil, a cottonseed oil, a camelina oil, a flaxseed oil, or a walnut oil, or any combination thereof.

9. The method of claim 4, wherein the natural source oil is soybean oil, corn oil, canola oil, or castor bean oil.

10. The method of claim 4, wherein the natural source oil is soybean oil.

11. A thiol ester composition comprising thiol ester molecules, the thiol ester molecules having ester linkages comprising:
   c) a residue of a polyol; and
   d) carboxylic acid residues having;
      i) at least 4 carbon atoms; and
      ii) a terminal α-hydroxy thiol group; and
   wherein the average ratio of carboxylic acid residues having a terminal α-hydroxy thiol group to hydroxyl groups of the polyol of the residue of the polyol is greater than 0.70:1.

12. The thiol ester composition of claim 11, wherein the carboxylic acid residues have from 6 to 18 carbon atoms.

13. The thiol ester composition of claim 11, wherein the residue of the polyol has from 2 to 12 carbon atoms.

14. The thiol ester composition of claim 11, wherein the polyol of the residue of the polyol has a molecular weight of less than 200 g/mol.

15. The thiol ester composition of claim 11, wherein the polyol of the residue of the polyol is ethane diol, propanediol, butanediol, pentanediol, hexanediol, cyclohexane diol, phenylethane diol, cyclohexanedimethanol, dimethyolpropane, benzenedimethanol, cyclohexanetriol, trihydroxybenzene, trimethyolethane, trimethylolpropane, trimethylolbutane, glycerol, pentaerythritol, sorbitol, or any combination thereof.

16. A method of producing a thiol ester composition comprising thiol ester molecules, the thiol ester molecules having ester linkages comprising a residue of a polyol and carboxylic acid residues having at least 4 carbon atoms and a terminal α-hydroxyl thiol group, the method comprising:
   a) contacting ethylene and a natural source oil with a metathesis catalyst composition;
   b) forming unsaturated esters molecules having terminal carbon-carbon double bonds at metathesis conditions capable of forming the unsaturated ester molecules having terminal carbon-carbon double bonds;
   c) contacting the unsaturated ester molecules having terminal carbon-carbon double bonds and an oxygen containing compound;
   d) forming epoxide ester molecules having terminal epoxide groups at conditions capable of forming epoxide ester molecules having terminal epoxide groups;
   e) contacting the epoxide ester composition and hydrogen sulfide; and
   f) forming the thiol ester composition comprising the thiol ester molecules at conditions capable of forming the thiol ester molecules,
      wherein the average ratio of carboxylic acid residues having a terminal α-hydroxy thiol group to hydroxyl groups of the polyol of the residue of the polyol is greater than 0.70:1.

17. The method of claim 16, wherein the metathesis catalyst composition comprises a ruthenium carbene metathesis catalyst or a molybdenum carbene metathesis catalyst.

18. The method of claim 16, wherein the metathesis catalyst comprises dichloro(phenylmethylene) bis(tricyclohexylphosphine) ruthenium or 1,3-bis-(2,4,6-trimethylphenyl)-2-(imidazolidinylidene)(phenylmethylene) dichloro (tricyclohexylphosphine) ruthenium.

19. The method of claim 16, wherein the metathesis conditions include an ethylene partial pressure ranging from 50 to 3000 psig and a temperature ranging from 5° C. to 100° C.

20. The method of claim 16, wherein the natural source oil comprises a tallow oil, an olive oil, a peanut oil, a castor bean oil, a sunflower oil, a sesame oil, a poppy seed oil, a palm oil, an almond seed oil, a hazelnut oil, a rapeseed oil, a canola oil, a soybean oil, a corn oil, a safflower oil, a cottonseed oil, a camelina oil, a flaxseed oil, or a walnut oil, or any combination thereof.

21. The method of claim 16, wherein the natural source oil is soybean oil, corn oil, canola oil, or castor bean oil.

22. The method of claim 16, wherein the natural source oil is soybean oil.

* * * * *